United States Patent
Tremblay et al.

(10) Patent No.: US 9,512,211 B2
(45) Date of Patent: *Dec. 6, 2016

(54) ANTI-CLUSTERIN ANTIBODIES AND ANTIGEN BINDING FRAGMENTS AND THEIR USE TO REDUCE TUMOR VOLUME

(71) Applicants: ALETHIA BIOTHERAPEUTICS INC., Montreal (CA); NATIONAL RESEARCH COUNCIL OF CANADA, Ottawa (CA)

(72) Inventors: Gilles Bernard Tremblay, La Prairie (CA); Mario Filion, Longueuil (CA); Traian Sulea, Kirkland (CA)

(73) Assignee: Alethia Biotherapeutics Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/311,840

(22) Filed: Jun. 23, 2014

(65) Prior Publication Data

US 2014/0302020 A1 Oct. 9, 2014

Related U.S. Application Data

(62) Division of application No. 13/502,427, filed as application No. PCT/CA2010/001882 on Nov. 24, 2010, now Pat. No. 8,802,826.

(60) Provisional application No. 61/263,865, filed on Nov. 24, 2009.

(51) Int. Cl.
*A61K 39/395* (2006.01)
*C07K 16/18* (2006.01)
*C07K 16/30* (2006.01)
*A61K 45/06* (2006.01)
*A61K 31/337* (2006.01)
*A61K 49/00* (2006.01)

(52) U.S. Cl.
CPC ............ *C07K 16/18* (2013.01); *A61K 31/337* (2013.01); *A61K 39/39558* (2013.01); *A61K 45/06* (2013.01); *A61K 49/0004* (2013.01); *C07K 16/30* (2013.01); *C07K 2317/24* (2013.01); *C07K 2317/33* (2013.01); *C07K 2317/55* (2013.01); *C07K 2317/73* (2013.01); *C07K 2317/76* (2013.01); *C07K 2317/92* (2013.01)

(58) Field of Classification Search
CPC ....... C07K 16/18; C07K 16/30; A61K 39/395; A61K 39/39558
See application file for complete search history.

(56) References Cited

U.S. PATENT DOCUMENTS

| 5,595,756 A | 1/1997 | Bally et al. |
|---|---|---|
| 5,654,407 A | 8/1997 | Boyle et al. |
| 6,342,221 B1 | 1/2002 | Thorpe et al. |
| 6,383,808 B1 | 5/2002 | Monia et al. |
| 6,464,975 B2 | 10/2002 | Millis |
| 6,812,339 B1 | 11/2004 | Venter et al. |
| 6,818,749 B1 | 11/2004 | Kashmiri et al. |
| 6,900,187 B2 | 5/2005 | Gleave et al. |
| 7,279,294 B2 | 10/2007 | Morin et al. |
| 7,285,541 B2 | 10/2007 | Gleave et al. |
| 7,309,487 B2 | 12/2007 | Inana et al. |
| 7,537,931 B2 | 5/2009 | Adams et al. |
| 7,569,551 B2 | 8/2009 | Gleave et al. |
| 7,585,937 B2 | 9/2009 | Kungl |
| 7,597,888 B2 | 10/2009 | Gill et al. |
| 7,691,382 B2 | 4/2010 | Dobson |
| 8,025,878 B2 | 9/2011 | Gellerfors et al. |
| 8,044,179 B2 | 10/2011 | O'Connor-McCourt et al. |
| 8,168,427 B2 | 5/2012 | Sahin et al. |
| 8,426,562 B2 | 4/2013 | O'Connor-McCourt et al. |
| 8,748,398 B2 | 6/2014 | Lee |
| 8,802,826 B2 * | 8/2014 | Tremblay ......... A61K 39/39558 530/387.3 |
| 2003/0091561 A1 | 5/2003 | Van de Winkel |
| 2003/0118592 A1 | 6/2003 | Ledbetter et al. |
| 2003/0133939 A1 | 7/2003 | Ledbetter et al. |
| 2003/0134301 A1 | 7/2003 | Brooksbank et al. |
| 2003/0162702 A1 | 8/2003 | Millis |
| 2003/0211476 A1 | 11/2003 | O'Mahony et al. |
| 2004/0082534 A1 | 4/2004 | Gleave et al. |

(Continued)

FOREIGN PATENT DOCUMENTS

| EP | 1358326 A2 | 11/2003 |
|---|---|---|
| EP | 1603514 A2 | 12/2005 |

(Continued)

OTHER PUBLICATIONS

Chi et al., Clin. Cancer Res. 2008; 14(3):833-39.*
Adamo, V. et al., Gefitinib in lung cancer therapy, Cancer Biology & Therapy, 8:206-212 (2009).
Akashi, Y. et al., Enhancement of the antitumor activity of ionising radiation by nimotuzumab, a humanised monoclonal antibody to the epidermal growth factor receptor, in non-small cell lung cancer cell lines of differing epidermal growth factor receptor status, British Journal of Cancer, 98(4):749-755 (2008).
Al Moustafa, A. et al., Black Cellular Spreading and Motility Assay, BioTechniques, 27(1):60-62 (1999).

(Continued)

*Primary Examiner* — Jessica H Roark
(74) *Attorney, Agent, or Firm* — Fangli Chen; Janique Forget

(57) ABSTRACT

Antibodies and antigen binding fragments that specifically bind to clusterin are described. In some embodiments, the antibodies block the biological activity of clusterin and are useful in composition in certain cancers, more particularly in cancers, such as endometrial carcinoma, breast carcinoma, hepatocellular carcinoma, prostate carcinoma, a renal cell carcinoma, ovarian carcinoma, pancreatic carcinoma, and colorectal carcinoma. The invention also relates to cells expressing the humanized or hybrid antibodies. Additionally, methods of detecting and treating cancer using the antibodies and fragments are also disclosed.

8 Claims, 15 Drawing Sheets

(56) References Cited

U.S. PATENT DOCUMENTS

| | | |
|---|---|---|
| 2004/0220131 A1 | 11/2004 | Jackson et al. |
| 2004/0224914 A1 | 11/2004 | Jackson et al. |
| 2005/0048490 A1 | 3/2005 | Azimzai et al. |
| 2005/0152903 A1 | 7/2005 | Newman et al. |
| 2005/0208558 A1 | 9/2005 | Venter et al. |
| 2005/0222027 A1 | 10/2005 | Chiang et al. |
| 2005/0255114 A1 | 11/2005 | Labat et al. |
| 2006/0029956 A1 | 2/2006 | Beyer et al. |
| 2006/0088532 A1 | 4/2006 | Alitalo et al. |
| 2006/0122141 A1 | 6/2006 | Gleave |
| 2006/0251668 A1 | 11/2006 | Goletz et al. |
| 2006/0258852 A1 | 11/2006 | Lugovskoy et al. |
| 2007/0003547 A1 | 1/2007 | Foote |
| 2007/0015145 A1 | 1/2007 | Woolf et al. |
| 2007/0042945 A1 | 2/2007 | Bodary et al. |
| 2007/0071675 A1 | 3/2007 | Wu et al. |
| 2007/0082337 A1 | 4/2007 | Sorek et al. |
| 2007/0083334 A1 | 4/2007 | Mintz et al. |
| 2007/0099242 A1 | 5/2007 | Heinecke et al. |
| 2007/0105114 A1 | 5/2007 | Li et al. |
| 2007/0117746 A1 | 5/2007 | Dobson |
| 2007/0134260 A1 | 6/2007 | Feger et al. |
| 2007/0224201 A1 | 9/2007 | Wu et al. |
| 2008/0014198 A1 | 1/2008 | Gleave et al. |
| 2008/0064651 A1 | 3/2008 | Gleave et al. |
| 2008/0070995 A1 | 3/2008 | Westbrook et al. |
| 2008/0119425 A1 | 5/2008 | Gleave et al. |
| 2008/0253963 A1 | 10/2008 | Morin et al. |
| 2008/0261912 A1 | 10/2008 | Gleave et al. |
| 2008/0274996 A1 | 11/2008 | Gleave et al. |
| 2008/0286834 A1 | 11/2008 | Halenbeck et al. |
| 2008/0293070 A1 | 11/2008 | Sekaly et al. |
| 2008/0307537 A1 | 12/2008 | Bachoo |
| 2008/0317771 A1 | 12/2008 | Spagnoli et al. |
| 2009/0005541 A1 | 1/2009 | Kungl |
| 2009/0018026 A1 | 1/2009 | Kim et al. |
| 2009/0048171 A1 | 2/2009 | Dobson |
| 2009/0053828 A1 | 2/2009 | Regnier et al. |
| 2009/0081685 A1 | 3/2009 | Beyer et al. |
| 2009/0117578 A1 | 5/2009 | Metz et al. |
| 2009/0144839 A1 | 6/2009 | Inana et al. |
| 2009/0181380 A1 | 7/2009 | Belouchi et al. |
| 2009/0203639 A1 | 8/2009 | Van Criekinge et al. |
| 2009/0208921 A1 | 8/2009 | Tempst et al. |
| 2009/0215709 A1 | 8/2009 | Van Criekinge et al. |
| 2009/0238832 A1 | 9/2009 | Bodary-Winter et al. |
| 2009/0258089 A1 | 10/2009 | Gleave et al. |
| 2009/0280124 A1 | 11/2009 | Labat et al. |
| 2009/0292008 A1 | 11/2009 | Gleave et al. |
| 2010/0075866 A1 | 3/2010 | Hood et al. |
| 2010/0086541 A1 | 4/2010 | Wu et al. |
| 2011/0033471 A1 | 2/2011 | O'Connor-McCourt et al. |
| 2012/0071635 A1 | 3/2012 | O'Connor-McCourt et al. |
| 2015/0044220 A1 | 2/2015 | Tremblay et al. |
| 2015/0111250 A1 | 4/2015 | O'Connor-McCourt et al. |

FOREIGN PATENT DOCUMENTS

| | | |
|---|---|---|
| EP | 1716227 A2 | 11/2006 |
| EP | 1940457 A2 | 7/2008 |
| EP | 2008100 A2 | 12/2008 |
| EP | 2014675 A1 | 1/2009 |
| EP | 2057465 A2 | 5/2009 |
| EP | 2071336 A1 | 6/2009 |
| EP | 2087152 A1 | 8/2009 |
| JP | 2004-513626 A | 5/2004 |
| JP | 2004-521627 A | 7/2004 |
| JP | 2007-535910 A | 12/2007 |
| JP | 2008-506123 A | 2/2008 |
| JP | 2008-520186 A | 6/2008 |
| JP | 2009-507476 A | 2/2009 |
| WO | WO-91/05043 A1 | 4/1991 |
| WO | WO-99/12558 | 3/1999 |
| WO | WO-00/34469 A1 | 6/2000 |
| WO | WO-01/66689 A2 | 9/2001 |
| WO | WO-02/22635 A1 | 3/2002 |
| WO | WO-02/072830 A2 | 9/2002 |
| WO | WO-03/016475 A2 | 2/2003 |
| WO | WO-03/054152 A2 | 7/2003 |
| WO | WO-03/080672 A1 | 10/2003 |
| WO | WO-2004/005934 A2 | 1/2004 |
| WO | WO-2004/050707 A2 | 6/2004 |
| WO | WO-2004066941 A2 | 8/2004 |
| WO | WO-2005/016962 A2 | 2/2005 |
| WO | WO-2005/049806 A2 | 6/2005 |
| WO | WO-2005/058959 A2 | 6/2005 |
| WO | WO-2005/060457 A2 | 7/2005 |
| WO | WO-2005/080434 A1 | 9/2005 |
| WO | WO-2006/010047 A2 | 1/2006 |
| WO | WO-2006/035237 A2 | 4/2006 |
| WO | WO-2006/037604 A1 | 4/2006 |
| WO | WO-2006/056054 A1 | 6/2006 |
| WO | WO-2006/081430 A2 | 8/2006 |
| WO | WO-2006/089586 A1 | 8/2006 |
| WO | WO-2006/113671 A2 | 10/2006 |
| WO | WO-2007/030930 A1 | 3/2007 |
| WO | WO-2007/047995 A2 | 4/2007 |
| WO | WO-2007/123976 A2 | 11/2007 |
| WO | WO-2008/021290 A2 | 2/2008 |
| WO | WO-2008/049239 A1 | 5/2008 |
| WO | WO-2008/085035 A1 | 7/2008 |
| WO | WO-2008/104808 A2 | 9/2008 |
| WO | WO-2009/034562 A2 | 3/2009 |
| WO | WO-2009/061382 A2 | 5/2009 |
| WO | WO-2009/090553 A2 | 7/2009 |
| WO | WO-2009/093246 A2 | 7/2009 |
| WO | WO-2009/116860 A1 | 9/2009 |
| WO | WO-2009/117030 A2 | 9/2009 |
| WO | WO2009/148252 | 12/2009 |
| WO | WO-2010/030980 A2 | 3/2010 |
| WO | WO-2010/118521 A1 | 10/2010 |
| WO | WO-2011/063523 A1 | 6/2011 |
| WO | WO-2013/123588 A1 | 8/2013 |

OTHER PUBLICATIONS

Bailey, R. et al., Clusterin, a Binding Protein with a Molten Globule-like Region, Biochemistry,40:11828-11840 (2001).

Barr, S. et al., Bypassing cellular EGF receptor dependence through epithelial-to-mesenchymal-like transitions, Clinical and Experimental Medicine, 25:685-693 (2008).

Bendig, M.M. et al., Humanization of a Rodent Monoclonal Antibodies by CDR Grafting, Methods: A Companion to Methods in Enzymology, 8:83-93 (1995).

Bird, R.E. et al., Single-Chain Antigen-Binding Proteins, Science, 242(4877):423-426 (1988).

Bodey, B. et al., Failure of Cancer Vaccines: The Significant Limitations of this Approach to Immunotherapy, Anticancer Research, 20:2665-2676 (2000).

Brown, M. et al., Tolerance to single, but not multiple, amino acid replacements in antibody VH CDR 2: a means of minimizing B cell wastage from somatic hypermutation? J Immunol., 156(9):3285-3291 (1996).

Casset, F. et al., A peptide mimetic of an anti-CD4 monoclonal antibody by rational design, Biochemical and Biophysical Research Communications, 307:198-205 (2003).

Cervellera, M. et al. Direct Transactivation of the Anti-apoptotic Gene Apolipoprotein J (Clusterin) by B-MYB, The Journal of Biological Chemistry, 275(28):21055-21060 (2000).

Chatterjee, M.B. et al., Idiotypic antibody immunotherapy of cancer, Cancer Immunology and Immunotherapy, 38:75-82 (1994).

Chen, Y. et al., Selection and Analysis of an Optimized Anti-VEGF Antibody: Crystal Structure of an Affinity-matured Fab in Complex with Antigen, The Journal of Molecular Biology, 293:865-881 (1999).

Chi, K.N. et al., A Phase I Pharmacokinetic and Pharmacodynamic Study of OGX-011, a 2'-Methoxyethyl Antisense Oligonucleotide to Clusterin, in Patients With Localized Prostate Cancer, Journal of the National Cancer Institute, 97(17):1287-1296 (2005).

Chou, T-Y. et al., Clusterin silencing in human lung adenocarcinoma cells induces a mesenchymal-to-epithelial transition through modulating the ERK/Slug pathway, Cellular Signaling, 21(5):704-711 (2009).

(56) References Cited

OTHER PUBLICATIONS

Chung, J. et al. Enhanced chemosensitivity of bladder cancer cells to cisplatin by suppression of clusterin in vitro, Cancer Letters, 203:155-161 (2004).
Clackson, T. et al., Making antibody fragments using phage display libraries, Nature, 352:624-628 (1991).
Colman, P.M., Effects of amino acid sequence changes on antibody-antigen interactions, Research in Immunology, 145:33-36 (1994).
Costanzo, R. et al., Gefitnib in non small cell lung cancer, Journal of Biomedicine and Biotechnology, 2011:815269 (2011).
Dall'Acqua W.F. et al., Antibody humanization by framework shuffling, Methods, 36:43-60 (2005).
De Gruijl, T.D. et al., Cancer vaccine strategies get bigger and better, Nature Medicine, 5:1124-1125 (1999).
De Pascalis, R. et al., Grafting of "Abbreviated" Complementarity-Determining Regions Containing Specificity-Determining Residues Essential for Ligand Contact to Engineer a Less Immunogenic Humanized Monoclonal Antibody, The Journal of Immunology, 169:3076-3084 (2002).
Deng, H.B. et al., Increased Expression of Dihydrodiol Dehydrogenase Induces Resistance to Cisplatin in Human Ovarian Carcinoma Cells, The Journal of Biological Chemistry, 277(17):15035-15043 (2002).
Donnelly, J., Cancer vaccine targets leukemia, Nature Medicine, 11(9):1354-1356 (2003).
Dunker, A.K. et al., Intrinsically disordered protein, Journal of Molecular Graphics and Modelling, 19(1):26-59, (2001).
Durocher, Y. et al., High-level and high-throughput recombinant protein production by transient transfection of suspension-growing human 293-EBNA1 cells, Nucleic Acids Research, 30(2):1-9 (2002).
EMBL Accession No. AF139227.1, Mus musculus anti-fluorescein immunoglobulin light chain mRNA partial cds, first referenced 1999.
EMBL Accession No. AJ965435.1, Synthetic construct for anti-von Willebrand factor A3-domain scFV antibody, first referenced 2005.
Enjalbert, B. et al., Stress-induced Gene Expression in *Candida albicans*: Absence of a General Stress Response; Molecular Biology of the Cell, 14:1460-1467 (2003).
Ensembl Protein ID: ENSCAFP00000012350, Jun. 8, 2010.
Ensembl Protein ID:ENSCAFP00000034804 Jun. 8, 2010.
Ensembl Protein ID:ENSECAP00000005450 Jun. 8, 2010.
Ensembl Protein ID:ENSEEUP00000006956 Jun. 8, 2010.
Ensembl Protein ID:ENSFCAP00000013377 Jun. 8, 2010.
Ensembl Protein ID:ENSMICP00000007021 Jun. 8, 2010.
Ensembl Protein ID:ENSMLUP00000006142 Jun. 8, 2010.
Ensembl Protein ID:ENSMMUP00000032168 Jun. 8, 2010.
Ensembl Protein ID:ENSMMUP00000032169 Jun. 8, 2010.
Ensembl Protein ID:ENSMMUP0000028339 Jun. 8, 2010.
Ensembl Protein ID:ENSMMUP0000032167 Jun. 8, 2010.
Ensembl Protein ID:ENSMMUP0000032170 Jun. 8, 2010.
Ensembl Protein ID:ENSMUSP00000022616 Jun. 8, 2010.
Ensembl Protein ID:ENSOCUP00000005178 Jun. 8, 2010.
Ensembl Protein ID:ENSOPRP00000000527 Jun. 8, 2010.
Ensembl Protein ID:ENSPPYP00000020696 Jun. 8, 2010.
Ensembl Protein ID:ENSPTRP00000034422 Jun. 8, 2010.
Ensembl Protein ID:ENSPTRP00000056651 Jun. 8, 2010.
Ensembl Protein ID:ENSRNOP00000022095 Jun. 8, 2010.
Essabbani, A., et al. Identification of Clusterin Domain Involved in NF-κB Pathway Regulation, The Journal of Biological Chemistry, 285(7):4273-4277 (2010).
Ezzell, C., Cancer "Vaccines": An Idea Whose Time Has Come?, The Journal of NIH Research, 7:46-49 (1995).
Fassina, A. et al., Epithelial-mesenchymal transition in malignant mesothelioma, Modern Pathology, 25(1):86-99 (2012).
Forni, G. et al., Immunoprevention of Cancer: Is the Time Ripe?, Cancer Research, 60:2571-2575 (2000).
GenBank accession No. AAA30846, Hartmann, K. et al. J. Biol. Chem. 266 (15), pp. 9924-9931 (1991).
GenBank accession No. AAA31013, Diemer, V. J. Biol. Chem. 267 (8), pp. 5257-5264 (1992).
GenBank accession No. AAA35692, Jenne, D.E. and Tschopp, J. Journal Proc. Natl. Acad. Sci. U.S.A. 86 (18), pp. 7123-7127 (1989).
GenBank accession No. AAA37284, Hodgdon, B. A. et al. "Secretion of sulfated glycoprotein . . . " Apr. 27, 1993.
GenBank accession No. AAA37422, French, L.E. et al., J. Cell biol. 122 (5), pp. 1119-1130 (1993).
GenBank accession No. AAA41273, Collard, M. W. and Griswold, M. D. J. Biochemistry 26 (12), pp. 3297-3303 (1987).
GenBank accession No. AAA42298, Wong, P. et al. J. Biol. Chem. 268 (7), pp. 5021-5031 (1993).
GenBank accession No. AAA42299, Wong, P. et al. J. Biol. Chem. 268 (7), pp. 5021-5031 (1993).
GenBank accession No. AAA51765, de Silva, H.V. et al., J. Biochemistry 29 (22), pp. 5380-5389 (1990).
GenBank accession No. AAA60321, Danik, M. et al. J. Proc. Natl. Acad. Sci. U.S.A. 88 (19), pp. 8577-8581 (1991).
GenBank accession No. AAA60567, Glew, M.D. et al. Partial mucleotide sequence of the human SP40, 40 gene Jan. 13, 1995.
GenBank accession No. AAA80313, Barber, J. A. et al., "Nucleotide sequence of the complementary DNA . . . " Nov. 1, 1995.
GenBank accession No. AAB06507, Wong P. et al. Eu. J. Biochem. 221 (3), 917-925 (1994).
GenBank accession No. AAB06508, Wong, P. et al. Eur. J. Biochem. 221 (3) pp. 917-925 (1994).
GenBank accession No. AAB25217, Choi-Miura, N.H. et al. J. Biochem. 112 (4), pp. 557-561 (1992).
GenBank accession No. AAB30623, Jordan-Starck, T.C. et al. J. Lipid Res. 35 (2), pp. 194-210 (1994).
GenBank accession No. AAD24461, Miyata, M. et al., Direct submission, Submitted Jan. 8, 1999, First Deaprtment of Internal Medecine, Kagoshima University.
GenBank accession No. AAF06365, Jordan-Starck, T.C. et al., Direct Submission, submittted Sep. 2, 1999, Molecular Developmental Biology.
GenBank accession No. AAF67184, You K.H. and Jeon J.H. Direct Submission, submitted Mar. 22, 2000, Department of Biology, Chungnam National University.
GenBank accession No. AAF67185, You K.H. and Jeon J.H. Direct Submission, submitted Mar. 22, 2000, Department of Biology, Chungnam National University.
GenBank accession No. AAG31162,Park, J. H. et al. Direct Submission Submitted Oct. 19, 2000 Protein Eng. Laboratory, Korea Res.Inst. of Bioscience and Biotechnology.
GenBank accession No. AAH10514, Strausberg R.L. et al., J. Proc. natl. Acad. Sci. U.S.A. 99 (26), pp. 16899-16903 (2002).
GenBank accession No. AAH19588, Strausberg R.L. et al., J. Proc. natl. Acad. Sci. U.S.A. 99 (26), pp. 16899-16903 (2002).
GenBank accession No. AAH61534, Strausberg R.L. et al., J. Proc. natl. Acad. Sci. U.S.A. 99 (26), pp. 16899-16903 (2002).
GenBank accession No. AAH75668, Strausberg, R. L. et al. J., Direct Submission, Proc. Natl. Acad. Sci. U.S.A. 99 (26), pp. 16899-16903 (2002), NIH MGC Project, Jun. 29, 2004.
GenBank accession No. AAP88927, Rieder, M.J. et al., Direct Submission, Submitted Jul. 11, 2003, Genome Sc., University of Washigton.
GenBank accession No. AAT08041, Kim, J.W., Direct Submission, Submitted Dec. 26, 2003, J. Obstet. & Gynecol.Catholic University Medical College.
GenBank accession No. AAV67360—Dorus, S. et al. Direct Submission, Department of Human Genetics, Medical Institute, University of Chicago, Submitted Jun. 14, 2004.
GenBank accession No. AAX36279—Hines, L. et al, Biological Chemistry and Molecular Pharmacology, Harvard Institute of Proteomics, submitted Jan. 4, 2005.
GenBank accession No. AAX41112—Hines, L. et al. Direct Submission, Biol. Chem. and Mol. Pharmacology, Harvard Institute of Proteomics, submitted Jan. 4, 2005.
GenBank accession No. AAX42684—Hines, L. et al. "Direct Submission" Biol.Chem. and Mol. Phar., Harvard Inst. of Proteomics, submitted Jan. 5, 2005.

(56) References Cited

OTHER PUBLICATIONS

GenBank accession No. ABM82371, Rolfs, A. et al., Direct Submission, submitted Jan. 22, 2007.
GenBank accession No. ABM85549, Rolfs, A. et al., Direct Submission, submitted Jan. 22, 2007.
GenBank accession No. BAA03162, You, K.-H. Direct Submission, Submitted Jan. 18, 1993.
GenBank accession No. BAE88332, Chien, H.-C. et al. Direct Submission, submitted Mar. 19, 2004.
GenBank accession No. BAE88970, Chien, H.-C. et al. Direct Submission, submitted Mar. 19, 2004.
GenBank accession No. BAG36598, Isogai, T. and Yamamoto J., Direct Submission, submitted Jan. 11, 2008.
GenBank accession No. BAG52708, Isogai, T. and Yamamoto, J., Direct Submission, submitted Jul. 4, 2002, Helix Research Institute, Genomics Laboratory.
GenBank accession No. CAA31618, Bettuzzi, S., Direct Submission, submitted Oct. 11, 1988) Ben May Institute, University of Chicago.
GenBank accession No. CAA32847, Kirszbaum, L., Direct Submission, submitted Mar. 17, 1999, Clin. Invest. 81, pp. 1858-1864 (1988).
Genbank Accession No. CAC20421; submitted Jan. 2000.
GenBank accession No. CAI45990, Bloecker H. et al., Direct Submission, submitted Jan. 20, 2005, MIPS, Ingolstaedter Landstr. 1.
Gleave, M. et al., Use of antisense oligonucleotides targeting the cytoprotective gene, clusterin, to enhance androgen- and chemosensitivity in prostate cancer. World Journal of Urology, 23(1):38-46 (2005).
Gleave, M.E. et al., Targeting anti-apoptotic genes upregulated by androgen withdrawal using antisense oligonucleotides to enhance androgen- and chemo-sensitivity in prostate cancer, Investigational New Drugs, 20:145-158 (2002).
Gleave, M.E. et al., Use of antisense oligonucleotides targeting the antiapoptotic gene, clusterin/testosterone-repressed prostate message 2, to enhance androgen sensitivity and chemosensitivity in prostate cancer, Urology, 58(Supplement 2A):39-48 (2001).
Hara, I. et al., Introduction of *Clusterin* Gene into Human Renal Cell Carcinoma Cells Enhances Their Resistance to Cytotoxic Chemotherapy through Inhibition of Apoptosis both in vitro and in vivo, Japanese Journal of Cancer Research, 92:1220-1224 (2001).
He, H-Z. et al., Alterations in expression, proteolysis and intracellular localizations of clusterin in esophageal squamous cell carcinoma, World Journal of Gastroenterology, 10(10):1387-1391 (2004).
Herbst, R. and Sandler, A., Bevacizumab and erlotinib: A promising new approach to the treatment of advanced NSCLC, Oncologist, 13:1166-1176 (2008).
Holm, P. et al., Functional mapping and single chain construction of the anti-cytokeratin 8 monoclonal antibody TS1, Molecular Immunology, 44:1075-1084 (2007).
Humphreys, D. et al., Effects of Clusterin Overexpression on TNFα- and TGFβ-Mediated Death of L929 Cells, Biochemistry, 36(49):15233-15243 (1997).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).
Hwang, W.Y.K. et al., Use of human germline genes in a CDR homology-based approach to antibody humanization, Methods: A Companion to Methods in Enzymology, 36:35-42 (2005).
International Search Report for PCT/CA2006/0001505, 5 pages (Dec. 27, 2006).
International Search Report for PCT/CA2013/000167, 5 pages (Jun. 4, 2013).
IPI No. IPI00198667.7, Mar. 14, 2003.
IPI No. IPI00291262.3, Jun. 6, 2003.
IPI No. IPI00320420.3, Jun. 11, 2003.
IPI No. IPI00400826.1, Mar. 3, 2004.
IPI No. IPI00795633.1, Oct. 31, 2006.
IPI No. IPI00753742.1, May 10, 2006.
Jo, H. et al., Cancer Cell-Derived Clusterin Modulates the Phosphatidylinositol-3'-Kinase-Akt Pathway through Attenuation of Insulin-Like Growth Factor 1 during Serum Deprivation, Molecular and Cellular Biology, 28(13):4285-4299 (2008).
Johnson, G. et al., The Kabat Database and a Bioinformatics Example, Methods in Molecular Biology, Antibody Engineering: Methods and Protocols, 248:11-25 (2004).
Jones, D.T., GenTHREADER: An Efficient and Reliable Protein Fold Recognition Method for Genomic Sequences, Journal of Molecular Biology, 287:797-815 (1999).
Jones, P.T. et al., Replacing the complementarity-determining regions in a human antibody with those from a mouse, Nature 321:522-525 (1986).
July, L.V. et al., Clusterin Expression Is Significantly Enhanced in Prostate Cancer Cells Following Androgen Withdrawal Therapy, The Prostate, 50:179-188 (2002).
July, L.V. et al., Nucleotide-based therapies targeting clusterin chemosensitize human lung adenocarcinoma cells both in vitro and in vivo, Molecular Cancer Therapeutics, 3(3):223-232 (2004).
Kalluri, R. and Weinberg, RA, The basics of epithelial-mesenchymal transition, Journal of Clinical Investigation, 119(6):1420-1428 (2009).
Kang, Y.K. et al., Overexpression of Clusterin in Human Hepatocellular Carcinoma, Human Pathology,35(11):1340-1346 (2004).
Kashmiri, S.V.S. et al., SDR grafting—a new approach to antibody humanization, Methods, 36:25-34 (2005).
Kim, S.J. et al., Antibody Engineering for the Development of Therapeutic Antibodies, Molecular Cells, 20(1):17-29 (2005).
Kruger S. et al., Value of clusterin immunoreactivity as a predictive factor in muscle-invasive urothelial bladder carcinoma, Urology, 67(1):105-109 (2006).
Kurahashi, T. et al., Expression of the secreted form of clusterin protein in renal cell carcinoma as a predictor of disease extension, BJU International, 96:895-899 (2005).
Kurisaki, K. et al., Nuclear factor YY1 Inhibits Transforming Growth Factor β- and Bone Morphogenetic Protein-Induced Cell Differentiation, Molecular and Cellular Biology, 23(13):4494-4510 (2003).
Lau, S.H. et al., Clusterin plays an important role in hepatocellular carcinoma metastasis, Oncogene, 25:1242-1250 (2006).
Lee, C-H. et al., Suppression of clusterin expression enhanced cisplatin-induced cytotoxicity on renal cell carcinoma cells, Urology, 60(3):516-520 (2002).
Lee, JM et al., The epithelial-mesenchymal transition: new insights in signaling, development, and disease, Journal of Cellular Biology, 172(7):973-981 (2006).
Lee, K-H. et al., Increased Vaccine-Specific T Cell Frequency After Peptide-Based Vaccination Correlates with Increased Susceptibility to In Vitro Stimulation But Does Not Lead to Tumor Regression, The Journal of Immunology, 163:6292-6300 (1999).
Lenferink, A.E.G. et al., Clusterin Mediates Tumor Promoting, But Not Tumor Suppressing, Effects Of TGF-β1, National Research Council of Canada May 2004, Poster at NRC AGM, 2.
Lenferink, A.E.G. et al., Investigation of three new mouse mammary tumor cell lines as models for transforming growth factor (TGF)-β and Neu pathway signaling studies: identification of a novel model for TGF-β-induced epithelial-to-mesenchymal transition, Breast Cancer Research, 6:R514-R530 (2004).
Lenferink, A.E.G. et al., Transcriptome profiling of a TGF-β-induced epithelial-to-mesenchymal transition reveals extracellular clusterin as a target for therapeutic antibodies, Oncogene, 29(6):831-844 (2010).
Li, X. et al., Predicting Protein Disorder for N-, C- and Internal Regions, Genome Informatics, 10:30-40 (1999).
Lo, B.K.C., Antibody Humanization by CDR Grafting, Methods in Molecular Biology, 248:135-159 (2004).
Lupas, A., Prediction and Analysis of Coiled-Coil Structures, Methods in Enzymology, 266:513-524 (1996).
MacCallum, R.M. et al., Antibody-antigen Interactions: Contact Analysis and Binding Site Topography, Journal of Molecular Biology, 262:732-745 (1996).

(56) References Cited

OTHER PUBLICATIONS

Mirshahadi, H. and Hsueh, C., Updates in non-small cell lung cancer—insights from the 2009 45th annual meeting of the American Society of Clinical Oncology, Journal of Hematology & Oncology, 3:18 (2010).
Miyake, H. et al., Acquisition of Chemoresistant Phenotype by Overexpression of the Antiapoptotic Gene *Testosterone-repressed Prostate Message*-2 in Prostate Cancer Xenograft Models, Cancer Research, 60:2547-2554 (2000).
Miyake, H. et al., Introducing the clusterin gene into human renal cell carninoma cells enhances their metastatic potential, The Journal of Urology, 167:2203-2208 (2002).
Miyake, H. et al., Overexpression of clusterin in transitional cell carcinoma of the bladder is related to disease progression and recurrence, Urology, 59(1):150-154 (2002).
Miyake, H. et al., Resistance to cytotoxic chemotherapy-induced apoptosis in human prostate cancer cells is associated with intracellular clusterin expression, Oncology Reports, 10:469-473 (2003).
NCBI accession No. NM_001831.2, first referenced 1990.
NCBI accession No. NM_013492.2, first referenced 1989.
NCBI accession No. NP_001822, first referenced 1990.
NCBI accession No. NP_038520, first referenced 1989.
NCBI Reference sequence: NP_001003370, Hartmann, K. et al., J. Biol. Chem. 266 (15) pp. 9924-9931 (1991).
NCBI Reference sequence: NP_001075413, Sep. 3, 2009.
NCBI Reference sequence: NP_001075518, Miyata, M., Circulation 104 (12) pp. 1407-1412 (2001).
NCBI Reference sequence: NP_001822, James, R. W. et al. Arterioscler. Thromb. 11 (3) pp. 645-652 (1991).
NCBI Reference sequence: NP_038520, Jenne, D.E. and Tschopp, J. Proc. natl. Acad. Sci. U.S.A. 86 (18), pp. 7123-7127 (1989).
NCBI Reference sequence: NP_444180, Collard, M. W. and Griswold, M. D., Biochemistry 26 (12) pp. 3297-3303 (1987).
NCBI Reference sequence: NP_999136, Diemer, V. et al. J. Biol. Chem. 267 (8), pp. 5257-5264 (1992).
NCBI Reference sequence: XP_001164036, Sep. 15, 2006.
NCBI Reference sequence: XP_001164195, Sep. 15, 2006.
NCBI Reference sequence: XP_001164234, Sep. 15, 2006.
NCBI Reference sequence: XP_001164274, Sep. 15, 2006.
NCBI Reference sequence: XP_001164305, Sep. 15, 2006.
NCBI Reference sequence: XP_001164341, Sep. 15, 2006.
NCBI Reference sequence: XP_001164378, Sep. 15, 2006.
NCBI Reference sequence: XP_001164413, Sep. 15, 2006.
NCBI Reference sequence: XP_001164451, Sep. 15, 2006.
NCBI Reference sequence: XP_001164491, Sep. 15, 2006.
NCBI Reference sequence: XP_001164530, Sep. 15, 2006.
NCBI Reference sequence: XP_001164568, Sep. 15, 2006.
NCBI Reference sequence: XP_001164607 Sep. 15, 2006.
NCBI Reference sequence: XP_001164647 Sep. 15, 2006.
NCBI Reference sequence: XP_001475661 Jun. 20, 2007.
NCBI Reference sequence: XP_519677 Sep. 15, 2006.
NCBI Reference sequence:NP_976084, James, R. W. et al. Arterioscler. Thromb. 11 (3), pp. 645-652 (1991).
Parczyk, K. et al., Gp80 (clusterin; TRPM-2) mRNA level is enhanced in human renal clear cell carcinomas, Journal of Cancer Research and Clinical Oncology, 120:186-188 (1994).
Park, D.C. et al. Clusterin confers paclitaxel resistance in cervical cancer, Gynecologic Oncology, 103(3):996-1000 (2006).
Park, D.C. et al., Clusterin Interacts with Paclitaxel and Confer Paclitaxel Resistance in Ovarian Cancer, Neoplasia Press, 10(9):964-972 (2008).
Paul, W.E., Fundamental Immunology, 3rd Edition, Raven Press, New York, pp. 292-295 (1993).
Pines, G. et al., Oncogenic Mutant Forms of EGFR: Lessons in Signal Transduction and Targets for Cancer Therapy, FEBS Letters, 584:2699-2706 (2010).
Portolano, S. et al., Lack of Promiscuity in Autoantigen-Specific H and L Chain Combinations as Revealed by Human H and L Chain "Roulette", The Journal of Immunology, 150:880-887 (1993).

Queen, C. et al., A humanized antibody that binds to the interleukin 2 receptor, Proceedings of the National Academy of Sciences of the United States of America, 86:10029-10033 (1989).
Redondo, M. et al., Anticlusterin treatment of breast cancer cells increases the sensitivities of chemotherapy and tamoxifen and counteracts the inhibitory action of dexamethasone on chemotherapy-induced cytotoxicity, Breast Cancer Research, 9(6):1465-5411 (2007).
Redondo, M. et al., Overexpression of Clusterin in Human Breast Carcinoma, American Journal of Pathology, 157(2):393-399 (2000).
Riechmann, L. et al., Reshaing human antibodies for therapy, Nature 332:323-327 (1988).
Ronquist, K.G. et al., Serum antibodies against prostasomal clusterin in prostate cancer patients, Scand. J. Clin. Lab Invest., 68(3):219-27 (2008).
Rost, B., Predicting One-Dimensional Protein Structure by Profile-Based Neural Networks, Methods in Enzymology, 266:525-539 (1996).
Rudikoff, S. et al., Single amino acid substitution altering antigen-binding specificity, Proceedings of the National Academy of Science of the United States of America, 79:1979-1983 (1982).
Saffer, H. et al., Clusterin Expression in Malignant Lymphomas: A Survey of 266 Cases, Modern Pathology, 15(11):1221-1226 (2002).
Sanders, M.L. et al., α-Specific Anti-clusterin Antibody: Development and Characterization, Molecular Biology of the Cell, American Society for Cell Biology, US, vol. 4, Suppl. p. 109A, 1993.
Santa Cruz Biotechnology, Inc. Clusterin-α (C-18): sc-6419, Santa Cruz Biotechnology Inc. Catalog, pp. 1 (1999).
Santa Cruz Biotechnology, Inc., Clustrein-α (B-5): sc-5289, Santa Cruz Biotechnology Inc. Catalog, pp. 1 (2004).
Scaltriti, M. et al., Clusterin (SGP-2, ApoJ) expression is downregulated in low- and high-grade human prostate cancer, International Journal of Cancer, 108(1):23-30 (2004).
Schade, B. et al., Cold Adaptation in Budding Yeast, Molecular Biology of the Cell, 15:5492-5502 (2004).
Schedule A submitted to European Patent Office Dec. 21, 2010.
Schedule B submitted to European Patent Office Sep. 2, 2011.
Schlapschy, M. et al., Functional humanization of an anti-CD30 Fab fragment for the immunotherapy of Hodgkin's lymphoma using an in vitro evolution approach, Protein Engineering, Design & Selection, 17(12):847-860 (2004).
Shigematsu, H. et al., Clinical and biological features associated with epidermal growth factor receptor gene mutations in lung cancers, Journal of the National Cancer Institute, 97:339-346 (2005).
Singh, J. et al., Transforming in the TGFβ pathway: Convergence of distinct lead generation strategies on a novel kinase pharmacophore for TβRI (ALK5), Current Opinion in Drug Discovery & Development, 74(4):437-445 (2004).
Sintich, S.M. et al., Cytotoxic Sensitivity to Tumor Necrosis Factor-α in PC3 and LNCaP Prostatic Cancer Cells Is Regulated by Extracellular Levels of SGP-2 (Clusterin), The Prostate 39:87-93 (1999).
Sintich, S.M. et al., Transforming Growth Factor-β1-Induced Proliferation of the Prostate Cancer Cell Line, TSU-Pr1: The Role of Platelet-Derived Growth Factor, Endocrinology, 140:(8):3411-3415 (1999).
So, A. et al., Antisense oligonucloetide therapy in the management of bladder cancer, Current Opinion in Urology, 15:320-327 (2005).
So, A. et al., Knockdown of the cytoprotective chaperone, clusterin, chemosensitizes human breast cancer cells both in vitro and in vivo, Molecular Cancer Therapy, 4(12):1837-1849 (2005).
Springate, C.M.K, et al., Efficacy of an intratumoral controlled release formulation of clusterin antisense oligonucleotide complexed with chitosan containing paclitaxel or docetaxel in prostate cancer xenograft models, Cancer Chemotherapy and Pharmacology, 56(3):239-247 (2005).
Staelens, S. et al., Humanization by variable domain resurfacing and grafting on a human $IgG_4$, using a new approach for determination of non-human like surface accessible framework residues based on homology modelling of variable domains, Molecular Immunology, 43:1243-1257 (2006).

(56) References Cited

OTHER PUBLICATIONS

Steinberg, J. et al., Intracellular Levels of SGP-2 (Clusterin) Correlate with Tumor Grade in Prostate Cancer, Clinical Cancer Research, 3:1707-1711 (1997).
SwissProt Accession No. P01625.2; submitted Aug. 1996.
Tamura, M. et al., Structural correlates of an anticarcinoma antibody: identification of specificity-determining residues (SDRs) and development of a minimally immunogenic antibody variant by retention of SDRs only, J. Immunol., 164(3):1432-41 (2000).
Tatusova, T. et al., Blast 2 sequences, a new tool for comparing protein and nucleotide sequences, FEMS Microbiology Letters, 174:247-250 (1999).
Thomas-Tikhonenko, A. et al., Myc-Transformed Epithelial Cells Down-Regulate Clusterin, Which Inhibits Their Growth in Vitro and Carcinogenesis in Vivo, Cancer Research, 64:3126-3136 (2004).
Tremblay, G. et al., Poster Presentations—Translational Metastasis Research, Abstract 1467: AB-16B5, a therapeutic monoclonal antibody against human clusterin that blocks the epithelial-to-mesenchymal transition, Proceedings: AACR 101st Annual Meeting, 2010—Apr. 17-21, 2010 Washington, DC.
Trougakos, I.P. et al., Advances and Challenges in Basic and Translational Research on Clusterin, Cancer Research, 69(2):403-406 (2009) (including 4 pages of "Supplementary Data").
Trougakos, I.P. et al., Silencing Expression of the Clusterin/Apolipoprotein J Gene in Human Cancer Cells Using Small Interfering RNA Induces Spontaneous Apoptosis, Reduced Growth Ability, and Cell Sensitization to Genotoxic and Oxidative Stress, Cancer Research, 64(5):1834-1842 (2004).
Trougakos, I.P. et al., Differential effects of clusterin/apolipoprotein J on cellular growth and survival, Free Radical Biology & Medicine, 38:436-449 (2005).
Tsurushita, N. et al., Design of humanized antibodies: from anti-Tac to Zenapax, Methods, 36(1):69-83 (2005).
Uni-Prot/TrEMBL accession No. Q549A5_MOUSE, McLaughlin L. et al., J. Clin. Invest. 106:1105-1113 (2000) May 24, 2005.
Uni-Prot/TrEMBL accession No. Q5ISQ2_MACFA, Dorus S. et al., Cell 119:1027-1040 (2004).
Uni-Prot/TrEMBL accession No. Q6P7S6_RAT, Jul. 5, 2004.
Uni-Prot/TrEMBL accession No. Q9ERD1_RAT, Park J. H. et al., submitted Oct. 2000, Mar. 1, 2001.
UniProtKB/Swiss-Prot accession No. P05371 (CLUS_RAT), Collard M.W. and Grisworld M.D., Biochemistry 26:3297-3303 (1987).
UniProtKB/Swiss-Prot accession No. P10909 (CLUS_HUMAN), Jenne D.E. and Tschopp J., Proc. natl. Acad. Sci. U.S.A. 86:7123-7127 (1989), Jul. 1, 1989.
UniProtKB/Swiss-Prot accession No. P25473 (CLUS_CANFA), Hartmann K. et al., J. Biol. Chem, 266:9924-9931 (1991) May 1, 1992.
UniProtKB/Swiss-Prot accession No. Q06890 (CLUS_MOUSE), Lee K.-H. et al. Biochem. Biophys. Res. Commun. 194:1175-1180 (1993) PubMed: 8352774 Abstract, Feb. 1, 1995.
UniProtKB/Swiss-Prot accession No. Q29482 (CLUS_HORSE), Barber J. A. et al., submitted Nov. 1995, May 10, 2005.
UniProtKB/Swiss-Prot accession No. Q29549 (CLUS_PIG), Diemer V. et al., J. Biol. Chem. 267:5257-5264 (1992), Jul. 15, 1998.
UniProtKB/Swiss-Prot accession No. Q9XSC5 (CLUS_RABIT), Miyata M. et al., Circulation 104:1407-1412 (2001) Dec. 1, 2000.
Vajdos, F.F. et al., Comprehensive Functional Maps of the Antigen-binding Site of an Anti-ErbB2 Antibody Obtained with Shotgun Scanning Mutagenesis, The Journal of Molecular Biology, 320:415-428 (2002).
Van Der Keyl, H. et al., Disparity in the kinetics of onset of hypermutation in immunoglobulin heavy and light chains, Immunology and Cell Biology, 78:224-237 (2000).
Verhoeyen, M. et al., Reshaping Human Antibodies: Grafting an Antilysozyme Activity, Science, 239:1534-1536 (1988).

Wang, X., Expression and role of clusterin in apoptosis of prostatic epithelial cell, Journal of Modern Urology, 13(1):41-43 (2008). English Abstract.
Ward, E.S. et al., Binding activities of a repertoire of single immunoglobulin variable domains secreted from *Escherichia coli*, Nature, 341:544-546 (1989).
Wilson, M.R. et al., Clusterin binds by a multivalent mechanism to the Fc and Fab regions of IgG; Biochimica et Biophysica Acta; 1159:319-326 (1992).
Witta, S. et al., Restoring E-cadherin expression increases sensitivity to epidermal growth factor receptor inhibitors in lung cancer cell lines, Cancer Research, 66:944-950 (2006).
Written Opinion for PCT/CA2006/0001505, 9 pages (Dec. 27, 2006).
Wu, H. et al., Humanization of a Murine Monoclonal Antibody by Simultaneous Optimization of Framework and CDR Residues, The Journal of Molecular Biology, 294:151-162 (1999).
Wu, H., Simultaneous Humanization and Affinity Optimization of Monoclonal Antibodies, Methods in Molecular Biology, 207:197-212, Humana Press Inc., Totowa, New Jersey (2003).
Xie, D. et al., Oncogenic role of clusterin overexpression in multistage colorectal tumorigenesis and progression, World Journal of Gastroenterology, 11(21):3285-3289 (2005).
Xie, D. et al., Up-Regulated Expression of Cytoplasmic Clusterin in Human Ovarian Carcinoma, Cancer, 103(2):277-283 (2005).
Yauch, R. et al., Epithelial versus mesenchymal phenotype determines in vitro sensitivity and predicts clinical activity of erlotinib in lung cancer patients, Clinical Cancer Research, 5:8686-8698 (2005).
Zellweger, T. et al., Antitumor Activity of Antisense Clusterin Oligonucleotides Is Improved in Vitro and in Vivo by Incorporation of 2'-O-(2-Methoxy)Ethyl Chemistry, The Journal of Pharmacology and Experimental Therapeutics, 298(3):934-940 (2001).
Zellweger, T. et al., Chemosensitization of Human Renal Cell Cancer Using Antisense Oligonucleotides Targeting the Antiapoptotic Gene Clusterin, Neoplasia, 3(4):360-367 (2001).
Zhang, L-Y. et al., Loss of clusterin both in serum and tissue correlates with the tumorigenesis of esophageal squamous cell carcinoma via proteomics approaches, World Journal of Gastroenterology, 9(4):650-654 (2003).
Zhang, Y. et al., Preparation and characterization of antibodies against clusterin, Chinese Journal of Cellular and Molecular Immunology, 24(1):45-48 (2008).
Zhou, W. et al., A novel anti-proliferative property of clusterin in prostate cancer cells, Life Sciences, 72(1):11-21 (2002).
Zoubeidi, A. et al., Clusterin Facilitates COMMD1 and I-κB Degradation to Enhance NF-κB Activity in Prostate Cancer Cells, Molecular Cancer Research, 8:119-130 (2010).
Aagaard, L. and Rossi, J.J., RNAi therapeutics: principles, prospects and challenges, Adv. Drug Deliv. Rev., 59(2-3):75-86 (2007).
Auerbach, R. et al., Angiogenesis assays: problems and pitfalls, Cancer Metastasis Rev., 19(1-2):167-72 (2000).
Bowie, J.U. et al., Deciphering the message in protein sequences: tolerance to amino acid substitutions, Science, 247(4948):1306-10 (1990).
Burgess, W.H. et al., Possible dissociation of the heparin-binding and mitogenic activities of heparin-binding (acidic fibroblast) growth factor-1 from its receptor-binding activities by site-directed mutagenesis of a single lysine residue, J. Cell Biol., 111(5 Pt 1):2129-38 (1990).
Chowdhury, P.S. and Vasmatzis, G., Engineering scFvs for Improved Stability, Methods in Molecular Biology, Recombinant Antibodies for Cancer Therapy: Methods and Protocols, Welschof, M. and Krauss, J. ed., vol. 207, chapter 14, pp. 237-254 (2003).
Clark, J.D. et al., Discovery and development of Janus kinase (JAK) inhibitors for inflammatory diseases, J. Med. Chem., 57(12):5023-38 (2014).
Guido, R.V. et al., Virtual screening and its integration with modern drug design technologies, Curr. Med. Chem., 15(1):37-46 (2008).
Gura, T., Systems for identifying new drugs are often faulty, Science, 278(5340):1041-2, encloses 1-5 (1997).
International Search Report for PCT/CA2010/001882, 5 pages (Feb. 16, 2011).

(56) References Cited

OTHER PUBLICATIONS

Jain, R.K., Barriers to drug delivery in solid tumors, Sci. Am., 271(1):58-65 (1994).
Lazar, E. et al., Transforming growth factor alpha: mutation of aspartic acid 47 and leucine 48 results in different biological activities, Mol. Cell. Biol., 8(3):1247-52 (1988).
McKeague, M. and Derosa, M.C., Challenges and opportunities for small molecule aptamer development, J. Nucleic Acids., 2012:748913, 20 pages (2012).
Roguska, M.A. et al., A comparison of two murine monoclonal antibodies humanized by CDR-grafting and variable domain resurfacing, Protein. Eng., 9(10):895-904 (1996).
Roitt, I. et al., Immunology, Mosby, chapter 6, pp. 110-111 (2000) [with English translation].
Sporn, M.B. and Suh, N., Chemoprevention of cancer, Carcinogenesis, 21(3):525-30 (2000).
Warzocha, K. and Wotowiec, D., Antisense strategy: biological utility and prospects in the treatment of hematological malignancies, Leuk. Lymphoma., 24(3-4):267-81 (1997).
Wei, L. et al., Roles of clusterin in progression, chemoresistance and metastasis of human ovarian cancer, Int. J. Cancer., 125(4):791-806 (2009).
Written Opinion for PCT/CA2010/001882, 7 pages (Feb. 16, 2011).
Written Opinion for PCT/CA2013/000167, 7 pages (Jun. 4, 2013).
Beiboer, S.H. et al., Guided Selection of a Pan Carcinoma Specific Antibody Reveals Similar Binding Characteristics yet Structural Divergence Between the Original Murine Antibody and its Human Equivalent, J. Mol. Biol. vol. 296, pp. 833-849, 2000.
Berx G, et al. Pre-EMTing metastasis? Recapitulation of morphogenetic processes in cancer. Chn. Exp. Metastasis. 24: 587, 2007.
Chi, K.N. et al., A Phase I Study of OGX-011, a 2'-Methoxyethyl Phosphorothioate Antisense to Clusterin, in Combination with Docetaxel in Patients with Advanced Cancer, Clin Cancer Res. 14(3):833-839, 2008.
Gupta GP, et al. Cancer metastasis: building a framework. Cell. 127: 679, 2006.
Houdebine L.M., Production of Pharmaceutical Proteins from Transgenic Animals, Journal of Biotechnology, vol. 34, pp. 269-287, 1994.
Kappel C. A. et al., Regulating Gene Expression in Transgenic Animals, Current Opinions in Biotechnology, vol. 3, pp. 548-553, 1992.
Klimka, A. et al., Human Anti-CD30 Recombinant Antibodies by Guided Phage Antibody Selection Using Cell Panning, British Journal of Cancer, vol. 83, pp. 252-260, 2000.
Mader, A. and R. Kunert, Humanization Strategies for an Anti-Idiotypic Antibody Mimicking HIV-1 gp41, Prot. Engin. Design & Select. 23(12): 947-954, 2010: published online Oct. 30, 2010.
Margreitter, C. et al., Antibody Humanization by Molecular Dynamics Simulations—In Silico Guided Selection of Critical Backmutations, J. Mol. Recognit 29(6), 266-275, 2016.
Massague J. TGFbeta in Cancer. (2008) Cell. 134: 215.
Mourra N, et al. (2007) Clusterin is highly expressed in pancreatic endocrine tumours but not in solid pseudopapillary tumours. Histopathology. 50: 331, 2007.
Nguyen, H.P. et al., Protein Data Bank No. 1Q9Q (now replaced by No. 3sy0), first referenced 2011 (2 pages).
Panka, D.J. et al., Variable Region Framework Differences Result in Decreased or Increased Affinity of Varian Anti-Digoxin Antibodies, PNAS, USA, vol. 85, p. 3080-3084, 1988.
Pirker, R., J. R., Peirera et al., (2012) "EGFR expression as a predictor of survival for first-line chemotherapy plus cetuximab in patients with advanced non-small-cell lung cancer: analysis of data from the phase 3 FLEX study." *Lancet* 13:33.
Ranney, M.K. et al., Multiple Pathways Regulating the Anti-Apoptotic Protein Clusterin in Breast Cancer, Biochimica et Biophysica Acta, 1772, 1103-1111, 2007.
Schmiedel, J. et al., Matuzumab Binding to EGFR Prevents the Conformational Rearrangement Required for Dimerization, Cancer Cell, 13(4): 365-373, 2008.
Springer T.A. et al., Protein Data Bank No. 1TY7 (now replaced by No. 2vc2), first referenced 2008 (4 pages).
Tan, P. et al, "Superhumanized" Antibodies: Reduction of Immunogenic Potential by Complementarrity-Determining Region Grafting with Human Germline Sequences: Application to an Anti-CD28, J. Immunol. 169:1119-1125, 2002.
Tremblay, G.B. et al., Abstract LB-33: Pre-clinical evaluation of AB-16B5, a monoclonal antibody specific for tumor-associated sCLU, demonstrates therapeutic potential as an inhibitor of EMT in prostate, pancreatic and lung cancer, Cancer Research, Abstract, 1 page (2011).
Tremblay, G.B. et al., Abstract LB-33: Pre-clinical evaluation of AB-16B5, a monoclonal antibody specific for tumor-associated sCLU, demonstrates therapeutic potential as an inhibitor of EMT in prostate, pancreatic and lung cancer, Cancer Research, Poster #LB-33, 1 page (2011).
Trougakos, I.P. et al., Intracellular Clusterin Inhibits Mitochondrial Apoptosis by Suppressing p53-Activating Stress Signals and Stabilizing the Cytosolic Ku70-Bax Protein Complex, Clin Cancer Res, 15(1) 48-59, 2009.
Wall R.J., Transgenic Livestock: Progress and Prospects for the Future, Theriogenology, vol. 45, pp. 57-68, 1996.
Watari H, et al. , Clusterin expression predicts survival of invasive cervical cancer patients treated with radical hysterectomy and systematic lymphadenectomy. Gynecol. Oncol. 108: 527, 2008.
Zhang S, et al., Clusterin expression and univariate analysis of overall survival in human breast cancer. Technol. Cancer Res. Treat. 5: 573, 2006.

* cited by examiner

FIGURE 3

|          | $K_a$ (1/Ms) | | $K_d$ (1/s) | | $K_D$ (M) | |
|----------|---------|----------|---------|----------|----------|----------|
|          | Average | Stdev    | Average | Stdev    | Average  | Stdev    |
| 16B5 Fab  | 7.41e+04 | 2.03e+04 | 0.0030 | 0.0006 | 4.16e-08 | 7.87e-09 |
| 16B5      | 3.29e+05 | 1.16e+05 | 0.0017 | 0.0005 | 6.64e-09 | 4.66e-09 |
| HH16B5 Fab| 1.59e+05 | 1.89e+04 | 0.0027 | 0.0004 | 1.72e-08 | 2.97e-09 |
| HH16B5    | 3.45e+05 | 4.89e+04 | 0.0015 | 0.0005 | 4.49e-09 | 8.65e-10 |

FIGURE 8

21B12 humanization

VL (14 mutations, 100% framework humanization):

VH (18 mutations, 100% framework humanization):

21B12 murine VL= SEQ ID NO.:33 (CDRs are highlighted)
21B12 humanized VL = SEQ ID NO.:18 (CDRs are highlighted)
Human model of 21B12 VL= SEQ ID NO.:43
21B12 murine VH=SEQ ID NO.:37 (CDRs are highlighted)
21B12 humanized VH=SEQ ID NO.:17 (CDRs are highlighted)
Human model of 21B12 VH= SEQ ID NO.:58 buried
within 5Å from CDRs (Kabat definition)
close to VH
close to VL

[a] http://www.ncbi.nlm.nih.gov/protein/1730075
[b] http://www.ncbi.nlm.nih.gov/protein/3170803

FIGURE 9

|  | $K_a$ (1/Ms) | | $K_d$ (1/s) | | $K_D$ (M) | |
|---|---|---|---|---|---|---|
|  | Average | Stdev | Average | Stdev | Average | Stdev |
| 21B12 Fab | 2.15e+05 | 4.56e+04 | 0.00352 | 0.00092 | 2.53e-08 | 8.26e-09 |
| 21B12 | 3.62e+05 | 1.27e+5 | 0.0015 | 0.00074 | 5.09e-09 | 3.98e-09 |
| HH21B12 | 3.74e+05 |  | 0.00083 |  | 2.23e-09 |  |

FIGURE 15

Query is human clusterin (NP_001822)
Sbjct is murine clusterin (NP_038520)

Identities = 334/435 (77%), Positives = 384/435 (89%), Gaps = 0/435 (0%)

```
Query   67   WESGQVLGDQTVSDNELQEMSNQGSKYVNKEIQNAVNGVKQIKTLIEKTNEERKTLLSNL   126
SEQ NO.56    W++G VLG+Q VSDNELQE+S QGS+Y+NKEIQNAV GVK IKTLIEKTN ERK LL  L
SEQ NO.57    W  G VLG Q VSDNELQE S QGS Y NKEIQNAV GVK IKTLIEKTN ERK LL   L
Sbjct   14   WDNGMVLGEQEVSDNELQELSTQGSRYINKEIQNAVQGVKHIKTLIEKTNAERKSLLNSL   73

Query   127  EEAKKKKEDALNETRESETKLKELPGVCNETMMALWEECKPCLKQTCMKFYARVCRSGSG   186
SEQ NO.56    EEAKKKKEDAL +TR+SE KLK  P VCNETMMALWEECKPCLK TCMKFYARVCRSGSG
SEQ NO.57    EEAKKKKEDAL  TR SE KLK  P VCNETMMALWEECKPCLK TCMKFYARVCRSGSG
Sbjct   74   EEAKKKKEDALEDTRDSEMKLKAFPEVCNETMMALWEECKPCLKHTCMKFYARVCRSGSG   133

Query   187  LVGRQLEEFLNQSSPFYFWMNGDRIDSLLENDRQQTHMLDVMQDHFSRASSIIDELFQDR   246
SEQ NO.56    LVG+QLEEFLNQSSPFYFWMNGDRIDSLLE DRQQ+  D MQD F+RAS IID LFQDR
SEQ NO.57    LVG QLEEFLNQSSPFYFWMNGDRIDSLLE DRQQ    D MQD F RAS IID LFQDR
Sbjct   134  LVGQQLEEFLNQSSPFYFWMNGDRIDSLLESDRQQSQVDAMQDSFARASGIIDTLFQDR   193

Query   247  FFTREFQDTYHYLPFSLPHRRPHFFFPKSRIVRSLMPFSPYEPLNFHAMFQPFLEMIHEA   306
SEQ NO.56    FF RE  D  ++  P     FH RPHF +PKSR+VRSLM  S Y P +FH MFQPF EMIH+A
SEQ NO.57    FF RE  D     P     FH RPHF PKSR VRSLM  S Y P  FH MFQPF EMIH A
Sbjct   194  FFARELFDPHYFSPIGFHHKRPHFLYPKSRLVRSLMSPSHYGPPSFHNMFQPFFEMIHQA   253

Query   307  QQAMDIEFHSPAFQHPPTEFIREGDDDRTVCREIRHNSTGCLRMKDQCDKCREILSVDCS   366
SEQ NO.56    QQAMD+  HSPAFQ P  +F+REG+DDRTVC+EIR NSTGCL MK  QC+KC+EILSVDCS
SEQ NO.57    QQAMD   HSPAFQ P   F REG DDRTVC EIR NSTGCL MK  QC KC EILSVDCS
Sbjct   254  QQAMDVQLHSPAFQFPDVDFLREGEDDRTVCKEIRRNSTGCLKMKGQCEKCQEILSVDCS   313

Query   367  TNNPSQAKLRRELDESLQVAERLTRKYNELLKSYQWKMLNTSSLLEQLNEQFNWVSRLAN   426
SEQ NO.56    TNNP+QA LR+EL++SLQVAERLT +Y ELL+S Q KMLNTSSLLEQLN+QFNWVS+LAN
SEQ NO.57    TNNP QA LR EL  SLQVAERLT  Y ELL S Q KMLNTSSLLEQLN QFNWVS LAN
Sbjct   314  TNNPAQANLRQELNDSLQVAERLTEQYKELLQSFQSKMLNTSSLLEQLNDQFNWVSQLAN   373

Query   427  LTQGEDQYYLRVTTVASHTSDSDVPSGVTEVVVKLFDSDPITVTPVEVSRKNPKFMETV   486
SEQ NO.56    LTQGED YYLRV+TV +H+SDS+VPS VTEVVVKLFDSDPITV +P EVS+ NPKFM+TV
SEQ NO.57    LTQGED YYLRV TV  H SDS VPS VTEVVVKLFDSDPITV  P EVS  NPKFM TV
Sbjct   374  LTQGEDKYYLRVSTVTTHSSDSEVPSRVTEVVVKLFDSDPITVVLPEEVSKDNPKFMDTV   433

Query   487  AEKALQEYRKKHREE   501
SEQ NO.56    AEKALQEYR+K R E
SEQ NO.57    AEKALQEYR K R E
Sbjct   434  AEKALQEYRRKSRAE   448
```

ANTI-CLUSTERIN ANTIBODIES AND ANTIGEN BINDING FRAGMENTS AND THEIR USE TO REDUCE TUMOR VOLUME

PRIORITY CLAIM

This patent application is a divisional of U.S. Ser. No. 13/502,427 filed on Jul. 26, 2012, now U.S. Pat. No. 8,802,826 which is a national stage filing under 35 U.S.C. §371 of international application No. PCT/CA2010/001882 filed on Nov. 24, 2010, which claimed priority to U.S. provisional application No. 61/263,865 filed Nov. 24, 2009. The entire contents of each of these priority applications are incorporated herein by reference.

FIELD OF THE INVENTION

The invention relates to anti-clusterin antibodies and their use to reduce tumor volume. The invention more particularly relates to humanized antibodies, hybrid antibodies and antigen binding fragment which bind to clusterin and their use to reduce tumor volume, to inhibit tumor growth and metastasis.

BACKGROUND OF THE INVENTION

Carcinomas, the most common human malignancy, arise from epithelial cells. Progression of epithelial cancers begins with the disruption of cell-cell contacts as well as the acquisition of a migratory (mesenchymal-like) phenotype. This phenomenon, which is called an epithelial-to-mesenchymal transition (EMT), is considered to be a crucial event in late stage tumor progression and metastasis.

The secreted protein TGF-β suppresses tumor growth initially largely due to its growth inhibitory action on tumor cells of epithelial origin, then at later stages promotes tumor cell progression and metastasis. One mechanism by which TGF-β can promote tumor progression is through the induction of an EMT.

Due to the dual role that TGF-β plays in carcinogenesis, direct inhibitors of TGF-β may be risky since, while they could benefit late stage tumors, they could also accelerate preneoplastic lesions. A better therapeutic may be one that inhibits the pro-oncogenic EMT-promoting action of TGF-β, while leaving the tumor suppressor growth-inhibitory action of TGF-β unaffected. To develop such an inhibitor it would be necessary to identify the point at which there is a bifurcation of the TGF-β signaling pathway such that the mediators in one branch of the pathway participate in the EMT response, but not the growth inhibitory response to TGF-β. Therapeutics that inhibit mediators that lie exclusively in the EMT-promoting branch of the TGF-β signaling pathway will reduce metastasis while having little or no effect on the acceleration of preneoplastic lesions.

No TGF-β signal pathway specific components have been generally identified that promote or mediate the EMT-promoting action of TGF-β, yet are not involved in the growth inhibitory action of TGF-β.

In contrast, an endogenous protein (the YY1 nuclear factor) has been identified that is able to interfere with (as opposed to promote) the protumorigenic EMT action of TGF-β, while leaving the tumor-suppressing action (growth inhibition) intact (Kurisaki et al., 2004).

Inhibitors that target TGF-β ligands, receptors and the Smad signaling proteins are known. Specifically, soluble receptor ectodomains, antibodies and other binding proteins are able to act as antagonists by interacting with TGF-β ligands and sequestering them away from cell surface receptors. Small molecules are available that inhibit the kinase activity of the Type I TGF-β receptor and endogenous inhibitors of the Smad signaling proteins are also known. Since all of these signaling pathway components are involved in both the pro- and anti-carcinogenic actions of TGF-β, these inhibitors that target them may benefit late stage tumors, however, they could also accelerate preneoplastic lesions.

International patent application No. PCT/CA2006/001505 filed on Sep. 13, 2006 and published on Mar. 22, 2007 under No. WO2007/030930 describes anti-clusterin antibodies and antigen binding fragments that are directed to a specific epitope of clusterin and that are capable of inhibiting epithelial-to-mesenchymal transition of carcinoma cells. This patent application more particularly shows the ability of anti-clusterin antibodies at inhibiting EMT in prostate carcinoma and breast carcinoma.

SUMMARY OF THE INVENTION

The present invention relates in one aspect thereof to an antibody which is capable of specific binding to clusterin and which comprises a humanized light chain variable region and/or a humanized heavy chain variable region.

More particularly, the present invention provides a humanized antibody of a non-human parent antibody that is capable of specific binding to clusterin as well as hybrid antibodies and antigen binding fragment thereof.

The humanized or hybrid antibodies of the present invention comprise light chain variable region and a heavy chain variable region which may include non-human complementarity determining region amino acid residues and human framework region amino acid residues of a natural human antibody.

The present invention also relates to an antigen binding fragment comprising a light chain variable region and a heavy chain variable region, which may include non-human complementarity determining region amino acid residues and human framework region amino acid residues.

The antibodies and antigen binding fragment of the present invention may be used to inhibit epithelial-to-mesenchymal transition induced by clusterin.

In another aspect, the present invention relates to an anti-clusterin antibody (a polyclonal antibody, a monoclonal antibody, a chimeric antibody, a humanized antibody, an isolated human antibody, a hybrid antibody or a fragment thereof) for use in reducing tumor volume and methods for doing so.

Also encompassed by the present invention are isolated nucleic acids encoding the light chain variable region and/or the heavy chain variable region of the humanized antibody, the hybrid antibody or the antigen binding fragment described herein or the isolated antibody described herein.

Also encompassed herewith is a vector or construct, comprising the nucleic acid described herein. In accordance with the present invention, the vector may be, for example and without limitation, a mammalian expression vector, a bacterial expression vector etc.

The invention also relates to cells comprising or expressing the antibody or antigen binding fragment of the present invention or comprising the nucleic acids or vectors of the present invention.

In yet a further aspect, the present invention provides a kit comprising a vial or vials which may comprise, for example, the humanized antibody described herein, the hybrid antibody described herein, the antigen binding fragment described herein, the isolated antibody described herein, the isolated nucleic acid described herein or the vector described herein.

In another aspect, the present invention relates to a pharmaceutical composition which may comprise, for example, the humanized antibody described herein, the hybrid antibody described herein, the antigen binding fragment described herein or the isolated antibody described herein and a pharmaceutically acceptable carrier.

Yet another aspect of the invention relates to a combination therapy which includes the pharmaceutical composition described herein and a chemotherapeutic agent.

Also encompassed herewith are methods of producing humanized or hybrid anti-clusterin antibodies or antigen binding fragments as well as method of treating a disease associated with clusterin expression or secretion using the humanized or hybrid anti-clusterin antibodies or antigen binding fragments.

Further scope, applicability and advantages of the present invention will become apparent from the non-restrictive detailed description given hereinafter. It should be understood, however, that this detailed description, while indicating exemplary embodiments of the invention, is given by way of example only, with reference to the accompanying drawings.

BRIEF DESCRIPTION OF THE DRAWINGS

FIG. 3. Kinetic analysis of 16B5 murine and humanized anti-clusterin antibodies.

FIG. 8. Sequence alignment of the mouse 16B5, humanized 21B12 and the selected human framework (NCBI database links provided). Kabat numbering is shown at the top. CDRs are highlighted. Candidate residues for back-mutations are highlighted below the sequence alignment according to proximity to CDRs (5: within 5 Angstrom), surface exposure (B: Buried), and contact with the pairing variable domain.

FIG. 9. Kinetic analysis of the 21B12 murine and humanized anti-clusterin antibodies.

FIG. 15. Shows the region of homology between human clusterin (NP_001822: SEQ ID NO.:48) and murine clusterin (NP_038520: SEQ ID NO.:54).

DETAILED DESCRIPTION OF THE INVENTION

Figure 1:
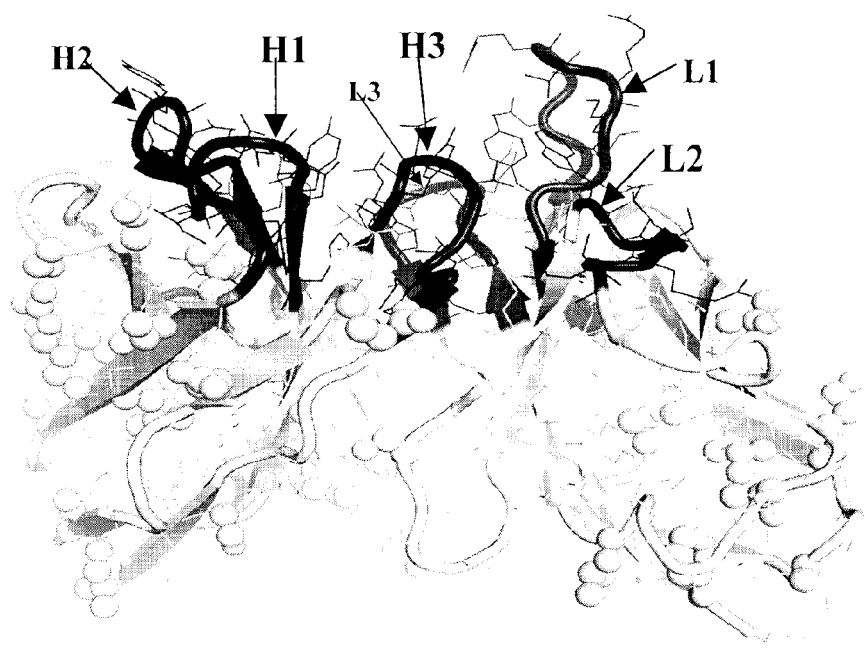
FIG. 1. Homology 3D model of the variable region of the mouse 16B5 anti-clusterin antibody. CDRs are labeled (L1, L2, L3 in the light chain, and H1, H2, H3 in the heavy chain). Mouse framework residues replaced by human framework residues are indicated as sphere models.

The present invention relates in one aspect thereof to antibodies which are capable of specific binding to clusterin and which comprise a humanized light chain variable region and/or a humanized heavy chain variable region.

The sequence of human clusterin may be found at RefSeq accession number; NM_001831.2 (protein id.=NP_001822) whereas the sequence of murine clusterin may be found at RefSeq accession number; NM_013492.2 (protein id.=NP_038520).

The antibodies or antigen binding fragment of the present invention may be able to bind to the murine and/or the human form of clusterin. The antibodies or antigen binding fragment of the present invention may also be able to bind naturally occurring variant as well as synthetic variants of clusterin having for example at least 75% (e.g., 80%, 85%, 90%, 95%, 99%) amino acid identity with human or murine clusterin.

The present invention therefore provides a humanized antibody of a non-human parent antibody that is capable of specific binding to clusterin or an antigen binding fragment thereof as well as hybrid antibodies and antigen binding fragments thereof.

In accordance with an embodiment of the invention, the humanized or hybrid antibody may inhibit (lower) the growth of a tumor cell expressing or secreting clusterin.

In accordance with a further embodiment of the invention, the humanized or hybrid antibody may reduce the volume of a tumor comprising cells expressing or secreting clusterin.

In accordance with another embodiment of the invention, the humanized or hybrid antibody may inhibit (lower) migration or invasion of a tumor cell expressing or secreting clusterin.

Therefore in accordance with yet another embodiment of the invention, the humanized or hybrid antibody may inhibit (lower) metastasis occurring from a tumor cell expressing or secreting clusterin.

In another aspect, the present invention relates to a method for reducing the volume of a tumor comprising clusterin-expressing cells which may comprise administering an anti-clusterin antibody (a polyclonal antibody, a monoclonal antibody, a chimeric antibody, a humanized antibody, an isolated human antibody, a hybrid antibody or a fragment thereof) to a mammal in need. The method more particularly contemplates administering a chimeric, humanized or hybrid antibody.

In one embodiment, the hybrid antibody or fragment thereof may comprise, for example, a light chain variable region of a non-human antibody and a heavy chain variable region of a humanized antibody.

In another embodiment, the hybrid antibody or fragment thereof may comprise, for example, a light chain variable region of a non-human antibody and a heavy chain variable region of a humanized antibody.

The term "antibody" refers to intact antibody, monoclonal, (fully or partially) humanized, hybrid, chimeric or polyclonal antibodies as well as isolated human antibodies. The term "antibody" also encompasses multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "humanized antibody" refers to an antibody comprising from one to six CDR(s) comprising non-human CDR amino acid residues and substantial portion of its heavy chain and/or light chain framework region that is from the human antibody repertoire. In some instance, the totality of the heavy chain and/or light chain framework region of the humanized antibody may be identical to those of an antibody that is encoded (encodable) by the human antibody repertoire (a natural human antibody). In other instances, the heavy chain and/or light chain framework region of the humanized antibody may comprises from one to thirty amino acids from the non-human antibody which is sought to be humanized and the remaining portion being of from a natural human antibody. In additional instances, the humanized antibody may comprise from 1 to 6 fully non-human CDRs and often the six CDRs are fully non-human. In yet other instances, a "humanized antibody" may comprise a constant region that is or human or other origin (from a mammal).

The term "hybrid antibody" refers to an antibody comprising one of its heavy or light chain variable region (its heavy or light chain) that is humanized or from a natural human antibody (having affinity for clusterin) while the other of the heavy or light chain variable region (the heavy or light chain) remains non-human.

The term "chimeric antibody" refers to an antibody having non-human variable region(s) and human constant region.

The term "natural human antibody" refers to an antibody that is encoded (encodable) by the human antibody repertoire, i.e., germline sequence.

As used herein, an isolated human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. An isolated human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The term "antigen-binding fragment", as used herein, refers to one or more fragments of an antibody that retain the ability to bind to an antigen. It has been shown that the antigen-binding function of an antibody can be performed by fragments of an intact antibody.

Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, and (v) a dAb fragment (Ward et al., (1989) Nature 341:544-546), which consists of a $V_H$ domain. Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. However, the FRs often play a role in the proper positioning and alignment in three dimensions of the CDRs for optimal antigen binding.

A humanized or hybrid antibody of the present invention may comprise a heavy chain variable region which may include non-human complementarity determining region amino acid residues and human framework region amino acid residues of a natural human antibody and a complementary light chain.

A humanized or hybrid antibody of the present invention may comprise a light chain variable region which may include non-human complementarity determining region amino acid residues and human framework region amino acid residues of a natural human antibody and a complementary heavy chain.

A humanized or hybrid antibody of the present invention may inhibit metastasis, tumor cell migration or invasion or may inhibit the growth of clusterin-expressing cells including, for example, carcinoma cells. In fact, the Applicant came to the unexpected discovery that anti-clusterin antibodies including the humanized or hybrid antibodies of the present invention reduce tumor volume in vivo. Alternatively, the humanized or hybrid antibody of the present invention may be used to detect clusterin-expressing cells.

The natural human antibody that is selected for humanization of the non-human parent antibody may comprise a variable region having a three-dimensional structure similar to that of (superimposable to) a (modeled) variable region of the non-human parent antibody. As such, the humanized or hybrid antibody has a greater chance of having a three-dimensional structure similar to that of the non-human parent antibody.

The humanized antibody of the present invention has a high affinity for clusterin. In fact, it has been shown herein that the humanized antibody binds to recombinant monomeric clusterin with an affinity of $4.49 \times 10^{-9}$ M$\pm 8.5 \times 10^{-10}$ or better.

In accordance with the present invention, the human framework region amino acid residues of the humanized or hybrid antibody light chain are from a natural human antibody light chain framework region. The light chain framework region of the natural human antibody selected for humanization purposes, may have, for example, at least 70% identity with a light chain framework region of the non-human parent antibody. Preferably, the natural human antibody selected for humanization purposes may have the same or substantially the same number of amino acids in its light chain complementarity determining region to that of a light chain complementarity determining region of the non-human parent antibody.

In other embodiments of the invention, the human framework region amino acid residues of the humanized or hybrid antibody light chain are from a natural human antibody light chain framework region having at least 75, 80, 83% identity (or more) with the light chain framework region of the non-human parent antibody.

Also in accordance with the present invention, the human framework region amino acid residues of the humanized or hybrid antibody heavy chain are from a natural human antibody heavy chain framework region having at least 70% identity with a heavy chain framework region of the non-human parent antibody. Preferably, the natural human antibody selected for humanization purposes may have the same or substantially the same number of amino acids in its heavy chain complementarity determining region to that of a heavy chain complementarity determining region of the non-human parent antibody.

In other embodiments of the invention, the human framework region amino acid residues of the humanized or hybrid antibody heavy chain are from a natural human antibody heavy chain framework region having at least 73, 75, 80% identity with the heavy chain framework region of the non-human parent antibody.

In an embodiment of the invention, the heavy chain variable region of the humanized or hybrid antibody may thus comprise at least one non-human complementarity determining region.

Alternatively, in other embodiments of the invention, the heavy chain variable region of the humanized or hybrid antibody may comprise at least two non-human complementarity determining regions or even three non-human complementarity determining regions.

In an additional embodiment of the invention, the light chain variable region may comprise at least one non-human complementarity determining region.

Alternatively, in yet additional embodiments of the invention, the light chain variable region comprise at least two non-human complementarity determining regions or even three non-human complementarity determining regions.

The humanized antibody may thus advantageously comprise all six CDRs of the non-human antibody. In the case of a divalent humanized antibody, all twelve CDRs may be from the non-human antibody.

Clusterin-expressing cells which may be detected by a humanized or hybrid antibody comprises carcinoma cells. The humanized or hybrid antibody may also be used to inhibit the growth of clusterin-expressing carcinoma cells and especially, human carcinoma cells.

Several types of human carcinoma cells have been shown to express or secrete clusterin, amongst which, cells of endometrial carcinoma, of breast carcinoma, of hepatocellular carcinoma, of prostate carcinoma, of renal cell carcinoma, of ovarian carcinoma, of colorectal cancer, of pancreatic carcinoma, etc.

An exemplary embodiment of the invention includes, for example, the humanized or hybrid antibody comprising human framework region amino acid residues of the natural human antibody heavy chain as described herein and heavy chain CDR selected from the group consisting of a CDRH1 having an amino acid sequence of SEQ ID NO.:1, a CDRH2 having an amino acid sequence of SEQ ID NO.:2 and a CDRH3 having an amino acid sequence of SEQ ID NO.:3 and combination thereof or heavy chain CDR selected from the group consisting of a CDRH1 having an amino acid sequence of SEQ ID NO.:11, a CDRH2 having an amino acid sequence of SEQ ID NO.:12 and a CDRH3 having an amino acid sequence of SEQ ID NO.:13 and combination thereof.

In another exemplary embodiment, the humanized or hybrid antibody may comprise human framework region amino acid residues of the natural human antibody heavy chain as described herein and at least two heavy chain CDRs selected from the group consisting of a CDRH1 having an amino acid sequence of SEQ ID NO.:1, a CDRH2 having an amino acid sequence of SEQ ID NO.:2 and a CDRH3 having an amino acid sequence of SEQ ID NO.:3 or at least two heavy chain CDRs selected from the group consisting of a CDRH1 having an amino acid sequence of SEQ ID NO.:11, a CDRH2 having an amino acid sequence of SEQ ID NO.:12 and a CDRH3 having an amino acid sequence of SEQ ID NO.:13 and combination thereof.

Alternatively, in another exemplary embodiment, the humanized or hybrid antibody of the present invention may comprise human framework region amino acid residues of the natural human antibody heavy chain as described herein and a CDRH1 having an amino acid sequence of SEQ ID NO.:1, a CDRH2 having an amino acid sequence of SEQ ID NO.:2 and a CDRH3 having an amino acid sequence of SEQ ID NO.:3 or a CDRH1 having an amino acid sequence of SEQ ID NO.:11, a CDRH2 having an amino acid sequence of SEQ ID NO.:12 and a CDRH3 having an amino acid sequence of SEQ ID NO.:13.

In a more specific embodiment of the invention, the humanized or hybrid antibody (or any antigen binding fragment derived therefrom) may comprise a light chain variable region comprising SEQ ID NO.:26 (h16B5 VL consensus 1): DIVMXQSPXSLAVSXGEXXTXX-CKSSQSLLNSRTRKNYLAWYQQKPGQXPKLLIY WASTRESGVPDRFXGSGSGTDFTLTISSXQAEDX-AVYYCKQSYNLWTFGXGTKLEX K; wherein at least one of the amino acid identified by X is an amino acid substitution in comparison with a corresponding amino acid in the polypeptide set forth in SEQ ID NO.:25 (the murine 16B5 VL). The amino acid substitution may be, for example conservative or non-conservative. In accordance with the invention, the amino acid substitution may be conservative.

The humanized or hybrid antibody (or any antigen binding fragment derived therefrom) may comprise a light chain variable region comprising SEQ ID NO.:27 (16B5 VL consensus2):

DIVMX$_{a1}$QSPX$_{a2}$SLAVSX$_{a3}$GEX$_{a4}$X$_{a5}$TX$_{a6}$X$_{a7}$CKSSQSLLNSRTRKNYLA

WYQQKPGQX$_{a8}$PKLLIYWASTRESGVPDRFX$_{a9}$GSGSGTDFTLTISSX$_{a10}$

QAEDX$_{a11}$AVYYCKQSYNLWTFGX$_{a12}$GTKLEX$_{a13}$K;

Wherein X$_{a1}$ may be a neutral hydrophilic amino acid such as for example, T or S;

Wherein X$_{a2}$ may be for example D or S;

Wherein X$_{a3}$ may be an hydrophobic amino acid such as for example, L or A;

Wherein X$_{a4}$ may be a basic amino acid such as for example R or K;

Wherein X$_{a5}$ may be an hydrophobic amino acid such as for example A or V;

Wherein X$_{a6}$ may be an hydrophobic amino acid as for example I or M;

Wherein X$_{a7}$ may be for example N or S;

Wherein X$_{a8}$ may be for example P or S;

Wherein X$_{a9}$ may be a neutral hydrophilic amino acid such as for example S or T;

Wherein X$_{a10}$ may be an hydrophobic amino acid such as for example L or V;

Wherein X$_{a11}$ may be an hydrophobic amino acid such as for example V or L;

Wherein X$_{a12}$ may be for example Q or G;

Wherein X$_{a13}$ may be for example I or F and;

wherein the light chain variable region may comprise at least one of the above amino acid substitution in comparison with SEQ ID NO.:25.

The humanized or hybrid antibody (or any antigen binding fragment derived therefrom) may comprise a light chain variable region comprising SEQ ID NO.:28 (16B5 VL consensus3):

DIVMX$_{a1}$QSPX$_{a2}$SLAVSX$_{a3}$GEX$_{a4}$X$_{a5}$TX$_{a6}$X$_{a7}$CKSSQSLLNSRTRKNYLA

WYQQKPGQX$_{a8}$PKLLIYWASTRESGVPDRFX$_{a9}$GSGSGTDFTLTISSX$_{a10}$

QAEDX$_{a11}$AVYYCKQSYNLWTFGX$_{a12}$GTKLEX$_{a13}$K;

Wherein X$_{a1}$ may be for example, T or S;

Wherein X$_{a2}$ may be for example D or S;

Wherein X$_{a3}$ may be for example, L or A;

Wherein X$_{a4}$ may be for example R or K;

Wherein X$_{a5}$ may be for example A or V;

Wherein X$_{a6}$ may be for example I or M;

Wherein X$_{a7}$ may be for example N or S;

Wherein X$_{a8}$ may be for example P or S;

Wherein X$_{a9}$ may be for example S or T;

Wherein X$_{a10}$ may be for example L or V;

Wherein X$_{a11}$ may be for example V or L;

Wherein X$_{a12}$ may be for example Q or G;

Wherein X$_{a13}$ may be for example I or F and;

wherein the light chain variable region may comprise at least one of the above amino acid substitution in comparison with SEQ ID NO.:25.

In another more specific embodiment of the invention, the humanized or hybrid antibody (or any antigen binding fragment derived therefrom) may comprise a heavy chain variable region comprising SEQ ID NO.:30 (16B5 VH consensus1);

XVQLXQSGAEXXKPGAXVXXSCXXSGFNIKDIYMHWVXQXPXXGLEWXG

RIDPAYGNTKYDPKFQGXXTITADTSXXTAYXXLSSLXSEDTAVYYCAR

RYDTAMDYWGQGTXVTVSS;

wherein at least one of the amino acid identified by X is an amino acid substitution in comparison with a corresponding amino acid in the polypeptide set forth in SEQ ID NO.:29 (the murine 16B5 VH). The amino acid substitution may be, for example conservative or non-conservative. In accordance with the invention, the amino acid substitution may be conservative.

The humanized or hybrid antibody (or any antigen binding fragment derived therefrom) may comprise a heavy chain variable region comprising SEQ ID NO.:31 (16B5 VH consensus2):

$X_{b1}$VQL$X_{b2}$QSGAE$X_{b3}X_{b4}$KPGA$X_{b5}$V$X_{b6}X_{b7}$SC$X_{b8}X_{b9}$SGFNIKDIYMHWV$X_{b10}$

Q$X_{b11}$P$X_{b12}X_{b13}$GLEW$X_{b14}$GRIDPAYGNTKYDPKFQGX$_{b15}X_{b16}$TITAD-TS$X_{b17}$ $X_{b18}$TAY$X_{b19}X_{b20}$LSSL$X_{b21}$SEDTAVYYCARRYDTAMDYWGQGT$X_{b22}$VTVSS;

Wherein $X_{b1}$ may be for example Q or E;
Wherein $X_{b2}$ may be for example V or Q;
Wherein $X_{b3}$ may be an hydrophobic amino acid such as for example V or L;
Wherein $X_{b4}$ may be for example K or V;
Wherein $X_{b5}$ may be a neutral hydrophilic amino acid such as for example T or S;
Wherein $X_{b6}$ may be a basic amino acid such as for example K or R;
Wherein $X_{b7}$ may be an hydrophobic amino acid such as for example I or L;
Wherein $X_{b8}$ may be for example K or T;
Wherein $X_{b9}$ may be for example V or T;
Wherein $X_{b10}$ may be a basic amino acid such as for example Q or K;
Wherein $X_{b11}$ may be for example A or R;
Wherein $X_{b12}$ may be for example G or E;
Wherein $X_{b13}$ may be a basic amino acid such as for example K or Q;
Wherein $X_{b14}$ may be an hydrophobic amino acid such as for example M or I;
Wherein $X_{b15}$ may be a basic amino acid such as for example R or K;
Wherein $X_{b16}$ may be an hydrophobic amino acid such as for example V or A;
Wherein $X_{b17}$ may be a neutral hydrophilic amino acid such as for example T or S;
Wherein $X_{b18}$ may be for example D or N;
Wherein $X_{b19}$ may be an hydrophobic amino acid such as for example M or L;
Wherein $X_{b20}$ may be for example E or Q;
Wherein $X_{b21}$ may be for example R or T;
Wherein $X_{b22}$ may be as for example L or S and;
wherein the heavy chain variable region may comprise at least one of the above amino acid substitution in comparison with SEQ ID NO.:29.

The humanized or hybrid antibody (or any antigen binding fragment derived therefrom) may comprise a heavy chain variable region comprising SEQ ID NO.:32 (16B5 VH consensus3):

$X_{b1}$VQL$X_{b2}$QSGAE$X_{b3}X_{b4}$KPGA$X_{b5}$V$X_{b6}X_{b7}$SC$X_{b8}X_{b9}$SGFNIKDIYMHW-V$X_{b10}$

Q$X_{b11}$P$X_{b12}X_{b13}$GLEW$X_{b14}$GRIDPAYGNTKYDPKFQGX$_{b15}X_{b16}$TITAD-TS$X_{b17}$ $X_{b18}$TAY$X_{b19}X_{b20}$LSSL$X_{b21}$SEDTAVYYCARRYDTAMDYWGQGT$X_{b22}$VTVSS;

Wherein $X_{b1}$ may be for example Q or E;
Wherein $X_{b2}$ may be for example V or Q;
Wherein $X_{b3}$ may be for example V or L;
Wherein $X_{b4}$ may be for example K or V;
Wherein $X_{b5}$ may be for example T or S;
Wherein $X_{b6}$ may be for example K or R;
Wherein $X_{b7}$ may be for example I or L;
Wherein $X_{b8}$ may be for example K or T;
Wherein $X_{b9}$ may be for example V or T;
Wherein $X_{b10}$ may be for example Q or K;
Wherein $X_{b11}$ may be for example A or R;
Wherein $X_{b12}$ may be for example G or E;
Wherein $X_{b13}$ may be for example K or Q;
Wherein $X_{b14}$ may be for example M or I;
Wherein $X_{b15}$ may be for example R or K;
Wherein $X_{b16}$ may be for example V or A;
Wherein $X_{b17}$ may be for example T or S;
Wherein $X_{b18}$ may be for example D or N;
Wherein $X_{b19}$ may be for example M or L;
Wherein $X_{b20}$ may be for example E or Q;
Wherein $X_{b21}$ may be for example R or T;
Wherein $X_{b22}$ may be for example L or S and;
wherein the heavy chain variable region may comprise at least one of the above amino acid substitution in comparison with SEQ ID NO.:29.

In an additional specific embodiment of the invention the humanized or hybrid antibody (or any antigen binding fragment derived therefrom) may comprise a light chain variable region comprising SEQ ID NO.:34 (21B12 VL consensus1):

DIVM$X_c$QSP$X$SLAVSXGEXXTXXCKSSQSLLYSSNQKNYLAWYQQXPG

QXPKLLIYWASTRESGVPDRFXGSGSGTDFTLTISSXXAEDXAVYYC

QQYYIYPRTFGXGTKLEIK;

wherein at least one of the amino acid identified by X is an amino acid substitution in comparison with a corresponding amino acid in the polypeptide set forth in SEQ ID NO.:33 (the murine 21B12 VL). The amino acid substitution may be, for example conservative or non-conservative. In accordance with the invention, the amino acid substitution may be conservative.

The humanized or hybrid antibody (or any antigen binding fragment derived therefrom) may comprise a light chain variable region comprising SEQ ID NO.:35 (21B12 VL consensus2):

DIVM$X_{c1}$QSP$X_{c2}$SLAVS$X_{c3}$GE$X_{c4}X_{c5}$T$X_{c6}X_{c7}$CKSSQSLLYSSNQKNYLAW

YQQ$X_{c8}$PGQ$X_{c9}$PKLLIYWASTRESGVPDRF$X_{c10}$GSGSGTDFTLTISS$X_{c11}$ $X_{c12}$AED$X_{c13}$AVYYCQQYYIYPRTFG$X_{c14}$GTKLEIK;

Wherein $X_{c1}$ may be a neutral hydrophilic amino acid such as for example T or S;
Wherein $X_{c2}$ may be for example D or S;
Wherein $X_{c3}$ may be an hydrophobic amino acid such as for example L or V;

Wherein $X_{c4}$ may be a basic amino acid such as for example R or K;

Wherein $X_{c5}$ may be an hydrophobic amino acid such as for example A or V;

Wherein $X_{c6}$ may be an hydrophobic amino acid such as for example I or M;

Wherein $X_{c7}$ may be for example N or S;

Wherein $X_{c8}$ may be a basic amino acid such as for example K or R;

Wherein $X_{c9}$ may be for example P or S;

Wherein $X_{c10}$ may be a neutral hydrophilic amino acid such as for example S or T;

Wherein $X_{c11}$ may be an hydrophobic amino acid such as for example L or V;

Wherein $X_{c12}$ may be a basic amino acid such as for example Q or K;

Wherein $X_{c13}$ may be an hydrophobic amino acid such as for example V or L;

Wherein $X_{c14}$ may be for example Q or G and;

wherein the light chain variable region may comprise at least one of the above amino acid substitution in comparison with SEQ ID NO.:33.

The humanized or hybrid antibody (or any antigen binding fragment derived therefrom) may comprise a light chain variable region comprising SEQ ID NO.:36 (21B12 VL consensus3):

DIVMX$_{c1}$QSPX$_{c2}$SLAVSX$_{c3}$GEX$_{c4}$X$_{c5}$TX$_{c6}$X$_{c7}$CKSSQSLLYSSNQKNYLAW

YQQX$_{c8}$PGQX$_{c9}$PKLLIYWASTRESGVPDRFX$_{c10}$GSGSGTDFTLTISSX$_{c11}$

X$_{c12}$AEDX$_{c13}$AVYYCQQYYIYPRTFGX$_{c14}$GTKLEIK;

Wherein $X_{c1}$ may be T or S;
Wherein $X_{c2}$ may be for example D or S;
Wherein $X_{c3}$ may be L or V;
Wherein $X_{c4}$ may be R or K;
Wherein $X_{c5}$ may be for example A or V;
Wherein $X_{c6}$ may be for example I or M;
Wherein $X_{c7}$ may be for example N or S;
Wherein $X_{c8}$ may be for example K or R;
Wherein $X_{c9}$ may be for example P or S;
Wherein $X_{c10}$ may be for example S or T;
Wherein $X_{c11}$ may be for example L or V;
Wherein $X_{c12}$ may be for example Q or K;
Wherein $X_{c13}$ may be for example V or L;
Wherein $X_{c14}$ may be for example Q or G and;

wherein the light chain variable region may comprise at least one of the above amino acid substitution in comparison with SEQ ID NO.:33.

In a further exemplary embodiment of the invention, the humanized or hybrid antibody (or any antigen binding fragment derived therefrom) may comprise a heavy chain variable region comprising SEQ ID NO.:38 (21B12 VH consensus1):

QXQLVQSGXELKKPGXXVKXSCKASGYTFTNYGMHWVXQAPGXGLXWMG

WINTYTGEPTYADDFKGRFXFSLXTSXSTAYLQIXXLKXEDTAXYXCAR

DGFLYFFDYWGQGTXXTVSS;

wherein at least one of the amino acid identified by X is an amino acid substitution in comparison with a corresponding amino acid in the polypeptide set forth in SEQ ID NO.:37 (the murine 21B12 VH). The amino acid substitution may be, for example conservative or non-conservative. In accordance with the invention, the amino acid substitution may be conservative.

The humanized or hybrid antibody (or any antigen binding fragment derived therefrom) may comprise a heavy chain variable region comprising SEQ ID NO.:39 (21B12 VH consensus2):

QX$_{d1}$QLVQSGX$_{d2}$ELKKPGX$_{d3}$X$_{d4}$VKX$_{d5}$SCKASGYTFTNYGMHWVX$_{d6}$

QAPGX$_{d7}$GLX$_{d8}$WMGWINTYTGEPTYADDFKGRFX$_{d9}$FSLX$_{d10}$TSX$_{d11}$

STAYLQIX$_{d12}$X$_{d13}$LKX$_{d14}$EDTAX$_{d15}$YX$_{d16}$CARDGFLYFFDYWGQGTX$_{d17}$

X$_{d18}$TVSS;

Wherein $X_{d1}$ may be an hydrophobic amino acid such as for example V or I;
Wherein $X_{d2}$ may be for example S or P;
Wherein $X_{d3}$ may be for example A or E;
Wherein $X_{d4}$ may be a neutral hydrophilic amino acid such as for example S or T;
Wherein $X_{d5}$ may be an hydrophobic amino acid such as for example V or I;
Wherein $X_{d6}$ may be a basic amino acid such as for example R or K;
Wherein $X_{d7}$ may be a basic amino acid such as for example Q or K;
Wherein $X_{d8}$ may be for example E or K;
Wherein $X_{d9}$ may be an hydrophobic amino acid such as for example V or A;
Wherein $X_{d10}$ may be an acidic amino acid such as for example D or E;
Wherein $X_{d11}$ may be an hydrophobic amino acid such as for example V or A;
Wherein $X_{d12}$ may be for example S or N;
Wherein $X_{d13}$ may be for example S or N;
Wherein $X_{d14}$ may be for example A or N;
Wherein $X_{d15}$ may be for example V or T;
Wherein $X_{d16}$ may be an aromatic amino acid such as for example Y or F;
Wherein $X_{d17}$ may be for example L or T;
Wherein $X_{d18}$ may an hydrophobic amino acid such as for example V or L and;

wherein the heavy chain variable region may comprise at least one of the above amino acid substitution in comparison with SEQ ID NO.:37.

The humanized or hybrid antibody (or any antigen binding fragment derived therefrom) may comprise a heavy chain variable region comprising SEQ ID NO.:40 (21B12 VH consensus3):

QX$_{d1}$QLVQSGX$_{d2}$ELKKPGX$_{d3}$X$_{d4}$VKX$_{d5}$SCKASGYTFTNYGMHWVX$_{d6}$QAPGX$_{d7}$

GLX$_{d8}$WMGWINTYTGEPTYADDFKGRFX$_{d9}$FSLX$_{d10}$TSX$_{d11}$STAYLQIX$_{d12}$X$_{d13}$

LKX$_{d14}$EDTAX$_{d15}$YX$_{d16}$CARDGFLYFFDYWGQGTX$_{d17}$X$_{d18}$TVSS;

Wherein $X_{d1}$ may be for example V or I;
Wherein $X_{d2}$ may be for example S or P;
Wherein $X_{d3}$ may be for example A or E;
Wherein $X_{d4}$ may be for example S or T:
Wherein $X_{d5}$ may be for example V or I;
Wherein $X_{d6}$ may be for example R or K;
Wherein $X_{d7}$ may be for example Q or K;
Wherein $X_{d8}$ may be for example E or K;
Wherein $X_{d9}$ may be for example V or A;
Wherein $X_{d10}$ may be for example D or E;

Wherein $X_{d11}$ may be for example V or A;
Wherein $X_{d12}$ may be for example S or N;
Wherein $X_{d13}$ may be for example S or N;
Wherein $X_{d14}$ may be for example A or N;
Wherein $X_{d15}$ may be for example V or T;
Wherein $X_{d16}$ may be for example Y or F;
Wherein $X_{d17}$ may be for example L or T;
Wherein $X_{d18}$ may be for example V or L and;
wherein the heavy chain variable region may comprise at least one of the above amino acid substitution in comparison with SEQ ID NO.:37.

In a more specific embodiment, the humanized or hybrid antibody may comprise a heavy chain variable region having an amino acid sequence of SEQ ID NO.:7 or SEQ ID NO.:17.

Yet a more specific embodiment of the invention includes a humanized or hybrid antibody which may comprise a heavy chain having an amino acid sequence of SEQ ID NO.:9 or SEQ ID NO.:19.

The humanized or hybrid antibody of the present invention may have a heavy chain or heavy chain variable region as specified herein and a complementary light chain or light chain variable region.

On the other hand, the humanized or hybrid antibody of the present invention may have a light chain or light chain variable region as specified herein and a complementary heavy chain or heavy chain variable region.

The humanized or hybrid antibody of the present invention may thus comprise human framework region amino acid residues of the natural human antibody light chain as described herein and a light chain CDR selected, for example, from the group consisting of a CDRL1 having an amino acid sequence of SEQ ID NO.:4, a CDRL2 having an amino acid sequence of SEQ ID NO.:5 and a CDRL3 having an amino acid sequence of SEQ ID NO.:6 or heavy chain CDR selected from the group consisting of a CDRL1 having an amino acid sequence of SEQ ID NO.:14, a CDRL2 having an amino acid sequence of SEQ ID NO.:15 and a CDRL3 having an amino acid sequence of SEQ ID NO.:16 and combination thereof.

In a further embodiment, the humanized or hybrid antibody may comprise human framework region amino acid residues of the natural human antibody light chain as described herein and at least two light chain CDRs selected from the group consisting of a CDRL1 having an amino acid sequence of SEQ ID NO.:4, a CDRL2 having an amino acid sequence of SEQ ID NO.:5 and a CDRL3 having an amino acid sequence of SEQ ID NO.:6 or at least two heavy chain CDRs selected from the group consisting of a CDRL1 having an amino acid sequence of SEQ ID NO.:14, a CDRL2 having an amino acid sequence of SEQ ID NO.:15 and a CDRL3 having an amino acid sequence of SEQ ID NO.: 16 and combination thereof.

In yet a further embodiment, the humanized or hybrid antibody may comprise human framework region amino acid residues of the natural human antibody light chain as described herein and a CDRL1 having an amino acid sequence of SEQ ID NO.:4, a CDRL2 having an amino acid sequence of SEQ ID NO.:5 and a CDRL3 having an amino acid sequence of SEQ ID NO.:6 or a CDRL1 having an amino acid sequence of SEQ ID NO.:14, a CDRL2 having an amino acid sequence of SEQ ID NO.:15 and a CDRL3 having an amino acid sequence of SEQ ID NO.:16 and combination thereof.

In a more particular embodiment, the humanized or hybrid antibody may comprise a light chain variable region having an amino acid sequence of SEQ ID NO.:8 or SEQ ID NO.:18.

In an even more particular embodiment, the humanized or hybrid antibody of the present invention may comprise a light chain having an amino acid sequence of SEQ ID NO.:10 or SEQ ID NO.:20.

Other specific embodiments of the invention encompass a humanized antibody having a heavy chain variable region having an amino acid sequence of SEQ ID NO.:7 or SEQ ID NO.:17 and a light chain variable region having an amino acid sequence of SEQ ID NO.:8 or SEQ ID NO.:18.

An additional specific embodiment of the invention encompass a humanized antibody having a heavy chain having an amino acid sequence of SEQ ID NO.:9 and a light chain having an amino acid sequence of SEQ ID NO.:10.

Yet, an additional specific embodiment of the invention encompass a humanized antibody having a heavy chain having an amino acid sequence of SEQ ID NO.:19 and a light chain having an amino acid sequence of SEQ ID NO.:20.

The present invention relates in a further aspect to an antibody or antigen binding fragment thereof which may be capable of specific binding to clusterin and which may be selected from the group consisting of:

an antibody or antigen binding fragment thereof which may have a light chain variable region at least 80% identical (e.g., 85%, 90%, 95%, 99%) to SEQ ID NO.:25 and/or a heavy chain variable region at least 80% identical (e.g., 85%, 90%, 95%, 99%) to SEQ ID NO.:29 wherein the antibody or antigen binding fragment thereof may comprise, for example, at least one amino acid substitution in comparison with SEQ ID NO.:25 or SEQ ID NO.:29 and wherein the amino acid substitution may be, for example, outside of a complementarity determining region (CDR) and;

an antibody or antigen binding fragment thereof which may have a light chain variable region at least 80% identical (e.g., 85%, 90%, 95%, 99%) to SEQ ID NO.:33 and/or a heavy chain variable region at least 80% identical (e.g., 85%, 90%, 95%, 99%) to SEQ ID NO.:37 wherein the antibody or antigen binding fragment thereof may comprise at least one amino acid substitution in comparison with SEQ ID NO.:33 or SEQ ID NO.:37 and wherein the amino acid substitution may be, for example, outside of a complementarity determining region (CDR).

In accordance with the present invention, the at least one amino acid substitution may be, for example, in the light chain variable region.

In accordance with the present invention, the at least one amino acid substitution may be, for example, in the heavy chain variable region.

The amino acid substitution may be conservative or non-conservative. In a more specific embodiment, the amino acid substitution may be conservative.

In accordance with an embodiment of the invention, the antibodies and antigen binding fragments of the present invention bind human clusterin. In accordance with another embodiment of the invention, the antibodies and antigen binding fragments of the present invention bind murine clusterin. The antibodies and antigen binding fragment of the present invention may also bind a naturally occurring or synthetic variant of murine of human clusterin. Such variant may have, for example, at least 75% amino acid sequence identity with human clusterin or with murine clusterin.

The CDRs of SEQ ID NO.:29 (identical to those of SEQ ID NOs. 30, 31, 32 and 7) were identified using the Kabat and Chothia definitions. The corresponding CDR sequences are identified herein as follow; the CDR1 of the heavy chain variable region corresponds to SEQ ID NO.:1, the CDR2 of the heavy chain variable region corresponds to SEQ ID NO.:2 and the CDR3 of the heavy chain variable region corresponds to SEQ ID NO.:3.

Shorter versions of SEQ ID NOs.:1, 2 and 3 were presented in international application No. PCT/CA2006/001505 filed on Sep. 13, 2006 (i.e., the 1505 appl.) and published under No. WO2007/030930. In this patent application, the CDRs of SEQ ID NO.:29 (corresponding to SEQ ID NO.:23 in the '1505 appl.) were identified with the IMGT/V quest software that implements the IMGT definition. The corresponding sequences are identified herein as follow; the CDR1 of the heavy chain variable region corresponds to SEQ ID NO.:44, the CDR2 of the heavy chain variable region corresponds to SEQ ID NO.:45 and the CDR3 of the heavy chain variable region corresponds to SEQ ID NO.:46.

As used herein the term "amino acid substitution . . . outside of a complementarity determining region (CDR)" with respect to SEQ ID NO.:29 generally refers to amino acids (outside of) surrounding SEQ ID NOs.:1, 2 and 3. In some embodiments this term may alternatively refer to amino acids (outside of) surrounding SEQ ID NOs.:44, 45 and 46.

The CDRs of SEQ ID NO.:25 (identical to those of SEQ ID NOs. 26, 27, 28 and 8) were identified using the Kabat and Chothia definitions. The corresponding CDR sequences are identified as follow; the CDR1 of the light chain variable region corresponds to SEQ ID NO.:4, the CDR2 of the light chain variable region corresponds to SEQ ID NO.:5 and the CDR3 of the light chain variable region corresponds to SEQ ID NO.:6.

Shorter versions of SEQ ID NOs. 4, 5 and 6 were presented in international application No. PCT/CA2006/001505 filed on Sep. 13, 2006 (i.e., the 1505 appl.) and published under No. WO2007/030930. In this patent application, the CDRs of SEQ ID NO.:25 (corresponding to SEQ ID NO.:12 in the '1505 appl.) were identified with the IMGT/V quest software that implements the IMGT definition. The corresponding sequences are identified herein as follow; the CDR1 of the light chain variable region corresponds to SEQ ID NO.:47, the CDR2 of the light chain variable region corresponds to amino acid sequence "WAS" and the CDR3 of the light chain variable region corresponds to SEQ ID NO.:49.

As used herein the term "amino acid substitution . . . outside of a complementarity determining region (CDR)" with respect to SEQ ID NO.:25 generally refers to amino acids (outside of) surrounding SEQ ID NOs.:4, 5 and 6. In some embodiments this term may alternatively refer to amino acids (outside of) surrounding SEQ ID NOs.:47, the CDR2 of the light chain variable region and 49.

The CDRs of SEQ ID NO.:37 (identical to those of SEQ ID NOs. 38, 39, 40 and 17) were identified using the Kabat and Chothia definitions. The corresponding CDR sequences are identified herein as follow; the CDR1 of the heavy chain variable region corresponds to SEQ ID NO.:11, the CDR2 of the heavy chain variable region corresponds to SEQ ID NO.:12 and the CDR3 of the heavy chain variable region corresponds to SEQ ID NO.:13.

Shorter versions of SEQ ID NOs.:11, 12 and 13 were presented in international application No. PCT/CA2006/001505 filed on Sep. 13, 2006 (i.e., the 1505 appl.) and published under No. WO2007/030930. In this patent application, the CDRs of SEQ ID NO.:37 (corresponding to SEQ ID NO.:22 in the '1505 appl.) were identified with the IMGT/V quest software that implements the IMGT definition. The corresponding sequences are identified herein as follow; the CDR1 of the heavy chain variable region corresponds to SEQ ID NO.:50, the CDR2 of the heavy chain variable region corresponds to SEQ ID NO.:51 and the CDR3 of the heavy chain variable region corresponds to SEQ ID NO.:52.

As used herein the term "amino acid substitution . . . outside of a complementarity determining region (CDR)" with respect to SEQ ID NO.:37 generally refers to amino acids (outside of) surrounding SEQ ID NOs.:11, 12 and 13. In some embodiments this term may alternatively refer to amino acids (outside of) surrounding SEQ ID NOs.:50, 51 and 52.

The CDRs of SEQ ID NO.:33 (identical to those of SEQ ID NOs. 34, 35, 36 and 18) were identified using the Kabat and Chothia definitions. The corresponding CDR sequences are identified herein as follow; the CDR1 of the light chain variable region corresponds to SEQ ID NO.:14, the CDR2 of the light chain variable region corresponds to SEQ ID NO.:15 and the CDR3 of the light chain variable region corresponds to SEQ ID NO.:16.

Shorter versions of SEQ ID NOs. 14, 15 and 16 were presented in international application No. PCT/CA2006/001505 filed on Sep. 13, 2006 (i.e., the 1505 appl.) and published under No. WO2007/030930. In this patent application, the CDRs of SEQ ID NO.:33 (corresponding to SEQ ID NO.:11 in the '1505 appl.) were identified with the IMGT/V quest software that implements the IMGT definition. The corresponding sequences are identified herein as follow; the CDR1 of the light chain variable region corresponds to SEQ ID NO.:53, the CDR2 of the light chain variable region corresponds to amino acid sequence "WAS" and the CDR3 of the light chain variable region corresponds to SEQ ID NO.:55.

As used herein the term "amino acid substitution . . . outside of a complementarity determining region (CDR)" with respect to SEQ ID NO.:33 generally refers to amino acids (outside of) surrounding SEQ ID NOs.:14, 15 and 16. In some embodiments this term may alternatively refer to amino acids (outside of) surrounding SEQ ID NOs.:53, the CDR2 of the light chain variable region and 55.

The humanized antibody of the present invention (or any antigen binding fragment derived therefrom) may comprise a light chain variable region selected from the group consisting of SEQ ID NO.:7, SEQ ID NO.:26 or SEQ ID NO.:27 and a heavy chain variable region selected from the group consisting of SEQ ID NO.:8, SEQ ID NO.:29 or SEQ ID NO.:30.

The hybrid antibody of the present invention (or any antigen binding fragment derived therefrom) may comprise a light chain variable region selected from the group consisting of SEQ ID NO.:7, SEQ ID NO.:26 or SEQ ID NO.:27 and a heavy chain variable region comprising SEQ ID NO.:28.

Alternatively the hybrid antibody of the present invention (or any antigen binding fragment derived therefrom) may comprise a light chain variable region comprising SEQ ID NO.:25 and a heavy chain variable region selected from the group consisting of SEQ ID NO.:8, SEQ ID NO.:29 or SEQ ID NO.:30.

The humanized antibody of the present invention (or any antigen binding fragment derived therefrom) may comprise a light chain variable region selected from the group consisting of SEQ ID NO.:18, SEQ ID NO.:32 or SEQ ID NO.:33 and a heavy chain variable region selected from the group consisting of SEQ ID NO.:17, SEQ ID NO.:35 or SEQ ID NO.:36.

The hybrid antibody of the present invention (or any antigen binding fragment derived therefrom) may comprise a light chain variable region selected from the group consisting of SEQ ID NO.:18, SEQ ID NO.:32 or SEQ ID NO.:33 and a heavy chain variable region comprising SEQ ID NO.:34.

Alternatively the hybrid antibody of the present invention (or any antigen binding fragment derived therefrom) may comprise a light chain variable region comprising SEQ ID NO.:31 and a heavy chain variable region selected from the group consisting of SEQ ID NO.:17, SEQ ID NO.:35 or SEQ ID NO.:36.

Another exemplary embodiment of the humanized antibody or antigen binding fragment of the present invention includes for example, an antibody or antigen binding fragment having a light chain variable region which may comprise at least 90 consecutive amino acids of any of SEQ ID NO.:26, SEQ ID NO.:27, SEQ ID NO.:28 or SEQ ID NO.:8.

As used herein the term "at least 90 consecutive amino acids of SEQ ID NO.:26" also includes the terms "at least 91, 92, 93, 94, 95, 96, 97, 98, 99, 100, 101, 102, 103, 104, 105, 106, 107, 108, 109, 110, 111 or at least 112 consecutive amino acids". The term "at least 90 consecutive amino acids of SEQ ID NO.:26" encompasses any possible sequence of at least 90 consecutive amino acids found in SEQ ID NO.:26 and especially those sequences which include the 3 CDRs of SEQ ID NO.:26, such as, for example a sequence comprising amino acids 6 to 108, 5 to 109, 13 to 103, 9 to 111 of SEQ ID NO.:26 and so on.

As used herein the term "at least 90 consecutive amino acids of SEQ ID NO.:27" also includes the terms "at least 91, 92, 93, 94, 95, 96, 97, 98, 99, 100, 101, 102, 103, 104, 105, 106, 107, 108, 109, 110, 111 or at least 112 consecutive amino acids". The term "at least 90 consecutive amino acids of SEQ ID NO.:27" encompasses any possible sequence of at least 90 consecutive amino acids found in SEQ ID NO.:27 and especially those sequences which include the 3 CDRs of SEQ ID NO.:27, such as, for example a sequence comprising amino acids 7 to 109, 12 to 104, 22 to 113, 18 to 112 of SEQ ID NO.:27 and so on.

The terms "at least 90 consecutive amino acids of SEQ ID NO:28" or "at least 90 consecutive amino acids of SEQ ID NO.:8" has a similar meaning.

In accordance with the present invention, the antibody or antigen binding fragment of the present invention may have, for example, a light chain variable region as set forth in SEQ ID NO.:8.

Also in accordance with the present invention, the antibody or antigen binding fragment of the present invention may have, for example, a light chain as set forth in SEQ ID NO.:10.

The humanized antibody or antigen binding fragment of the invention includes (or further includes) for example, a heavy chain variable region which may comprise at least 90 consecutive amino acids of any of SEQ ID NOs.:30, 31, 32 or 7.

As used herein the term "at least 90 consecutive amino acids of SEQ ID NO.:30" also includes the terms "at least 91, 92, 93, 94, 95, 96, 97, 98, 99, 100, 101, 102, 103, 104, 105, 106, 107, 108, 109, 110, 111, 112, 113, 114, 115, 116 or at least 117 consecutive amino acids". The term "at least 90 consecutive amino acids of SEQ ID NO.:30" encompasses any possible sequence of at least 90 consecutive amino acids found in SEQ ID NO.:30 and especially those sequences which include the 3 CDRs of SEQ ID NO.:30, such as, for example a sequence comprising amino acids 1 to 108, 2 to 112, 11 to 113, 7 to 109 of SEQ ID NO.:30 and so on.

As used herein the term "at least 90 consecutive amino acids of SEQ ID NO.:31" also includes the terms "at least 91, 92, 93, 94, 95, 96, 97, 98, 99, 100, 101, 102, 103, 104, 105, 106, 107, 108, 109, 110, 111, 112, 113, 114, 115, 116 or at least 117 consecutive amino acids". The term "at least 90 consecutive amino acids of SEQ ID NO.:31" encompasses any possible sequence of at least 90 consecutive amino acids found in SEQ ID NO.:31 and especially those sequences which include the 3 CDRs of SEQ ID NO.:31, for example a sequence comprising amino acids 6 to 109, 8 to 113, 1 to 108, 2 to 115 of SEQ ID NO.:31 and so on.

The terms "at least 90 consecutive amino acids of SEQ ID NO.:32" or "at least 90 consecutive amino acids of SEQ ID NO.:7" has a similar meaning.

In accordance with the present invention, the antibody or antigen binding fragment of the present invention may have, for example, a heavy chain variable region as set forth in SEQ ID NO.:7.

Also in accordance with the present invention, the antibody or antigen binding fragment of the present invention may have, for example, a heavy chain as set forth in SEQ ID NO.:9.

In accordance with the present invention the antibody or antigen binding fragment may comprise, for example, a) a light chain variable region which may comprise at least 90 consecutive amino acids of SEQ ID NO.:26 and a heavy chain variable region which may comprise at least 90 consecutive amino acids of any of SEQ ID NO.:30, SEQ ID NO.:31, SEQ ID NO.:32 or SEQ ID NO.:7;

b) a light chain variable region which may comprise at least 90 consecutive amino acids of SEQ ID NO.:27 and a heavy chain variable region which may comprise at least 90 consecutive amino acids of any of SEQ ID NO.:30, SEQ ID NO.:31, SEQ ID NO.:32 or SEQ ID NO.:7;

c) a light chain variable region which may comprise amino acids at least 90 consecutive amino acids of SEQ ID NO.:28 and a heavy chain variable region which may comprise at least 90 consecutive amino acids of any of SEQ ID NO.:30, SEQ ID NO.:31, SEQ ID NO.:32 or SEQ ID NO.:7 or;

d) a light chain variable region which may comprise at least 90 consecutive amino acids of SEQ ID NO.:8 and a heavy chain variable region which may comprise at least 90 consecutive amino acids of any of SEQ ID NO.:30, SEQ ID NO.:31, SEQ ID NO.:32 or SEQ ID NO.:7.

In accordance with a more specific embodiment of the invention, the light chain variable region may comprise at least 90 consecutive amino acids of SEQ ID NO.:8 and the heavy chain variable region may comprise at least 90 consecutive amino acids of SEQ ID NO.:7.

In accordance with an even more specific embodiment of the invention, the light chain variable region may be as set forth in SEQ ID NO.:8 and the heavy chain variable region may be as set forth in SEQ ID NO.:7.

Other exemplary embodiments of the humanized antibodies or antigen binding fragments of the invention are those which may comprise a light chain variable region which may comprise at least 90 consecutive amino acids of any of SEQ ID Nos. 34, 35, 36 or 18.

As used herein the term "at least 90 consecutive amino acids of SEQ ID NO.:34" also includes the terms "at least 91, 92, 93, 94, 95, 96, 97, 98, 99, 100, 101, 102, 103, 104, 105, 106, 107, 108, 109, 110, 111, 112 or at least 113, consecutive amino acids". The term "at least 90 consecutive amino acids of SEQ ID NO.:34" encompasses any possible sequence of at least 90 consecutive amino acids found in SEQ ID NO.:34 and especially those sequences which include the 3 CDRs of SEQ ID NO.:34, for example a sequence comprising amino acids 6 to 103, 11 to 106, 1 to 106, 3 to 110, 5 to 107 of SEQ ID NO.:34 and so on.

As used herein the term "at least 90 consecutive amino acids of SEQ ID NO.:35" also includes the terms "at least 91, 92, 93, 94, 95, 96, 97, 98, 99, 100, 101, 102, 103, 104, 105, 106, 107, 108, 109, 110, 111, 112 or at least 113, consecutive amino acids". The term "at least 90 consecutive amino acids of SEQ ID NO.:35" encompasses any possible sequence of at least 90 consecutive amino acids found in SEQ ID NO.:35 and especially those sequences which include the 3 CDRs of SEQ ID NO.:35, for example a sequence comprising amino acids 9 to 106, 10 to 113, 1 to 109, 20 to 110, 7 to 107 of SEQ ID NO.:35 and so on.

The terms "at least 90 consecutive amino acids of SEQ ID NO.:36" or "at least 90 consecutive amino acids of SEQ ID NO.:18" has a similar meaning.

In accordance with the present invention, the antibody or antigen binding fragment of the present invention may have, for example, a light chain variable region as set forth in SEQ ID NO.:18.

Also in accordance with the present invention, the antibody or antigen binding fragment of the present invention may have, for example, a light chain as set forth in SEQ ID NO.:20.

The humanized antibody or antigen binding fragment of the invention includes (or further includes) for example, a heavy chain variable region which may comprise at least 90 consecutive amino acids of any of SEQ ID NOs.:38, 39, 40 or 17.

As used herein the term "at least 90 consecutive amino acids of SEQ ID NO.:38" also includes the terms "at least 91, 92, 93, 94, 95, 96, 97, 98, 99, 100, 101, 102, 103, 104, 105, 106, 107, 108, 109, 110, 111, 112, 113, 114, 115, 116, 117 or at least 118 consecutive amino acids". The term "at least 90 consecutive amino acids of SEQ ID NO.:38" encompasses any possible sequence of at least 90 consecutive amino acids found in SEQ ID NO.:38 and especially those sequences which include the 3 CDRs of SEQ ID NO.:38, such as, for example a sequence comprising amino acids 6 to 111, 1 to 114, 12 to 109, 5 to 113, 10 to 107 of SEQ ID NO.:38 and so on.

As used herein the term "at least 90 consecutive amino acids of SEQ ID NO.:39" also includes the terms "at least 91, 92, 93, 94, 95, 96, 97, 98, 99, 100, 101, 102, 103, 104, 105, 106, 107, 108, 109, 110, 111, 112, 113, 114, 115, 116, 117 or at least 118 consecutive amino acids". The term "at least 90 consecutive amino acids of SEQ ID NO.:39" encompasses any possible sequence of at least 90 consecutive amino acids found in SEQ ID NO.:39 and especially those sequences which include the 3 CDRs of SEQ ID NO.:39, such as, for example a sequence comprising amino acids 3 to 109, 1 to 115, 1 to 110, 22 to 116, 20 to 115 of SEQ ID NO.:39 and so on.

The terms "at least 90 consecutive amino acids of SEQ ID NO.:40" or "at least 90 consecutive amino acids of SEQ ID NO.:17" has a similar meaning.

In accordance with the present invention, the antibody or antigen binding fragment of the present invention may have, for example, a heavy chain variable region as set forth in SEQ ID NO.:17.

Also in accordance with the present invention, the antibody or antigen binding fragment of the present invention may have, for example, a heavy chain as set forth in SEQ ID NO.:19. In accordance with the present invention the antibody or antigen binding fragment may comprise, for example, a) a light chain variable region which may comprise at least 90 consecutive amino acids of SEQ ID NO.:34 and a heavy chain variable region which may comprise at least 90 consecutive amino acids of any of SEQ ID NO.:38, SEQ ID NO.:39, SEQ ID NO.:40 or SEQ ID NO.:17;

b) a light chain variable region which may comprise at least 90 consecutive amino acids of SEQ ID NO.:35 and a heavy chain variable region which may comprise at least 90 consecutive amino acids of any of SEQ ID NO.:38, SEQ ID NO.:39, SEQ ID NO.:40 or SEQ ID NO.:17;

c) a light chain variable region which may comprise amino acids at least 90 consecutive amino acids of SEQ ID NO.:36 and a heavy chain variable region which may comprise at least 90 consecutive amino acids of any of SEQ ID NO.:38, SEQ ID NO.:39, SEQ ID NO.:40 or SEQ ID NO.:17 or;

d) a light chain variable region which may comprise at least 90 consecutive amino acids of SEQ ID NO.:18 and a heavy chain variable region which may comprise at least 90 consecutive amino acids of any of SEQ ID NO.:38, SEQ ID NO.:39, SEQ ID NO.:40 or SEQ ID NO.:17.

In accordance with a more specific embodiment of the invention, the light chain variable region may have at least 90 consecutive amino acids of SEQ ID NO.:18 and the heavy chain variable region may have at least 90 consecutive amino acids of SEQ ID NO.:17.

In accordance with an even more specific embodiment of the invention, the light chain variable region may be as set forth in SEQ ID NO.:18 and the heavy chain variable region may be as set forth in SEQ ID NO.:17.

Of course, the light chain or heavy chain or their variable region described herein may also contain a signal peptide. Such signal peptide may be from an original sequence or may be designed to optimize a particular cellular localization of the polypeptide. Of course, desirable signal peptides are those which may allow secretion of the polypeptide (e.g., cleavable).

The humanized or hybrid antibody of the present invention may have a constant region, preferably a human constant region. Although other subtypes may be selected, the humanized or hybrid antibody may comprise amino acids residues of a constant region of an immunoglobulin of an IgG1, IgG2 or IgG3 subtype.

The present invention also relates in another aspect, to an antigen binding fragment comprising a light chain variable region (or a fragment thereof) and a heavy chain variable region (or a fragment thereof), which may include non-human complementarity determining region amino acid residues and human framework region amino acid residues.

The antigen binding fragment of the present invention may bind to clusterin and may advantageously have a better affinity than an antigen binding fragment of a non-human parent antibody.

In fact, it has been shown herein that the antigen binding fragment binds to recombinant monomeric clusterin with an affinity of $1.7 \times 10^{-8}$ M$\pm 2.97 \times 10^{-9}$ or better.

In an exemplary embodiment, the antigen binding fragment may comprise human framework region amino acid residues of the natural human antibody heavy chain as described herein and a heavy chain CDR selected from the group consisting of a CDRH1 having an amino acid sequence of SEQ ID NO.:1, a CDRH2 having an amino acid sequence of SEQ ID NO.:2 and a CDRH3 having an amino acid sequence of SEQ ID NO.:3 or a heavy chain CDR selected from the group consisting of a CDRH1 having an amino acid sequence of SEQ ID NO.:11, a CDRH2 having an amino acid sequence of SEQ ID NO.:12 and a CDRH3 having an amino acid sequence of SEQ ID NO.:13.

In another exemplary embodiment, the antigen binding fragment may comprise human framework region amino acid residues of the natural human antibody heavy chain as described herein and at least two heavy chain CDRs selected from the group consisting of a CDRH1 having an amino acid sequence of SEQ ID NO.:1, a CDRH2 having an amino acid sequence of SEQ ID NO.:2 and a CDRH3 having an amino acid sequence of SEQ ID NO.:3 or at least two heavy chain CDR selected from the group consisting of a CDRH1 having an amino acid sequence of SEQ ID NO.:11, a CDRH2 having an amino acid sequence of SEQ ID NO.:12 and a CDRH3 having an amino acid sequence of SEQ ID NO.:13.

In yet another exemplary embodiment, the antigen binding fragment may comprise human framework region amino acid residues of the natural human antibody heavy chain as described herein and a CDRH1 having an amino acid sequence of SEQ ID NO.:1, a CDRH2 having an amino acid sequence of SEQ ID NO.:2 and a CDRH3 having an amino acid sequence of SEQ ID NO.:3 or a CDRH1 having an amino acid sequence of SEQ ID NO.:11, a CDRH2 having an amino acid sequence of SEQ ID NO.:12 and a CDRH3 having an amino acid sequence of SEQ ID NO.:13.

In a more particular embodiment, the antigen binding fragment may comprise a heavy chain variable region having an amino acid sequence of SEQ ID NO:7 or SEQ ID NO.:17 (or a fragment thereof).

In a further exemplary embodiment, the antigen binding fragment may comprise human framework region amino acid residues of the natural human antibody light chain as described herein and a light chain CDR selected from the group consisting of a CDRL1 having an amino acid sequence of SEQ ID NO.:4, a CDRL2 having an amino acid sequence of SEQ ID NO.:5 and a CDRL3 having an amino acid sequence of SEQ ID NO.:6 or a light chain CDR selected from the group consisting of a CDRL1 having an amino acid sequence of SEQ ID NO.:14, a CDRL2 having an amino acid sequence of SEQ ID NO.:15 and a CDRL3 having an amino acid sequence of SEQ ID NO.:16.

In yet a further exemplary embodiment, the antigen binding fragment may comprise human framework region amino acid residues of the natural human antibody light chain as described herein and at least two light chain CDRs selected from the group consisting of a CDRL1 having an amino acid sequence of SEQ ID NO.:4, a CDRL2 having an amino acid sequence of SEQ ID NO.:5 and a CDRL3 having an amino acid sequence of SEQ ID NO.:6 or at least two light chain CDR selected from the group consisting of a CDRL1 having an amino acid sequence of SEQ ID NO.:14, a CDRL2 having an amino acid sequence of SEQ ID NO.:15 and a CDRL3 having an amino acid sequence of SEQ ID NO.:16.

In still a further exemplary embodiment, the antigen binding fragment may comprise human framework region amino acid residues of the natural human antibody light chain as described herein and a CDRL1 having an amino acid sequence of SEQ ID NO.:4, a CDRL2 having an amino acid sequence of SEQ ID NO.:5 and a CDRL3 having an amino acid sequence of SEQ ID NO.:6 or a CDRL1 having an amino acid sequence of SEQ ID NO.:14, a CDRL2 having an amino acid sequence of SEQ ID NO.:15 and a CDRL3 having an amino acid sequence of SEQ ID NO.:16.

In a more specific embodiment, the antigen binding fragment may comprise a light chain variable region having an amino acid sequence of SEQ ID NO.:8 or SEQ ID NO.:18 or a fragment thereof.

In accordance with the present invention, the antigen binding fragment may be, for example, a Fab fragment, a F(ab')$_2$ fragment, a Fd fragment, a Fv fragment or a dAb fragment.

Preferably, the antigen binding fragment may be, for example, a Fab fragment or a F(ab')$_2$ fragment.

The present invention also encompasses an isolated antibody comprising the amino acid sequence of the antigen binding fragment described herein. The isolated antibody may also comprise a constant region.

Variant Antibody and Antigen Binding Fragments

Although, substituting CDRs from rodent antibodies for the human CDRs in human frameworks is sometimes sufficient to transfer high antigen binding affinity (Jones, P. T. et al., Nature 321:522-525 (1986); Verhoeyen, M. et al., Science 239:1534-1536 (1988)), in other cases it is necessary to additionally replace one (Riechmann, L. et al., Nature 332:323-327 (1988)) or several (Queen, C. et al., Proc. Natl. Acad. Sci. USA 86:10029-10033 (1989)) framework region residues. Substantial unpredictability in the art of antibody humanization still exists. For example, in U.S. Pat. No. 7,537,931, attempts at transferring the CDRs of a murine antibody into a human antibody resulted in lost of binding to the antigen.

If the humanization process does not result in a humanized or hybrid antibody having the desired characteristics (i.e., specificity, affinity, etc.), it is possible to substitute non-human amino acid framework residues for human amino acid framework residues.

The present invention therefore encompasses variants of the humanized or hybrid antibodies or antigen binding fragments described herein. Variant antibodies or antigen binding fragments included are those having a variation in the amino acid sequence of the humanized or hybrid antibody or antigen binding fragments described herein. For example, variant antibodies or antigen binding fragments encompassed by the present invention are those having a light chain variable region and a heavy chain variable region which may include non-human complementarity determining region amino acid residues and human framework region amino acid residues of a natural human antibody and further comprising at least one amino acid variation (preferably in the framework region).

Variant antibodies or antigen binding fragments included in the present invention are those having, for example, similar or improved characteristics in comparison with the humanized or hybrid antibody or antigen binding fragment but which carries at least one amino acid variation in comparison with the humanized or hybrid antibody described herein.

Variant antibodies or antigen binding fragments encompassed by the present invention are those which may comprise an insertion, a deletion or an amino acid substitution (conservative or non-conservative). Some variants may thus have at least one amino acid residue in its amino acid sequence removed and a different residue inserted in its place.

The sites of interest for substitutional mutagenesis may include the hypervariable regions (CDRs), the framework region or even the constant region. Conservative substitutions may be made by exchanging an amino from one of the groups listed below (group 1 to 6) for another amino acid of the same group.

Other exemplary embodiments of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

Examples of substitutions identified as "conservative substitutions" are shown in Table 1A. If such substitutions result in a change not desired, then other type of substitutions, denominated "exemplary substitutions" in Table 1A, or as further described herein in reference to amino acid classes, are introduced and the products screened.

Substantial modifications in function or immunological identity may be accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(group 1) hydrophobic: norleucine, methionine (Met), Alanine (Ala), Valine (Val), Leucine (Leu), Isoleucine (Ile)
(group 2) neutral hydrophilic: Cysteine (Cys), Serine (Ser), Threonine (Thr)
(group 3) acidic: Aspartic acid (Asp), Glutamic acid (Glu)
(group 4) basic: Asparagine (Asn), Glutamine (Gln), Histidine (His), Lysine (Lys), Arginine (Arg)
(group 5) residues that influence chain orientation: Glycine (Gly), Proline (Pro); and
(group 6) aromatic: Tryptophan (Trp), Tyrosine (Tyr), Phenylalanine (Phe)

Non-conservative substitutions will entail exchanging a member of one of these classes for another.

TABLE 1A

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala | Ala |
| His (H) | Asn, Gln, Lys, Arg, | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |

TABLE 1A-continued

Amino acid substitution

| Original residue | Exemplary substitution | Conservative substitution |
|---|---|---|
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Variation in the amino acid sequence of the variant antibody or antigen binding fragment may include an amino acid addition, deletion, insertion, substitution etc., one or more modification in the backbone or side-chain of one or more amino acid, or an addition of a group or another molecule to one or more amino acids (side-chains or backbone).

Variant antibody or antigen binding fragment may have substantial sequence similarity and/or sequence identity in its amino acid sequence in comparison with that the original antibody or antigen binding fragment amino acid sequence. The degree of similarity between two sequences is based upon the percentage of identities (identical amino acids) and of conservative substitution.

When determining percent identity of a framework region in comparison with another framework region, the CDRs amino acid sequence should preferably not be taken into account. The percent identity of a framework region in comparison with another is preferably determined over the entire framework region and not framework by framework.

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position.

Percent similarity will be indicative of amino acids which are identical and those which are replaced with conservative amino acid substitution in comparison with the original peptide at the same or similar position.

Variants of the present invention therefore comprise those which may have at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

Exemplary embodiments of variants are those having at least 81% sequence identity to a sequence described herein and 81%, 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 82% sequence identity to a sequence described herein and 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 90% sequence identity to a sequence described herein and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision the applicant provides herein a Table 1B illustrating exemplary embodiments of individual variants encompassed by the present invention and comprising the specified % sequence identity and % sequence similarity. Each "X" is to be construed as defining a given variant.

1 to 15 and so on; 2 to 20; 2 to 19; 2 to 18; 2 to 17 and so on; 3 to 20; 3 to 19; 3 to 18 and so on; 4 to 20; 4 to 19; 4 to 18; 4 to 17; 4 to 16 and so on; 5 to 20; 5 to 19; 5 to 18; 5 to 17 and so on, etc.

Likewise, the term "from one to twelve" includes every individual values and ranges such as for example, 1, 2, 3, and up to 12; 1 to 12; 1 to 11; 1 to 10 and so on; 2 to 12; 2 to 11, 2 to 10; 2 to 9; 2 to 8 and so on; 3 to 12; 3 to 11; 3 to 10; 3 to 9 and so on; 4 to 12; 4 to 11 and so on; 5 to 12; 5 to 11; 5 to 10; 5 to 9; 5 to 8; 5 to 7; and so on, etc.

Similar terms are to be interpreted in a similar manner.

The invention encompasses or uses amino acid sequence having a desired % identity with another amino acid sequence, for example, "a natural human antibody light chain framework region having at least 70% identity with the light chain framework region of the non-human parent antibody" or "a natural human antibody heavy chain framework region having at least 70% identity with the heavy chain framework region of the non-human parent antibody".

The term "a natural human antibody light chain framework region having at least 70% identity with the light chain framework region of the non-human parent antibody" encompasses a natural human antibody light chain framework region having 70%, 71%, 72%, 73%, 74%, 75%, 76%,

TABLE 1B

| | | Percent (%) sequence identity | | | | | | | | | | | | | | | | | | | |
|---|---|---|---|---|---|---|---|---|---|---|---|---|---|---|---|---|---|---|---|---|---|
| | | 80 | 81 | 82 | 83 | 84 | 85 | 86 | 87 | 88 | 89 | 90 | 91 | 92 | 93 | 94 | 95 | 96 | 97 | 98 | 99 | 100 |
| Percent (%) sequence similarity | 80 | X | | | | | | | | | | | | | | | | | | | | |
| | 81 | X | X | | | | | | | | | | | | | | | | | | | |
| | 82 | X | X | X | | | | | | | | | | | | | | | | | | |
| | 83 | X | X | X | X | | | | | | | | | | | | | | | | | |
| | 84 | X | X | X | X | X | | | | | | | | | | | | | | | | |
| | 85 | X | X | X | X | X | X | | | | | | | | | | | | | | | |
| | 86 | X | X | X | X | X | X | X | | | | | | | | | | | | | | |
| | 87 | X | X | X | X | X | X | X | X | | | | | | | | | | | | | |
| | 88 | X | X | X | X | X | X | X | X | X | | | | | | | | | | | | |
| | 89 | X | X | X | X | X | X | X | X | X | X | | | | | | | | | | | |
| | 90 | X | X | X | X | X | X | X | X | X | X | X | | | | | | | | | | |
| | 91 | X | X | X | X | X | X | X | X | X | X | X | X | | | | | | | | | |
| | 92 | X | X | X | X | X | X | X | X | X | X | X | X | X | | | | | | | | |
| | 93 | X | X | X | X | X | X | X | X | X | X | X | X | X | X | | | | | | | |
| | 94 | X | X | X | X | X | X | X | X | X | X | X | X | X | X | X | | | | | | |
| | 95 | X | X | X | X | X | X | X | X | X | X | X | X | X | X | X | X | | | | | |
| | 96 | X | X | X | X | X | X | X | X | X | X | X | X | X | X | X | X | X | | | | |
| | 97 | X | X | X | X | X | X | X | X | X | X | X | X | X | X | X | X | X | X | | | |
| | 98 | X | X | X | X | X | X | X | X | X | X | X | X | X | X | X | X | X | X | X | | |
| | 99 | X | X | X | X | X | X | X | X | X | X | X | X | X | X | X | X | X | X | X | X | |
| | 100 | X | X | X | X | X | X | X | X | X | X | X | X | X | X | X | X | X | X | X | X | X |

The present invention thus encompasses humanized or hybrid antibody in which non-human amino acid framework residues are reintroduced or where other types of amino acid modifications are made. Those amino acids that are particularly selected to optimize the characteristics of the antibody include those that are involved in antigen binding. Examples, of such amino acids are provided in FIG. 2.

In an exemplary embodiment, the humanized or hybrid antibody of the present invention may thus comprise from one to twenty-one non-human framework region amino acid residues in the heavy chain variable region (back mutations).

In another exemplary embodiment, the humanized or hybrid antibody may comprise from one to twelve non-human framework region amino acid residues in the light chain variable region (back mutations).

As used herein the term "from one to twenty" includes every individual values and ranges such as for example, 1, 2, 3, and up to 20; 1 to 20; 1 to 19; 1 to 18; 1 to 17; 1 to 16;

77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with the light chain framework region of the non-human parent antibody. The % identity is preferably determined over the entire framework regions (i.e., excluding the CDRs).

As mentioned above for with respect to variants, the term "a light chain framework region having at least 70% identity with the light chain framework region of the non-human parent antibody" encompasses a light chain framework region having 70% identity with the light chain framework region of the non-human parent antibody and which may also have 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence similarity with the light chain framework region of the non-human parent antibody.

The term "a natural human antibody heavy chain framework region having at least 70% identity with the heavy chain framework region of the non-human parent antibody" encompasses a natural human antibody heavy chain framework region having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with the heavy chain framework region of the non-human parent antibody.

As mentioned above for with respect to variants, the term "a heavy chain framework region having at least 70% identity with the heavy chain framework region of the non-human parent antibody" encompasses a heavy chain framework region having 70% identity with the heavy chain framework region of the non-human parent antibody and which may also have 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence similarity with the heavy chain framework region of the non-human parent antibody.

Production of the Antibodies in Cells

The antibodies that are disclosed herein can be made by a variety of methods familiar to those skilled in the art (recombinant DNA methods, chemical synthesis etc.).

In order to express the antibodies, nucleotide sequences able to encode any one of a light and heavy immunoglobulin chains described herein may be inserted into an expression vector, e.g., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express a polypeptide or RNA derived from nucleotide sequences able to encode any one of a light and heavy immunoglobulin chains described herein. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, nucleotide sequences able to encode any one of a light and heavy immunoglobulin chains described herein may be transformed into cell lines using expression vectors that may contain viral origins of replication and/or endogenous expression elements and a selectable or visible marker gene on the same or on a separate vector. The invention is not to be limited by the vector or host cell employed. In certain embodiments of the present invention, the nucleotide sequences able to encode any one of a light and heavy immunoglobulin chains described herein may each be ligated into a separate expression vector and each chain expressed separately. In another embodiment, both the light and heavy chains able to encode any one of a light and heavy immunoglobulin chains described herein may be ligated into a single expression vector and expressed simultaneously.

Alternatively, RNA and/or polypeptide may be expressed from a vector comprising nucleotide sequences able to encode any one of a light and heavy immunoglobulin chains described herein using an in vitro transcription system or a coupled in vitro transcription/translation system.

In general, host cells that contain nucleotide sequences able to encode any one of a light and heavy immunoglobulin chains described herein and/or that express a polypeptide encoded by the nucleotide sequences able to encode any one of a light and heavy immunoglobulin chains described herein, or a portion thereof, may be identified by a variety of procedures known to those of skill in the art. These procedures include, but are not limited to, DNA/DNA or DNA/RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

Host cells comprising nucleotide sequences able to encode any one of a light and heavy immunoglobulin chains described herein may thus be cultured under conditions for the transcription of the corresponding RNA and/or the expression of the polypeptide from cell culture. The polypeptide produced by a cell may be secreted or may be retained intracellularly depending on the sequence and/or the vector used. In an exemplary embodiment, expression vectors containing nucleotide sequences able to encode any one of a light and heavy immunoglobulin chains described herein may be designed to contain signal sequences that direct secretion of the polypeptide through a prokaryotic or eukaryotic cell membrane.

An exemplary embodiment of a nucleic acid encoding a heavy chain variable region is provided in SEQ ID NO.:21 and SEQ ID NO.:22.

An exemplary embodiment of a nucleic acid encoding a light chain variable region is provided in SEQ ID NO.:23 and SEQ ID NO.:24.

Due to the inherent degeneracy of the genetic code, other DNA sequences that encode the same, substantially the same or a functionally equivalent amino acid sequence may be produced and used, for example, to express a polypeptide encoded by nucleotide sequences able to encode any one of a light and heavy immunoglobulin chains described herein. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. In an exemplary embodiment, antibodies that contain particular glycosylation structures or patterns may be desired. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and antibody epitopes such as monoclonal antibody epitopes.

In yet a further aspect, the present invention relates to a polynucleotide which may comprise a nucleotide sequence encoding a fusion protein. The fusion protein may comprise a fusion partner (e.g., HA, Fc, etc.) fused to the polypeptide (e.g., complete light chain, complete heavy chain, variable regions. CDRs etc.) described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

When only one of the light chain variable domain or the heavy chain variable domain is available, an antibody or antigen-binding fragment may be reconstituted by screening a library of complementary variable domains using methods known in the art (Portolano et al. The Journal of Immunology (1993) 150:880-887, Clarkson et al., Nature (1991) 352:624-628). As such, knowing only one of the variable region amino acid sequence (heavy chain variable region or light chain variable region) is often enough to reconstitute an intact antibody having the desired antigen binding specificity. Therefore, nucleic acids encoding a light chain variable region or a heavy chain variable region of an antibody may be useful in identifying a complementary chain which when assembled with one another forms an antigen binding fragment or antibody having sufficient antigen binding specificity. A single stranded nucleic acid (e.g., oligo) or its complement having a high level of sequence identity with the nucleic acids encoding a light chain variable region or a heavy chain variable region of an antibody may be useful to detect the latter or to detect any other nucleic acid sequence sharing a high level of sequence identity.

Therefore, in an additional aspect, the present invention also provides an isolated nucleic acid encoding the light chain variable region and/or the heavy chain variable region of the humanized or hybrid antibody described herein, encoding the antigen binding fragment described herein or the isolated antibody described herein.

In yet an additional aspect, the present invention provides a vector or construct, comprising the (isolated) nucleic acid described herein. In accordance with the present invention, the vector may be, for example, a mammalian expression vector, a bacterial expression vector etc.

The present invention also encompasses, an isolated cell comprising the isolated nucleic acid described herein or the vector described herein. Isolated cells expressing the antibody or antigen binding fragment of the present invention are also encompassed herewith. Suitable cells, include for example, a mammalian cell, a bacterial cell, etc.

Yet another aspect of the invention relate to a method for making a humanized or hybrid anti-clusterin antibody which may comprise introducing non-human heavy chain CDR amino acid residues of a non-human antibody capable of specific binding to clusterin into a framework region of a natural human antibody heavy chain variable region.

Yet an additional aspect of the invention relates to a method for making a humanized or hybrid anti-clusterin antibody which may comprise transforming a cell with a nucleic acid encoding a heavy chain variable region (or a complete heavy chain) comprising non-human heavy chain CDR amino acid residues of a non-human antibody capable of specific binding to clusterin and framework region amino acids of a natural human antibody heavy chain variable region. The method may also comprise transforming the cell with a nucleic acid encoding a complementary light chain variable region (or a complete light chain).

In another aspect, the invention relates to a method for making a humanized or hybrid anti-clusterin antibody which may comprise expressing a heavy chain variable region (or a complete heavy chain) comprising non-human heavy chain CDR amino acid residues of a non-human antibody capable of specific binding to clusterin and framework region amino acids of a natural human antibody heavy chain variable region. The method may also comprise expressing a complementary light chain variable region (or a complete light chain).

The natural human antibody heavy chain variable region which may be selected for humanization purposes may have the following characteristics: a) a three-dimensional structure similar to or identical (superimposable) to that of a heavy chain of the non-human antibody, b) a framework region having an amino acid sequence at least 70% identical to a heavy chain framework region of the non-human antibody, and/or; c) (a number of) amino acid residues in a heavy chain CDR (e.g., all three CDRs) that is the same or substantially the same as that of the non-human heavy chain CDR amino acid residues.

The method may thus comprise, for example, introducing non-human heavy chain CDR amino acid residues of at least two CDRs of the non-human antibody. The nucleic acid used in methods of making humanized or hybrid antibodies may thus encode at least two CDRs of the non-human antibody. The heavy chain variable region that is expressed in methods of making humanized or hybrid antibodies may thus comprise at least two CDRs of the non-human antibody.

The method may preferably comprise introducing non-human heavy chain CDR amino acid residues of all three CDRs. The nucleic acid used in methods of making humanized or hybrid antibodies may thus encode three CDRs of the non-human antibody. The heavy chain variable region that is expressed in methods of making humanized or hybrid antibodies may thus comprise three CDRs of the non-human antibody.

The method thus includes introducing the non-human CDRs comprising the amino acid sequence of SEQ ID NO.:1, SEQ ID NO.:2 and SEQ ID NO.:3. The nucleic acid used in methods of making humanized or hybrid antibodies may thus encode SEQ ID NO.:1, SEQ ID NO.:2 and SEQ ID NO.:3. The heavy chain variable region that is expressed in methods of making humanized or hybrid antibodies may thus comprise SEQ ID NO.:1, SEQ ID NO.:2 and SEQ ID NO.:3.

The method thus also includes introducing the non-human CDRs comprising the amino acid sequence of SEQ ID NO.:11, SEQ ID NO.:12 and SEQ ID NO.:13. The nucleic acid used in methods of making humanized or hybrid antibodies may thus encode SEQ ID NO.:11, SEQ ID NO.:12 and SEQ ID NO.:13. The heavy chain variable region that is expressed in methods of making humanized or hybrid antibodies may thus comprise SEQ ID NO.: 11, SEQ ID NO.:12 and SEQ ID NO.:13.

Alternatively, shorter versions of the above-mentioned CDRs may be introduced into a framework region of a natural human antibody heavy chain variable region.

The method of the present invention may further comprise introducing non-human light chain CDR amino acid residues of a non-human antibody capable of specific binding to clusterin into a framework region of a natural human antibody light chain variable region.

The method of the present invention may comprise allowing expression of a nucleic acid encoding a light chain variable region (or a complete light chain) comprising non-human light chain CDR amino acid residues of a non-human antibody capable of specific binding to clusterin and framework region amino acids of a natural human antibody light chain variable region. The method may also comprise transforming the cell with a nucleic acid encoding a complementary heavy chain variable region (or a complete heavy chain).

In another aspect, the invention relates to a method for making a humanized or hybrid anti-clusterin antibody which may comprise expressing a light chain variable region (or a complete heavy chain) comprising non-human light chain CDR amino acid residues of a non-human antibody capable of specific binding to clusterin and framework region amino acids of a natural human antibody light chain variable region. The method may also comprise expressing a complementary heavy chain variable region (or a complete heavy chain).

The natural human antibody light chain variable region which may be selected for humanization purposes may have the following characteristics: a) a three-dimensional structure similar to or identical (superimposable) to that of a light chain of the non-human antibody, b) a framework region having an amino acid sequence at least 70% identical to a light chain framework region of the non-human antibody, and/or; c) (a number of) amino acid residues in a light chain CDR (e.g., all three CDRs) that is the same or substantially the same as that of the non-human light chain CDR amino acid residues.

The method may thus comprise, for example, introducing non-human light chain CDR amino acid residues of at least two CDRs of the non-human antibody. The nucleic acid used in methods of making humanized or hybrid antibodies may thus encode at least two CDRs of the non-human antibody. The light chain variable region that is expressed in methods of making humanized or hybrid antibodies may thus comprise at least two CDRs of the non-human antibody.

The method may preferably comprise introducing non-human light chain CDR amino acid residues of all three CDRs. The nucleic acid used in methods of making humanized or hybrid antibodies may thus encode three CDRs of the non-human antibody. The light chain variable region that is expressed in methods of making humanized or hybrid antibodies may thus comprise three CDRs of the non-human antibody.

The method thus includes introducing the non-human CDRs comprising the amino acid sequence of SEQ ID NO.:4, SEQ ID NO.:5 and SEQ ID NO.:6. The nucleic acid used in methods of making humanized or hybrid antibodies may thus encode SEQ ID NO.:4, SEQ ID NO.:5 and SEQ ID NO.:6. The light chain variable region that is expressed in methods of making humanized or hybrid antibodies may thus comprise SEQ ID NO.:4, SEQ ID NO.:5 and SEQ ID NO.:6.

The method thus also includes introducing the non-human CDRs comprising the amino acid sequence of SEQ ID NO.:14, SEQ ID NO.:15 and SEQ ID NO.:16. The nucleic acid used in methods of making humanized or hybrid antibodies may thus encode SEQ ID NO.:14, SEQ ID NO.:15 and SEQ ID NO.:16. The light chain variable region that is expressed in methods of making humanized or hybrid antibodies may thus comprise SEQ ID NO.:14, SEQ ID NO.:15 and SEQ ID NO.:16.

Alternatively, shorter versions of the above-mentioned CDRs may be introduced into a framework region of a natural human antibody heavy chain variable region.

An additional aspect of the invention concerns a method for making a humanized anti-clusterin antibody which may comprise introducing non-human heavy chain CDR amino acid residues of a non-human antibody capable of specific binding to clusterin into a framework region of a natural human antibody heavy chain variable region and introducing non-human light chain CDR amino acid residues of a non-human antibody capable of specific binding to clusterin into a framework region of a natural human antibody light chain variable region.

Yet, an additional aspect of the invention concerns a method for making a humanized anti-clusterin antibody which may comprise allowing expression of a nucleic acid encoding non-human heavy chain CDR amino acid residues of a non-human antibody capable of specific binding to clusterin and a framework region of a natural human antibody heavy chain variable region and allowing expression of a nucleic acid encoding a non-human light chain CDR amino acid residues of a non-human antibody capable of specific binding to clusterin and a framework region of a natural human antibody light chain variable region.

The natural human antibody heavy chain variable region which may be selected for humanization purposes may have the following characteristics: a) comprising a framework region having an amino acid sequence at least 70% identical to a heavy chain framework region of the non-human antibody, and; b) having (a number of) amino acid residues in a heavy chain CDR (e.g., all three CDRs) that is the same or substantially the same as that of the non-human heavy chain CDR amino acid residues, while the natural human antibody light chain variable region which may be selected for humanization purposes may have the following characteristics: a) comprising a framework region having an amino acid sequence at least 70% identical to a light chain framework region of the non-human antibody, and; b) having (a number of) amino acid residues in a light chain CDR (e.g., all three CDRs) that is the same or substantially the same as that of the non-human light chain CDR amino acid residues. The natural human antibody variable region(s) preferably has a three-dimensional structure similar to or identical (superimposable) to that of the non-human antibody variable region(s).

In accordance with the present invention, the method may comprise introducing non-human heavy chain CDR amino acid residues of at least two CDRs of the non-human antibody. The nucleic acid used in methods of making humanized or hybrid antibodies may thus encode at least two CDRs of the non-human antibody. The heavy chain variable region that is expressed in methods of making humanized or hybrid antibodies may thus comprise at least two CDRs of the non-human antibody.

Alternatively, the method may comprise introducing non-human heavy chain CDR amino acid residues of all three CDRs. The nucleic acid used in methods of making humanized or hybrid antibodies may thus encode three CDRs of the non-human antibody. The heavy chain variable region that is expressed in methods of making humanized or hybrid antibodies may thus comprise three CDRs of the non-human antibody.

Also in accordance with the present invention, the method may comprise introducing non-human light chain CDR amino acid residues of at least two CDRs of the non-human antibody.

The nucleic acid used in methods of making humanized or hybrid antibodies may thus encode at least two CDRs of the non-human antibody. The light chain variable region that is expressed in methods of making humanized or hybrid antibodies may thus comprise at least two CDRs of the non-human antibody.

Alternatively, the method may comprise introducing non-human light chain CDR amino acid residues of all three CDRs. The nucleic acid used in methods of making humanized or hybrid antibodies may thus encode three CDRs of the non-human antibody. The light chain variable region that is expressed in methods of making humanized or hybrid antibodies may thus comprise three CDRs of the non-human antibody.

Using the method described herein, CDRs comprising the amino acid sequence of SEQ ID NO.:1, SEQ ID NO.:2 and SEQ ID NO.:3 are advantageously imported into the natural human antibody heavy chain variable region. The nucleic acid used in methods of making humanized or hybrid antibodies may thus encode SEQ ID NO.:1, SEQ ID NO.:2 and SEQ ID NO.:3. The light chain variable region that is expressed in methods of making humanized or hybrid antibodies may thus comprise SEQ ID NO.:1, SEQ ID NO.:2 and SEQ ID NO.:3.

Using the method described herein, CDRs comprising the amino acid sequence of SEQ ID NO.:11, SEQ ID NO.:12 and SEQ ID NO.:13 are advantageously imported into the natural human antibody heavy chain variable region. The nucleic acid used in methods of making humanized or hybrid antibodies may thus encode SEQ ID NO.:11, SEQ ID NO.:12 and SEQ ID NO.:13. The light chain variable region that is expressed in methods of making humanized or hybrid antibodies may thus comprise SEQ ID NO.:11, SEQ ID NO.:12 and SEQ ID NO.:13.

Using the method described herein, CDRs comprising the amino acid sequence of SEQ ID NO.:4, SEQ ID NO.:5 and SEQ ID NO.:6 are advantageously imported into the natural human antibody light chain variable region. The nucleic acid used in methods of making humanized or hybrid antibodies may thus encode SEQ ID NO.:4, SEQ ID NO.:5 and SEQ ID NO.:6. The light chain variable region that is expressed in methods of making humanized or hybrid antibodies may thus comprise SEQ ID NO.:4, SEQ ID NO.:5 and SEQ ID NO.:6.

Using the method described herein, CDRs comprising the amino acid sequence of SEQ ID NO.:14, SEQ ID NO.:15 and SEQ ID NO.:16 are advantageously imported into the natural human antibody light chain variable region. The nucleic acid used in methods of making humanized or hybrid antibodies may thus encode SEQ ID NO.:14, SEQ ID NO.:15 and SEQ ID NO.:16. The light chain variable region that is expressed in methods of making humanized or hybrid antibodies may thus comprise SEQ ID NO.:14, SEQ ID NO.:115 and SEQ ID NO.:16.

In another aspect, the present invention, concerns a method for making a humanized or hybrid anti-clusterin antibody which may comprise transforming a host cell with a nucleic acid encoding the heavy chain variable region described herein.

Exemplary embodiments of suitable heavy chain variable region are those of the non-human antibody which may comprise three CDRs having the amino acid sequence of SEQ ID NO.:1, SEQ ID NO.:2 and SEQ ID NO.:3 and natural human antibody heavy chain framework region having an amino acid sequence at least 70% identical to a heavy chain framework region of the non-human antibody. Preferably, the natural human antibody may comprise (a number of) heavy chain CDR amino acid residues that is the same or substantially the same as that of a CDR (e.g., all three CDRs) of the non-human heavy chain.

Exemplary embodiments of suitable heavy chain variable region are those of the non-human antibody which may comprise three CDRs having the amino acid sequence of SEQ ID NO.:11, SEQ ID NO.:12 and SEQ ID NO.:13 and natural human antibody heavy chain framework region having an amino acid sequence at least 70% identical to a heavy chain framework region of the non-human antibody. Preferably, the natural human antibody may comprise (a number of) heavy chain CDR amino acid residues that is the same or substantially the same as that of a CDR (e.g., all three CDRs) of the non-human heavy chain.

The method of the present invention may further comprise transforming a host cell with a nucleic acid encoding a complementary light chain.

If desirable, the complementary light chain may be encoded by the same nucleic acid as that encoding the heavy chain.

Such complementary light chain may comprise a light chain variable region of a non-human antibody which may comprise three CDRs having the amino acid sequence of SEQ ID NO.:4, SEQ ID NO.:5 and SEQ ID NO.:6 and natural human antibody light chain framework region having an amino acid sequence at least 70% identical to a light chain framework region of the non-human antibody. Preferably, the natural human antibody may comprise (a number of) light chain CDR amino acid residues that is the same or substantially the same as that of a CDR (e.g., all three CDRs) of the non-human light chain.

Such complementary light chain may comprise a light chain variable region of a non-human antibody which may comprise three CDRs having the amino acid sequence of SEQ ID NO.:14, SEQ ID NO.:15 and SEQ ID NO.:16 and natural human antibody light chain framework region having an amino acid sequence at least 70% identical to a light chain framework region of the non-human antibody. Preferably, the natural human antibody may comprise (a number of) light chain CDR amino acid residues that is the same or substantially the same as that of a CDR (e.g., all three CDRs) of the non-human light chain.

In yet another aspect, the present invention relates to a method for making a humanized or hybrid anti-clusterin antibody which may comprise transforming a host cell with a nucleic acid encoding a light chain variable region.

Exemplary embodiments of suitable light chain variable region are those of a non-human antibody which may comprise three CDRs having the amino acid sequence of SEQ ID NO.:4, SEQ ID NO.:5 and SEQ ID NO.:6 and natural human antibody light chain framework region having an amino acid sequence at least 70% identical to a light chain framework region of the non-human antibody. Preferably, the natural human antibody comprises (a number of) light chain CDR amino acid residues that is the same or substantially the same as that of a CDR (e.g., all three CDRs) of the non-human light chain.

Exemplary embodiments of suitable light chain variable region are those of a non-human antibody which may comprise three CDRs having the amino acid sequence of SEQ ID NO.:14, SEQ ID NO.:15 and SEQ ID NO.:16 and natural human antibody light chain framework region having an amino acid sequence at least 70% identical to a light chain framework region of the non-human antibody. Preferably, the natural human antibody comprises (a number of) light chain CDR amino acid residues that is the same or substantially the same as that of a CDR (e.g., all three CDRs) of the non-human light chain.

The method of the present invention may further comprise transforming a host cell with a nucleic acid encoding a complementary heavy chain.

If desirable, the complementary heavy chain may be encoded by the same nucleic acid as that encoding the light chain.

Pharmaceutical Compositions of the Antibodies and their Use

In another aspect, the present invention relates to a pharmaceutical composition which may comprise, for example, the humanized or hybrid antibody described herein, the antigen binding fragment described herein or the isolated antibody described herein and a pharmaceutically acceptable carrier.

Yet other aspects of the invention relate to the use of the isolated antibody or antigen binding fragment described herein in the treatment or diagnosis of diseases.

Yet another aspect of the invention relates to a combination therapy which includes the pharmaceutical composition described herein and a chemotherapeutic agent.

In accordance with the present invention, the pharmaceutical composition may be administered (is administrable) concurrently with the chemotherapeutic agent.

Also in accordance with the present invention, the pharmaceutical composition and the chemotherapeutic agent may be administered (is administrable) at different time intervals.

Further in accordance with the present invention, the chemotherapeutic agent may be conjugated with the antibody or antigen binding fragment.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCL, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), antioxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The antibodies and antigen binding fragments may have therapeutic uses in the treatment of various diseases. In certain instances, the antibodies or antigen binding fragments may interact with cells that express an antigen of interest and induce an immunological reaction by mediating ADCC. In other instances, the antibodies or fragments may block the interaction of the antigen with its protein partners. In yet other instances, the antibodies or fragments may sequester the antigen.

A "chemotherapeutic agent" is a compound useful in the treatment of cancer. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK7; razoxane; sizofiran; spirogermanium; tenuazonic acid; triaziquone; 2,2',2'=-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Antibody Conjugates

The antibody or antigen binding fragment of the present invention may be conjugated with a detectable moiety (i.e., for detection or diagnostic purposes) or with a therapeutic moiety (for therapeutic purposes, e.g., chemotherapeutic agent)

A "detectable moiety" is a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to antibodies and antigen binding fragments thereof of the present invention using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, $^{125}$I, In$^{111}$, Tc$^{99}$, I$^{131}$ and including positron emitting isotopes for PET scanner etc), a nuclear magnetic resonance active label, a luminiscent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

In another exemplary embodiment of the invention, the antibody or antigen binding fragment thereof may be coupled (modified) with a therapeutic moiety (e.g., drug, cytotoxic moiety).

In an exemplary embodiment, the antibodies and antigen binding fragments may comprise a chemotherapeutic agent or cytotoxic agent. For example, the antibody and antigen binding fragments may be conjugated to the chemotherapeutic agent or cytotoxic agent. In addition to those listed elsewhere in the present application, such chemotherapeutic or cytotoxic agents include, but are not limited to, Yttrium-90, Scandium-47, Rhenium-186, Iodine-131, Iodine-125, and many others recognized by those skilled in the art (e.g., lutetium (e.g., Lu$^{177}$), bismuth (e.g., Bi$^{213}$), copper (e.g., Cu$^{67}$)). In other instances, the chemotherapeutic or cytotoxic agent may be comprised of, among others known to those skilled in the art, 5-fluorouracil, adriamycin, irinotecan, taxanes, pseudomonas endotoxin, ricin and other toxins.

Alternatively, in order to carry out the methods of the present invention and as known in the art, the antibody or antigen binding fragment of the present invention (conjugated or not) may be used in combination with a second molecule (e.g., a secondary antibody, etc.) which is able to specifically bind to the antibody or antigen binding fragment of the present invention and which may carry a desirable detectable, diagnostic or therapeutic moiety.

Methods of Treatment

A further aspect of the invention relates to a method of reducing the growth of a cancer cell expressing clusterin or of reducing volume of a tumor comprising clusterin-expressing cells. The method may comprise, for example, administering to a mammal in need an anti-clusterin antibody such as a polyclonal antibody, a monoclonal antibody, a chimeric antibody, a humanized antibody, an isolated human antibody, a hybrid antibody and a fragment thereof.

The method may further comprise administering a chemotherapeutic agent.

The present invention also relates in an additional aspect thereof to a method of treating a disease associated with increased clusterin expression or secretion. The method may comprise administering the humanized or hybrid antibody described herein, the antigen binding fragment described herein or the isolated antibody described herein to a mammal in need.

A mammal in need which would benefit from such method of treatment may include, for example, a mammal having a carcinoma, a mammal having an elevated level of clusterin, a mammal having an elevated level of plasma or blood clusterin, a mammal carrying or susceptible of carrying cells capable of epithelial-to-mesenchymal transition, a mammal having a disease related to an increased level of clusterin (pre-clusterin or secreted clusterin) or of clusterin expression or secretion (including blood or plasma clusterin) etc.

Another aspect of the invention concerns the use of the humanized or hybrid antibody described herein, the antigen binding fragment described herein or the isolated antibody described herein in the manufacture of a medicament for the treatment of a disease associated with clusterin expression or secretion.

Kits and Assays

In yet a further aspect, the present invention provides a kit comprising a vial or vials which may comprise, for example, the humanized or hybrid antibody described herein, the antigen binding fragment described herein or the isolated antibody described. The kit may be used for detection purposes or for therapeutic purposes.

In another exemplary embodiment, the kit may comprise the isolated nucleic acid described herein or the vector described herein. Such kit may find utility for detecting complementary nucleic acids, expressing the protein which it encodes or else.

The present invention therefore also relates to a method of detecting clusterin (pre-clusterin and secreted clusterin) by contacting a sample containing or suspected of containing clusterin with the humanized or hybrid antibody described herein, the antigen binding fragment described herein or the isolated antibody described. Detection is carried out with an apparatus having appropriate sensors which may detect the binding of an antigen to an antibody (e.g., BIAcore™, microplate reader, spectrophotometer, etc.). Such apparatus may be provided with a computer system.

As used herein the term "three-dimensional structure similar to that of or superimposable to" with respect to a variable region means that upon using a computerized model, a specified variable region has a conformation that allows for the antigen binding site to be exposed in a similar manner as another variable region. The variable regions are said to be superimposable when the computerized representation of the variable region amino acids occupies a similar position in space as the corresponding amino acids of another variable region.

As used herein the term "a modeled variable region" means a computerized representation of a variable region that is obtained from known three dimensional structures of closely related antibody variable region.

As used herein the term "non-human" encompasses without limitation rodent (e.g., mouse, rats, etc.), rabbit or nonhuman primate etc.

As used herein the term "non-human complementarity determining region amino acid residues" therefore means that amino acid residues of the complementarity determining region originates from a non-human, typically a rodent such as a mouse.

As used herein the term "non-human parent antibody" therefore encompasses an antibody obtained from a non-human which is used as starting material for humanization procedures.

The term "transforming a host cell" includes several techniques known in the art for transferring or introducing a desired nucleic acid into a host cell. Such techniques include, without limitation, transfection, infection, lipofection, injection, transduction, nucleofection, electroporation, sonoporation, heat shock, magnetofection, etc.

The term "importing" with respect to non-human heavy chain or light chain CDR amino acid residues encompasses physical and computerized methods, e.g., cloning techniques, chemical synthesis of a nucleic acid or protein, computer generated humanized antibodies, etc. As used herein the term "substantially the same" with respect to the number of amino acids, means that a variation of +/−3 amino acids or preferable +/−2 amino acids or even more preferably +/−1 amino acid may be tolerated.

Example 1

Humanization by Design of the Anti-Clusterin Mouse Monoclonal Antibodies

3D Modeling of the Variable Regions of the Mouse 16B5 Monoclonal Antibody.

This task was readily accomplished by mutating 3 light-chain residues and 7 heavy-chain residues in the available crystal structures of two different mouse antibodies (Protein Data Bank (PDB) codes 1Q9Q and 1TY7, respectively) followed by assembly of the light and heavy chains by superimposing the template structures. Part of the CDR-H3 loop was based on another antibody structure (PDB code 1UJ3, a humanized antibody) that also has high sequence similarity to the heavy chain of 16B5 but, unlike the mouse template structure, displays the same length for the CDR-H3 loop. The resulting structure was refined by energy minimization with the AMBER force-field and then used in the subsequent analysis. A good quality of the resulting homology model is expected in this case, given the high homology of the mouse 16B5 sequence to available structural templates. Nonetheless, comparable results were obtained in parallel control homology modeling experiments where we modeled the mouse 16B5 variable region by employing generic 3D homology modeling programs like Modeller or Composer, or antibody-specialized 3D homology modeling as implemented in the WAM software. A representation of the modeled variable regions of the mouse 16B5 antibody is given in FIG. 1.

Characterization of the 16B5 Source Donor (Mouse) Amino-Acid Sequences and Modeled Structure.

This step was carried out to estimate the humanness index, to delineate the CDRs, canonical residues, inter-chain packing (VH/VL interface residues), variable-/constant-region packing (VH/CH and VL/CL interface residues), unusual framework residues, potential N- and O-glycosylation sites, buried residues, Vernier zone residues, and proximity to CDRs. Internet-available resources and local software were used to assess these properties.

Selection of the Best Human Light-Chain and Heavy-Chain Frameworks for the Mouse CDRs.

Selection of the best human light-chain and heavy-chain frameworks was done by standard sequence homology comparison against a local copy of human germline databases (VBASE), against other sequence libraries (Genbank and SwissProt), as well as the set of human framework consensus sequences. BLAST searches were conducted to retrieve sequence matches with highest homology in the framework region only (thus excluding CDRs) while matching the length of the CDR loops. The structures of the human or humanized variable sequences most similar to the 16B5 variable sequences identified from PDB were superimposed onto the modeled structure of the 16B5 variable region for structural comparison. Several most similar human framework sequences were initially retained in order to assess the amino-acid variability at candidate positions for mutation, as well as to provide a pool of suitable framework sequences as backup in the event of affinity loss upon humanization. The closest human framework sequences are aligned to the murine 16B5 sequences in FIG. 2.

Identifying Mouse Framework Residues that can Influence Conformation and Antigen Binding.

Figure 2:
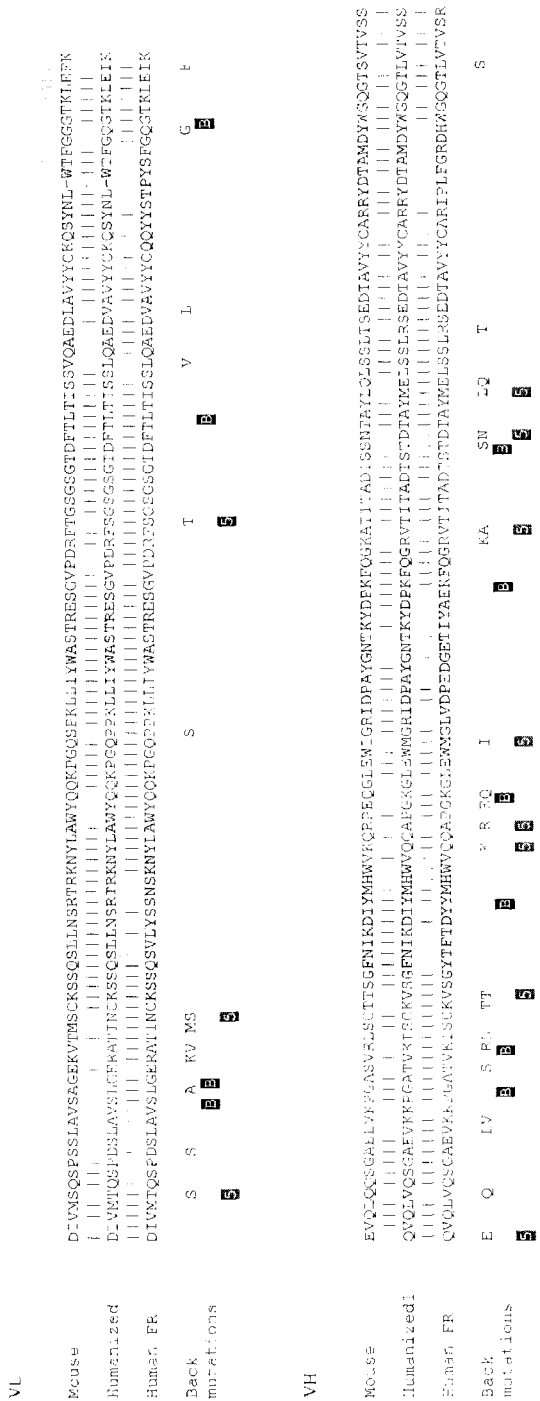
FIG. 2. Sequence alignment of the mouse 16B5, humanized 16B5 and the selected human framework (NCBI database links provided). Kabat numbering is shown at the top. CDRs are highlighted. Candidate residues for back-mutations are highlighted below the sequence alignment according to proximity to CDRs (5: within 5 Angstrom), surface exposure (B: Buried), and contact with the pairing variable domain.

The identification mouse framework residues that can influence conformation and antigen binding is an important step that flags amino-acid residues that should be mutated to the corresponding human sequences with particular care. These residues represent primary candidates for back-mutations to the mouse sequences in case of affinity loss. This is the most difficult and unpredictable step of humanization by design, particularly in the absence of an experimental structure of the antibody-antigen complex. This step relies on the identification of residues in one or more of the following categories: canonical, CDR-H3. Vernier zone, unusual, CDR-proximal (within 5 Å), inter-chain packing, and glycosylation-site residues. These residues might affect antigen-binding site and affinity directly or indirectly. The final humanized sequences of the 16B5 anti-clusterin mAb require 13 framework mutations in the light chain and 22 framework mutations in the heavy chain relative to the murine sequences, while not altering the CDRs regions. Surprisingly, a careful structural and comparative sequence analyses indicated a high probability of retaining high antigen-binding affinity by introducing all these mutations, thus aiming at reaching the highest degree of humanization allowed by the CDR grafting technique (i.e., 100%, excluding CDRs). 3D modeling of the designed humanized antibody supports this prediction. Nonetheless, we have identified candidate residues for back-mutations, including CDR-proximal residues (3 in the light chain and 9 in the heavy chain within 5 Å from CDRs), one light-chain residue in contact with the heavy chain, as well as several buried residues (and hence likely not be immunogenic) that may be converted back to the mouse sequence (4 in the light chain and 6 in the heavy chain). Mutated residues and candidate residues for back-mutations are indicated in FIG. 1 and FIG. 2.

Additional Structural Analysis.

Prior to submitting the humanized sequence for recombinant expression, additional structural analysis included selection of signal peptide, selection of isotype, and analysis of structural compatibility at the variable-/constant-region junctions. In addition, a comparative analysis of inter-chain packing and variable-/constant-region packing between mouse and humanized antibodies indicated that in the case of 16B5 humanization it will be feasible to generate hybrid antibodies combining humanized and chimeric (mouse variable region) chains, i.e., mouse/mouse (M/M), mouse/humanized (M/H), humanized/mouse (H/M) and humanized/humanized (H/H) as light-chain/heavy-chain pairing. The isotype selected for the anti-clusterin antibodies was human IgG2. Human IgG2 do not harbor potent effector functions which is the hallmark of blocking antibodies as those disclosed here. In addition, human IgG2 are less susceptible to proteolytic cleavage which makes provides antibodies of this isotype more stability in vivo.

3D Modeling of the Variable Regions of the Mouse 21B12 Monoclonal Antibody.

Figure 7:
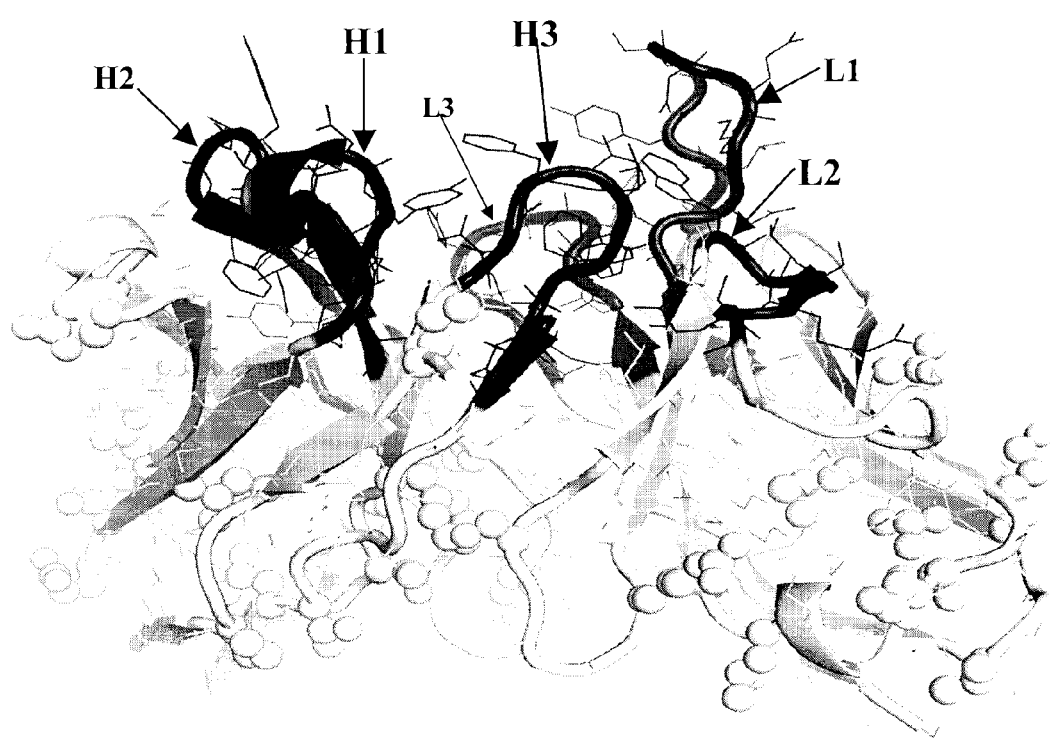
FIG. 7 Homology 3D model of the variable region of the mouse 21B12 anti-clusterin antibody. CDRs are labeled (L1, L2, L3 in the light chain, and H1, H2, H3 in the heavy chain). Mouse framework residues replaced by human framework residues are indicated as sphere models.

Modeling of the 21B12 mouse anti-clusterin antibody was conducted according to the teachings describes above for 16B5. The resulting humanized 21B12 was 100 humanized and required 18 mutations in the heavy chain and 14 mutations in the light chain. Mutated residues and candidate residues for back-mutations are indicated in FIG. 7 and FIG. 8.

Example 2

Kinetic Analysis of Anti-Clusterin Antibodies

The purpose of these investigations is to determine the kinetics parameters of anti-clusterin antibodies. In particular, to determine whether the humanization of the 16B5 and 21B12 anti-clusterin monoclonal antibody affects the kinetics parameters of its binding to human clusterin. To this end, a kinetic analysis method was developed using the BIAcore 3000. Human clusterin was immobilized on a sensor chip. Full length antibodies or Fab fragments were injected and allowed to interact with the immobilized clusterin. This example described the exemplary antibody 16B5 but the 21B12 exemplary antibody was prepared and tested in a similar manner.

Immobilization of Clusterin

HBST (10 mM Hepes pH 7.4, 135 mM NaCl, 3.4 mM EDTA, 0.005% Tween 20) was used as running buffer for all BIAcore experiments. Recombinant monomeric clusterin was immobilized on a CM3 chip with normal amine coupling method at a flow of 5 μl/min. Surface was activated with 35 μl of a mixture of 50 mM NHS/0.2M EDC. Clusterin in 10 mM Na-acetate pH 4.5 was injected until a desired amount was captured (below 60RU). Unreacted esters were deactivated with 35 μl of 1M ethanolamine hydrochloride-NaOH pH8.5. A control surface was prepared by injecting NHS/EDC and ethanolamine in the same manner.

Preparation of Humanized Anti-Clusterin IgG2 Antibodies

Expression vectors containing the cDNAs encoding the light and heavy chain immunoglobulins were expressed in 293 cells using transient transfection methods familiar to those skilled in the art. By virtue of the signal peptides incorporated at the amino-termini of both immunoglobulin chains, the mature IgG2 was harvested from the serum-free culture medium of the cells. Growth of the cells was continued for 5 days post-transfection after which the culture medium was harvested for purification of the IgG2 chimeric monoclonal antibodies. The protein was purified using Protein-A agarose as instructed by the manufacturer (Sigma-Aldrich Canada Ltd., Oakville, ON).

Preparation of Mouse 16B5 and HH 16B5 Fab

Mouse 16B5 IgG was treated with papain at a molar ratio of 1:100 for 4 hours at room temperature. The digestion was stopped by addition of a 4:1 molar ratio of the papain inhibitor E64. Fab fragments were separated from Fc fragments by chromatography on a 1 ml HiTrap Protein G column. The Fab fragments were eluted from the column with 0.1 M glycine, pH 2.7. The pH was neutralized immediately by collection of 1 ml fractions into tubes containing 100 μl of 2 M Tris, pH 9. Fab containing fractions were pooled and concentrated on an Amicon Ultra 4 centrifugal concentrator with a 30 kDa MW cutoff. The samples were passed through a Superose 12 size exclusion column (10× 300 mm) in 20 mM HEPES, pH 7.5, 200 mM NaCl to separate the Fab and F(ab')2 fractions. The Fab-containing fractions were pooled and concentrated on an Amicon Ultra 4 centrifugal concentrator with a 30 kDa MW cutoff.

For preparation of HH 16B5 Fab, the protocol was very similar to that of mouse Fab, except that the digestion time was 20 hours at room temperature and the Fab and Fc fragments were separated on a HiTrap Protein A column instead of a HiTrap Protein G column. The digestion time was increased based on results from a small scale test in an effort to try to eliminate the presence of F(ab')2. The size exclusion profile showed that the longer digestion reduced, but did not eliminate completely, the presence of F(ab')2 fragments. The switch to Protein A rather than Protein G was done to avoid exposure of the Fab fragments to the low pH required to elute the Fab fragments from the Protein G. The Fab fragments flowed through the Protein A column and the Fc fragments were retained by the Protein A. The size exclusion separation was done in PBS instead of HEPES buffer. The same methods were used to prepare 21B12 Fab fragments.

Kinetics Analysis of Mouse 16B5 and HH16B5 and Fab

Kinetics analysis was conducted at a flow of 50 µl/min. Full length antibodies (mouse or humanized) or Fab were diluted in HBST. Concentration range was from 1.953-31.25 nM for the full length antibodies and 15.625-250 nM for the Fab. Each concentration was injected over the clusterin and a control surface for 5 min followed with a 5 min dissociation wash. The clusterin surface was regenerated between each antibody injection with 50 µl of 20 mM HCl.

Kinetics Analysis of Antibodies Binding to Clusterin

FIG. 3 summarizes the results obtained for the determination of the kinetics parameters for 16B5 full length and Fab anti-clusterin antibodies.

The kinetics parameters of the full length humanized 16B5 (HH16B5) is very similar to the kinetics of the full length mouse antibody (16B5), suggesting that the humanization did not affect the binding of the antibody to the clusterin. However, the kinetics parameters of the humanized 16B5 Fab (HH16B5 Fab) is slightly better the kinetics of the Fab mouse antibody (16B5 Fab), again suggesting that the humanization did not affect the binding of the antibody to the clusterin. The $K_D$ of the interaction between immobilized human clusterin and mouse 16B5 or humanized 16B5 is in the low nM range. The method develop can be use to compare the kinetics parameters during the humanization process of anti-clusterin antibodies.

FIG. 9 summarizes the results obtained for the determination of the kinetics parameters for 21B12 full length and Fab anti-clusterin antibodies. As was described for the 16B5, the humanization of 21B12 (HH21B12) resulted in binding parameters that were similar to the parent mouse 21B12 antibody. The $K_D$ of the interaction between immobilized human clusterin and mouse 21B12 or humanized 21B12 is in the low nM range. The method developed can be used to compare the kinetics parameters during the humanization process of anti-clusterin antibodies.

Example 3

Biological Activity of h16B5 in Cell Based Assays

These studies were conducted to compare the biological activity of h16B5 with that of the mouse 16B5. To test the h16B5, two assays were used that had previously shown that blocking clusterin with a monoclonal antibody could reduce the migration and invasion of cancer cell lines.

Figure 4:
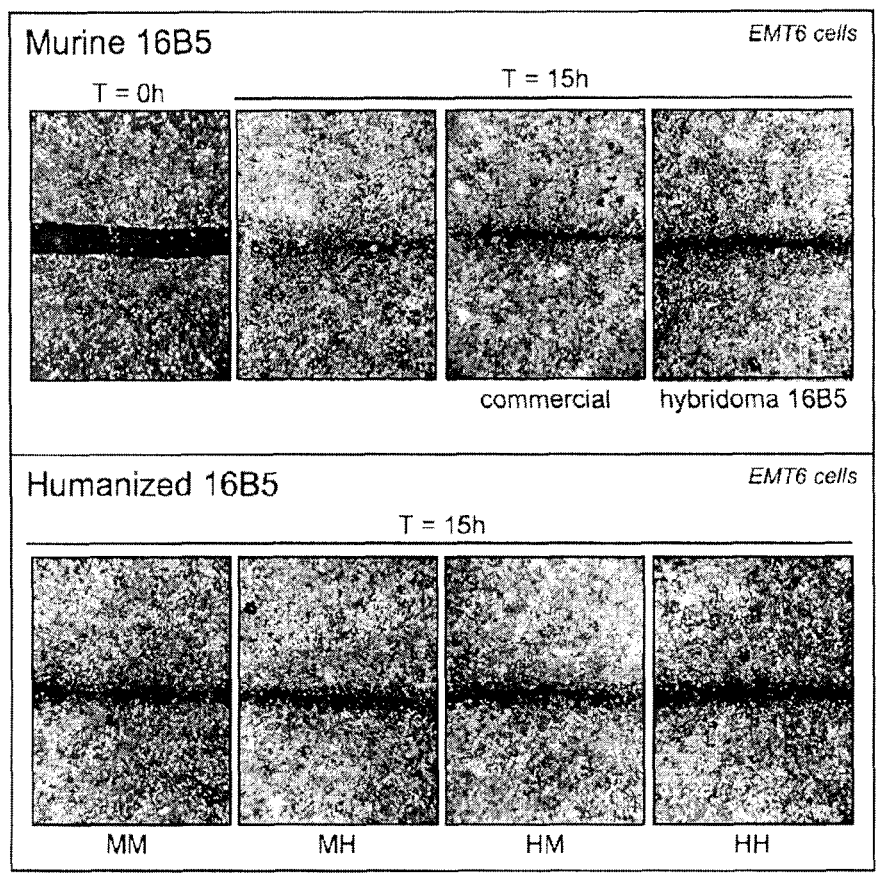
FIG. 4. h16B5 blocks the migration of cancer cell lines. The h16B5 is at least as active as the mouse 16B6 in the scratch assay against mouse mammary carcinoma cells. The figure shows the ability of the antibodies in various configurations to block the migration of the cells in vitro.

To test the activity of anti-clusterin antibodies against cancer cell migration, a standard wound healing, or scratch assay, was used. In this assay, EMT6 cells, a mouse mammary carcinoma cell line, was plated at high density and subjected to wounding by the creation of a scratch in the cell layer. At time 0, a wide denuded area is evident that quickly fills up after incubation of the cells at 37 C for 15 h (see upper left-hand panels in FIG. 4). Incubation of the cells in the presence of either a commercial anti-clusterin polyclonal (C-18, Santa Cruz Biotech, Santa Cruz, Calif.) or the mouse 16B5 purified from the original hybridoma resulted in a reduced number of cells in the denuded area (see upper right-hand panels in FIG. 4, labeled commercial and hybridoma 16B5). Incubation of the wounded EMT6 cells with the chimeric 16B5 (see FIG. 4 lower panel MM), a hybrid antibody containing the chimeric light chain with the humanized heavy chain (see FIG. 4 lower panel MH), a hybrid antibody containing the chimeric heavy chain with the humanized light chain (see FIG. 4 lower panel HM), or the complete humanized 16B5 (see FIG. 4 lower panel HH) also resulted in blockage of migration of the cells into the denuded area. In fact, the humanized 16B5 appeared to be the most effective inhibitor. Additionally, the ability of the chimeric and the mouse-human hybrid antibodies to inhibit migration shows that interaction with clusterin was the same irrespective of which immunoglobulin chain was contained in the 16B5 antibody.

Figure 5:
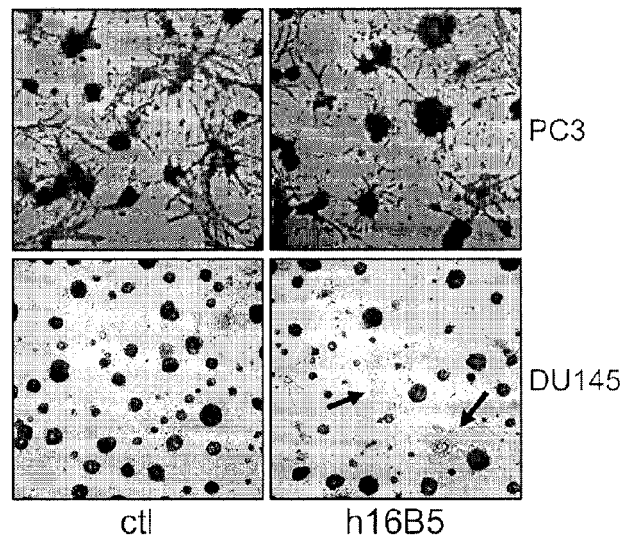
FIG. 5. Inhibition of h16B5 reduces the invasiveness of human prostate cancer cells. The bottom of 12-well plates was covered with 200 µL Growth factor reduced matrigel (Becton Dickinson). Cells ($2.5 \times 10^4$) were resuspended in 200 µL matrigel, which was layered on top of this, and finally 500 µL of cell specific growth medium was added on top of the matrigel. h16B5 was added to every layer of matrigel as well as the medium in a concentration of 8 µg/mL. Plates were incubated at 37° C. for up to 3 weeks during which the growth medium (+/−h16B5) was replenished weekly. The arrows indicate the areas of epithelial-like cells.

We then determined whether other cell lines such as the human prostate PC3 and DU145 cell lines, which secrete various levels of endogenous clusterin, could be affected in their invasive behavior and growth by the h16B5. When seeded in Matrigel (FIG. 5, upper left hand panel), the PC3 tumor cell line displayed a stellate morphology with protrusions sprouting into the Matrigel, a feature that has been correlated with increased invasive potential (Thompson et al., 1992). Treatment with h16B5 (FIG. 5, upper right hand panel) significantly reduced this stellate morphology strongly suggesting that clusterin secretion contributes to the invasive phenotype of the PC3 cells. DU145 cells did not display the stelate morphology observed in the PC3 cells, but rather formed sphere-like structures in Matrigel (FIG. 5, lower left hand panel), which seemed to be smaller and fewer in number in the presence of h16B5 (FIG. 5, lower right hand panel). These results show that the ability of the h16B5 to reduce the invasive potential of cancer cell lines is comparable to the original mouse 16B5 and shows that the humanization process did not alter the ability of the antibody to interact with and block the activity of secreted clusterin.

Figure 11:
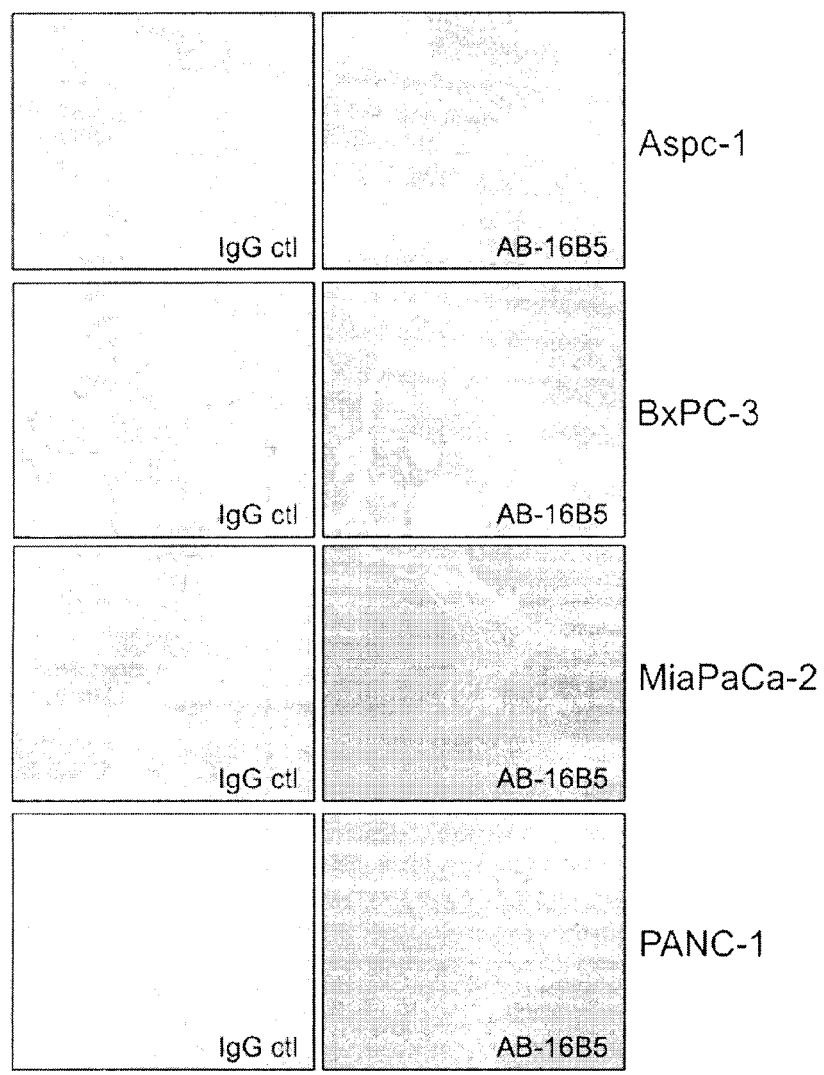
FIG. 11. Clusterin is expressed in human pancreatic tumors. Tumors derived from pancreatic cancer cell lines (as indicated) were grown in SCID mice, harvested, fixed in formalin, sections and examined using immunohistochemistry with h16B5. Positive staining was visualized by standard methods using a HRP-conjugated secondary antibody. The negative control was performed under identical conditions with an isotype control antibody.
Figure 12:
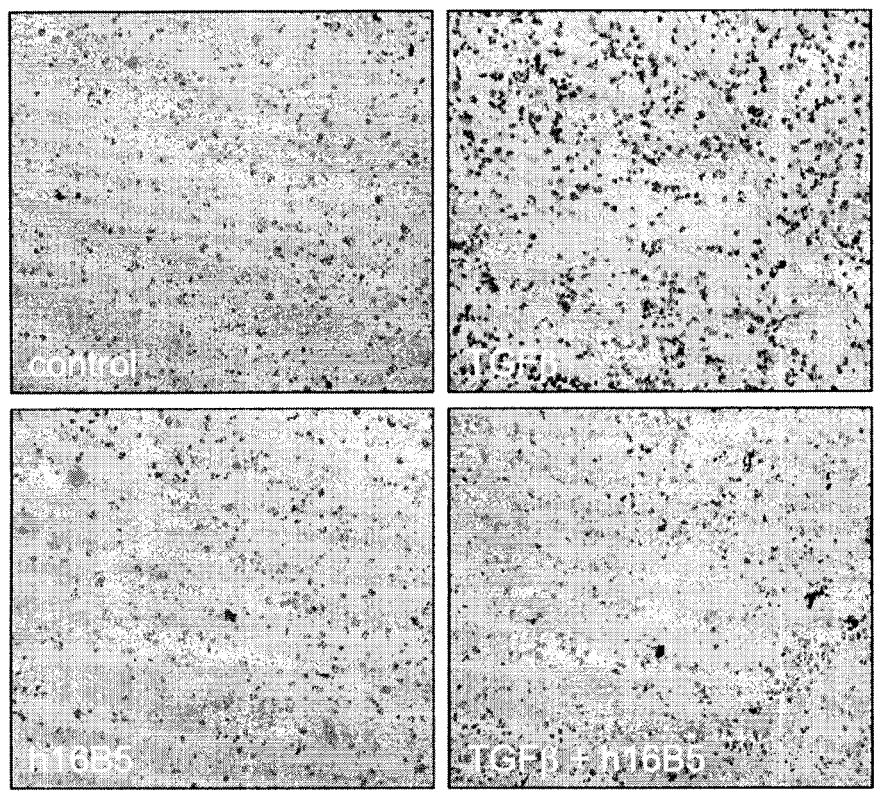
FIG. 12. H16B5 inhibits the migration of pancreatic cancer cell lines. PANC-1 cells were seeded in serum-free medium in the upper chamber of a 24-well Transwell plate containing a Matrigel barrier. The lower wells were filled with medium containing 10% FBS as a chemo-attractant. After a 24 h incubation in the presence or absence of TGFβ and/or h16B5 (as indicated), the number of cells in the Matrigel layer were stained and counted.

Tumors derived from 4 different human pancreatic cell lines were obtained which were fixed in formalin, embedded in paraffin, and section on glass slides. Immunohistochemistry was conducted with h16B5 antibody to determine if tumors derived from this cancer indication expressed clusterin. The tumors were derived from Aspc-1, BxPC-3, PANC-1, and MiaPaCa-2 all of which were derived from pancreatic cancer patients (ATCC, Manassas, Va.). Paraffin-embedded epithelial pancreatic tumor samples were placed on glass slides and fixed for 15 min at 50° C. Deparaffinization was conducted by treating 2× with xylene followed by dehydration in successive 5 min washes in 100%, 80%, and 70% ethanol. The slides were washed 2× in PBS for 5 min and treated with antigen retrieval solution (citrate-EDTA) to unmask the antigen. Endogenous peroxide reactive species were removed by incubating slides with $H_2O_2$ in methanol and blocking was performed by incubating the slides with serum-free blocking solution (Dakocytomation) for 20 min at room temperature. The primary mAb (a control IgG or h16B5) was added at 5 µg/ml for 1 h at room temperature. H16B5-reactive clusterin was detected by incubating with biotin-conjugated human anti-kappa followed by streptavidin-HRP tertiary. antibody. Positive staining was revealed by treating the slides with DAB-hydrogen peroxide substrate for less than 5 min and subsequently counterstained with hematoxylin. As shown in FIG. 11, all four tumors stained positive for clusterin expression (see right hand panels in FIG. 11). Interestingly, the tumors that were known to be resistant to chemotherapy (PANC-1 and MisPaCa-2) contained the highest level of secreted clusterin. The PANC-1 cell line was cultured and grown in Matrigel as described for the prostate cancer cell lines (see above). The cells were stimulated with TGFβ, and inducer of the epithelial-to-mesenchymal transition and a growth factor that causes the cells to migrate across the membrane into the Matrigel (see FIG. 12, upper right hand panel). When the stimulated cells were treated with h16B5, migration was severely inhibited (FIG. 12, lower right hand panel). This result indicates that h16B5 can block the migration of pancreatic cancer cells and shows that the antibody has the potential to be therapeutically active in this cancer indication as well.

Example 4

Biological Activity of h16B5 in Animal Models of Cancer

Figure 6:
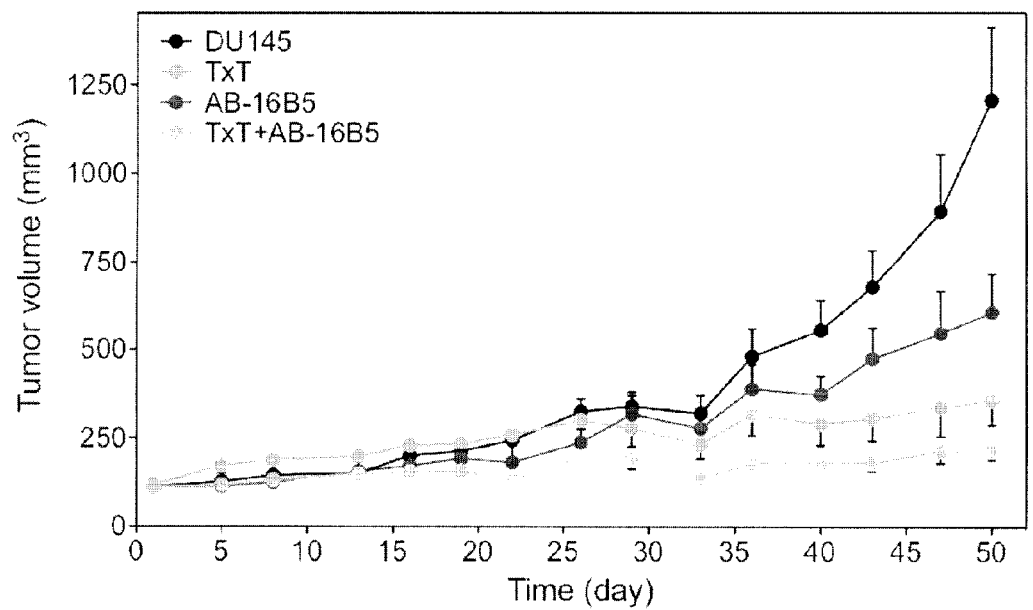
FIG. 6. Treatment of prostate cancer tumors with h16B5 reduces the growth of the tumors and increases their response to chemotherapy. DU145 prostate cancer cells ($2 \times 10^6$) were implanted s.c. into SCID mice and allowed to grow until the tumor sizes were approximately 100 mm3. Tumors were measured bi-weekly with a digital caliper and tumor volumes were calculated as L×W×H. Each group contained 8 animals that were randomized prior to the beginning off the treatments. The results were expressed as mm³±SEM. The P values were calculated using the Student's T test.

These studies were performed to measure the in vivo efficacy of h16B5 in models of human cancer. Antisense oligonucleotides and small interfering RNAs targeting clusterin have been reported to induce apoptosis and chemosensitivity in vitro in prostate cancer xenografts [1-4]. The model system that was used comprised the DU145 human prostate cancer cell line that is androgen-insensitive and represents one of the most well characterized models for this disease. Thus, 2 million cells were implanted sub-cutaneously into the flanks of SCID mice and the tumors were allowed to grow to approximately 100 mm$^3$. Starting on day 1, h16B5 was injected intra-peritoneally (i.p.) at a dosage of 5 mg/kg and from day 4, taxotere (TxT) was injected i.p. at a dosage of 10 mg/kg. The h16B5 injections were continued twice per week while the TxT was administered weekly. As depicted in FIG. 6, the growth of the (primary) tumors was significantly reduced in the animals that received h16B5 treatments compared to the control. This effect occurred both in the monotherapy group (compare control with h16B5, P=0.0104) and in the combination group with TxT (compare TxT with h16B5+TxT, P=0.0395). This result shows that blocking clusterin with the h16B5 causes tumor growth reduction and increases the chemo-sensitivity of the tumors for TxT.

A second prostate cancer model study was conducted in a different tumor model by implanting PC-3 prostate cancer cells. PC-3 cells are also hormone-insensitive but are documented as being slightly more invasive than the DU145 cells. As was described above, the cells were implanted sub-cutaneously in SCID mice and treatments were initiated when the tumors reached a volume of approximately 100 mm$^3$ (designated day 1). The h16B5 injections were administered i.p. on day 1 at 5 mg/kg and continued twice per week thereafter whereas a single TxT injection at 10 mg/kg was administered i.p. on day 5. This modification in the TxT schedule was performed because it was found that PC-3 cells are significantly more susceptible to this chemotherapeutic drug compared to the DU145 tumors.

Figure 10:
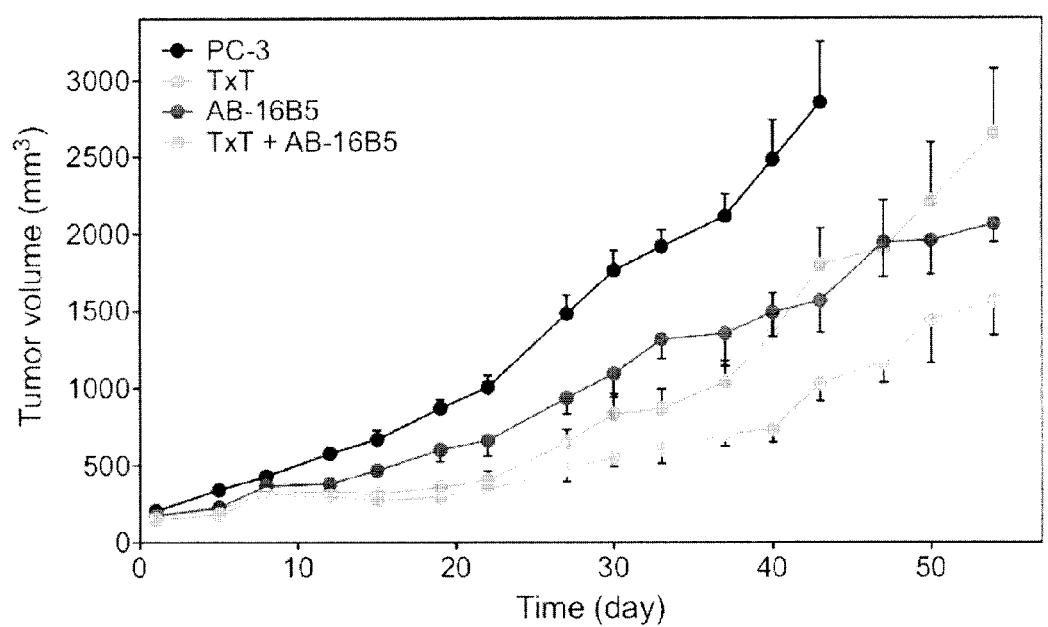
FIG. 10. h16B5 inhibits the growth of PC-3 prostate tumors. PC-3 prostate cancer cells ($2 \times 10^6$) were implanted s.c. into SCID mice and allowed to grow until the tumor sizes were approximately 100 mm³. Tumors were measured bi-weekly with a digital caliper and tumor volumes were calculated as L×W×H. Each group contained 8 animals that were randomized prior to the beginning off the treatments. The results were expressed as mm³±SEM.

The results of this study are depicted in FIG. 10. As before, it was observed that the tumors in the animals that received h16B5 alone had an almost immediate response to the antibody compared to the untreated animals. The significant decrease in the average tumor size in the h16B5 treatment group was found to result in a 37% reduction compared to the control group on day 43. Survival was also monitored and it was observed that on the day that there were no remaining animals in the control group (day 43), greater than 60% of the mice remained alive in the AB-16B5 treatment group. This increase in overall survival translated into a 47% increase in the animals that received h16B5.

The cytotoxic effect of TxT against prostate cancer cells was observed but the tumors appeared to recover from this treatment approximately 18 days following the injection. The growth of the tumors in the TxT group even surpassed that of the tumors in the group that received the AB-16B5 (see day 50, FIG. 10). However, the combination of h16B5 with TxT significantly slowed the growth of the tumors resulting in tumors that were 41% smaller compared to the TxT alone group. Again, the presence of h16B5 extended the survival of the animals. Taken together, the results from these in vivo studies indicate that the h16B5 humanized antibody that inhibits the function of secreted clusterin in tumors can significantly slow the growth of solid tumors.

Example 5

H16B5 Inhibits the Internalization of Secreted Clusterin in Cancer Cells

The results disclosed above indicate that induction of the epithelial-to-mesenchymal transition (EMT) leads to the secretion of clusterin by cancer cells. Additionally, our data also showed that clusterin secreted by these cancer cells is a potent inducer of EMT. These findings imply that secreted clusterin is mediating this effect either indirectly by interacting with other tumor-associated factors in the extracellular matrix or directly by interacting with a receptor on the cell surface of cancer cells. Although secreted clusterin present in normal serum is known to associate with many different proteins such as members of the complement cascade, leptin, various apolipoproteins, the presence of protein partners for secreted clusterin in cancer cells or in the tumor micro-environment remains relatively unexplored. Some examples include a published report by Jo and coworkers (Jo et al., 2008) showed that tumor-secreted clusterin associated with IGF-1 under conditions of stress induced by serum deprivation. In addition, clusterin contained in prostate cancer cell lines was found to interact with a protein called COMMD1 (Zoubeidi et al., 2010). This interaction resulted in increased activation of NF-kappaB-related pathways which in turn promoted prostate cancer cell survival. These findings begin to elucidate some of the ways secreted clusterin might contribute to tumorigenesis but the molecular mechanism for how it promotes EMT is unknown.

Figure 13:
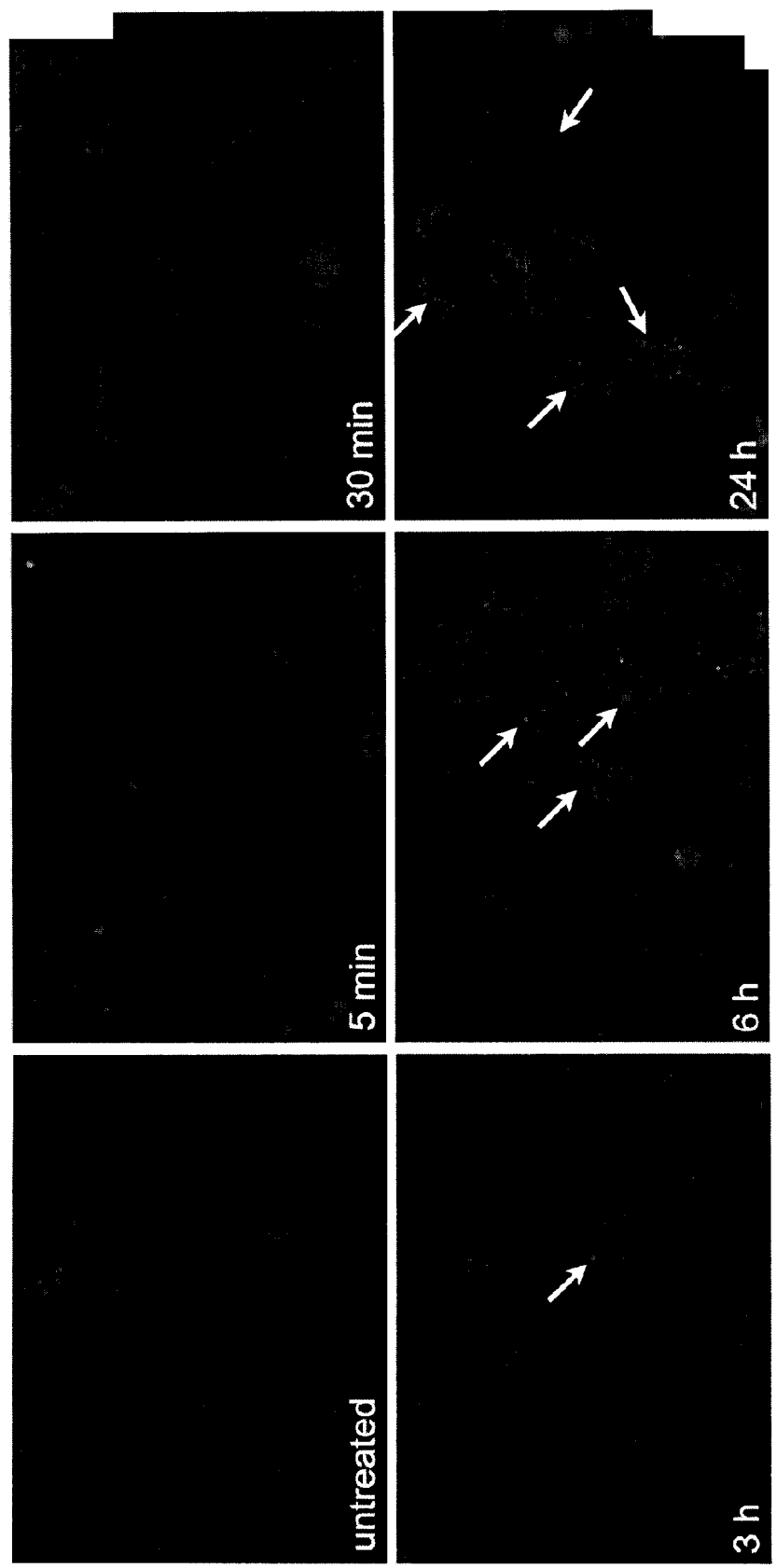
FIG. 13. Secreted clusterin is internalized in cancer cells. Recombinant human clusterin was expressed in 293-6E cells, purified, and labelled with Alexa Fluor 488 using a commercial labelling kit (Invitrogen). BRI-JM01 mouse mammary carcinoma cells were seeded on coverslips and treated with 250 ng/ml of labelled secreted clusterin. At the indicated times, the cells were washed with ice-cold PBS and fixed in 2% paraformaledyhde. The slides were mounted with Antifade Gold and images were generated with a fluorescence microscope.

In order to begin to address this question, cell-based experiments were undertaken to determine if secreted clusterin interacted with cancer cells directly or via other secreted factors in the cell medium. In order to measure this, secreted clusterin was fluorescently labelled and incubated with BRI-JM01 mouse mammary carcinoma cells. It was found that after approximately 24 hours of treatment, that the fluorescence signal was contained inside the cells. Analysis of these cells over shorter time points revealed that the fluorescently labelled secreted clusterin was internalized by the cells (see FIG. 13). As shown, the internalization increases over time in manner that is consistent with a receptor-mediated endocytic pathway. Furthermore, the punctate and perinuclear pattern of staining that results after 24 hours (see white arrows in FIG. 13) that is often observed in proteins that are internalized along the endosomal pathway. Similar results were observed in DU145 human prostate cancer cells.

Figure 14:
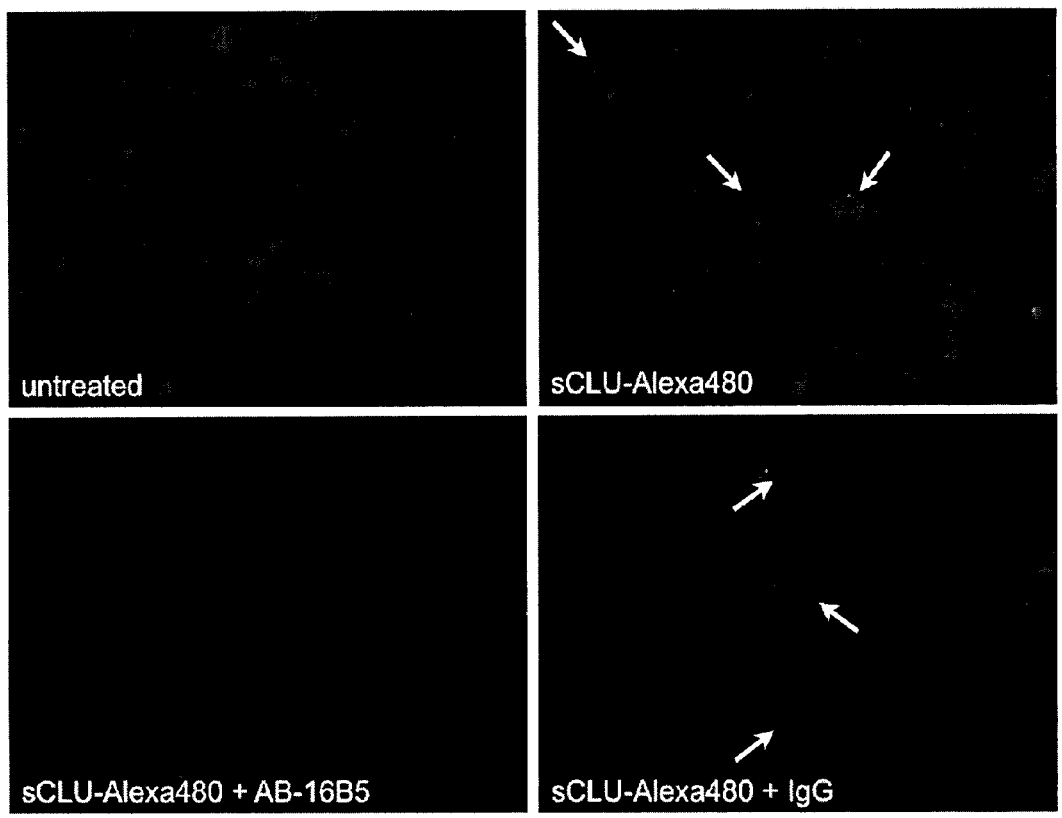
FIG. 14. H16B5 inhibits the internalization of secreted clusterin in cancer cells. The experiment was performed as described for FIG. 13. H16B5 was added at 10 µg/ml.

This secreted clusterin internalization was further examined by testing if h16B5 could block this activity. The cells were treated with secreted clusterin-Alexa480 in the presence of h16B5 or an isotype control IgG. As shown, in FIG. 14, the internalization of secreted clusterin into JM01 cells was blocked by the addition of h16B5. Internal perinuclear staining of secreted clusterin was still observed in the cells treated with the control IgG (see white arrows in FIG. 14).

Taken together, these results which show that this the internalization of secreted clusterin can be inhibited by the addition of h16B5 suggests that this might be one of the mechanism by which the antibody prevents secreted clusterin from mediating EMT in cancer cells.

The experiments described herein may be carried out to determine how specific mutations in the amino acid sequence of an antibody (e.g., in the variable region(s), the constant region, the framework region or in the CDR(s)) affect the biological activity of the antibody. For example, one or more mutations may be introduced in the framework region of the variable light chain or variable heavy chain of h16B5 (or in the murine 16B5) and tumor growth may be assed as described herein.

Binding of variant antibodies and antigen binding fragments to human or murine clusterin may be tested by several methods known in the art such as, for example, ELISA, Western blot, surface plasmon resonance, etc.

Example 6

Anti-Clusterin Antibodies May Bind to Clusterin Variants

The antibodies and antigen binding fragments of the present invention bind to both the human and murine form of clusterin. These two proteins share 77% amino acid sequence identity and 89% similarity (see FIG. 15). By comparing the amino acid sequence of the murine and human form, one may understand that the antibody probably binds a linear or a conformational epitope preserved in both proteins. It is expected that the antibodies and antigen binding fragments may bind to other naturally occurring variants as well as synthetic variants (including recombinant proteins) having at least 75% amino acid identity (including 80%, 85%, 90%, 95%, 99%, 100%) with human or murine clusterin. For example, the antibodies and antigen binding fragments may bind a clusterin variant having an amino acid sequence comprising SEQ ID NO.:56 (wherein + represent an amino acid substitution, such as for example a conservative amino acid substitution) or SEQ ID NO.:57.

Figure 16:
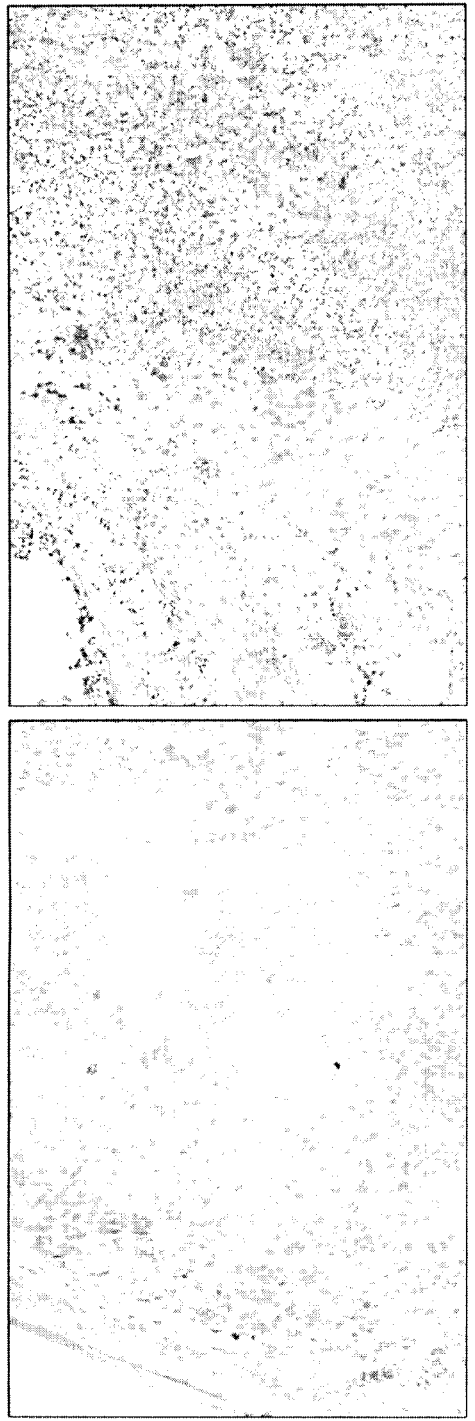
FIG. 16. Shows the binding of h16B5 (labeled as AB-16B5 in the figure) to murine clusterin that is expressed in fixed frozen sections generated from 4T1 mouse mammary tumors. The experiment was performed using immunohistochemistry and detection was accomplished using a HRP-conjugated secondary antibody.

The present invention shows that anti-clusterin antibodies target clusterin that is expressed in human tumors. To demonstrate that the interaction of the anti-clusterin antibodies, such as h16B5, with murine tumor clusterin, frozen sections prepared from 4T1 mouse mammary tumors were incubated with h16B5. Briefly, the frozen sections were fixed with ice-cold acetone for 10 minutes and non-specific binding was blocked with a reagent supplied in a commercially available kit (Dako Canada, Inc., Burlington, ON). H16B5 was incubated with the mouse tumor section for 1 h at a concentration of 5 µg/ml. After washing, specific staining was revealed by incubating with a HRP-conjugated anti-human IgG. A control sample was processed in an identical manner with a human isotype control IgG. As shown in FIG. 16, h16B5 detected murine clusterin in the 4T1 tumors (see right panel, labeled as 4T1-AB-16B5) as evidenced by the brown staining resulting from the horseradish peroxidase coloring. The control antibody did not reveal any antigens (see left panel, labeled as 4T1-ctl). This result demonstrates that anti-clusterin antibodies, as exemplified by h16B5, interact with murine clusterin that is expressed in mouse tumors. In addition, other studies using immunofluorescence showed that h16B5 detected murine clusterin that was expressed in BRI-JM01 cells, another mouse mammary carcinoma cell line.

Binding of the antibodies and antigen binding fragments of the present invention to naturally occurring variant or synthetic variants of clusterin may also be tested by methods known in the art, including for example, the above mentioned methods.

The CLU gene is conserved in human, chimpanzee, dog, cow, mouse, rat, chicken and zebrafish. Testing of the antibodies and antigen binding fragments in these models is encompassed by the present invention.

REFERENCES

1. Gleave, M. E., et al., *Use of antisense oligonucleotides targeting the antiapoptotic gene, clusterin/testosterone-repressed prostate message 2, to enhance androgen sensitivity and chemosensitivity in prostate cancer*. Urology, 2001. 58(2 Suppl 1): p. 39-49.
2. Trougakos, I. P., et al., *Silencing expression of the clusterin/apolipoprotein j gene in human cancer cells using small interfering RNA induces spontaneous apoptosis, reduced growth ability, and cell sensitization to genotoxic and oxidative stress*. Cancer Res, 2004. 64(5): p. 1834-42.
3. Gleave, M. and H. Miyake, *Use of antisense oligonucleotides targeting the cytoprotective gene, clusterin, to enhance androgen-and chemo-sensitivity in prostate cancer*. World J Urol, 2005. 23(1): p. 38-46.
4. Springate, C. M., et al., *Efficacy of an intratumoral controlled release formulation of clusterin antisense oligonucleotide complexed with chitosan containing paclitaxel or docetaxel in prostate cancer xenograft models*. Cancer Chemother Pharmacol, 2005. 56(3): p. 239-47.
5. Jo, H., Jia, Y., et al., *Cancer cell-derived clusterin modulates the phosphatidylinositol-3'-kinase-Akt pathway through attenuation of insulin-like growth factor 1 during serum deprivation*. Mol. Cell. Biol. 2008. 28:4285-4299.
6. Zoubeidi, A., ettinger, S. et al., *Clusterin facilitates COMMD1 and 1-kappaB degradation to enhance NF-kappaB activity in prostate cancer cells. Mol. Cancer Res.* 2010, 8:119-130.

The invention claimed is:

1. A method of reducing the growth of a cancer cell expressing clusterin or of reducing volume of a tumor comprising cells expressing or secreting clusterin, the method comprising administering an antibody or an antigen binding fragment thereof capable of specific binding to clusterin to a mammal in need thereof, wherein the antibody or antigen binding fragment thereof comprises:

a. a light chain variable region as set forth in SEQ ID NO.:8 and a heavy chain variable region as set forth in SEQ ID NO.:7;

b. a light chain variable region as set forth in SEQ ID NO.:8 and a heavy chain variable region as set forth in SEQ ID NO.:29 or;

c. a light chain variable region as set forth in SEQ ID NO.:25 and a heavy chain variable region as set forth in SEQ ID NO.:7.

2. The method of claim 1, wherein the antibody or antigen binding fragment thereof comprises a light chain variable region as set forth in SEQ ID NO.:8 and a heavy chain variable region as set forth in SEQ ID NO.:7.

3. The method of claim 1, wherein the antibody or antigen binding fragment thereof comprises a light chain as set forth in SEQ ID NO.:10 and a heavy chain as set forth in SEQ ID NO.:9.

4. The method of claim 1, wherein the mammal in need receives chemotherapy.

5. A method of treating carcinoma, the method comprising administering an antibody or an antigen binding fragment thereof capable of specific binding to clusterin to a mammal in need, wherein said antibody or antigen binding fragment thereof comprises:

a. a light chain variable region as set forth in SEQ ID NO.:8 and a heavy chain variable region as set forth in SEQ ID NO.:7;
b. a light chain variable region as set forth in SEQ ID NO.:8 and a heavy chain variable region as set forth in SEQ ID NO.:29 or;
c. a light chain variable region as set forth in SEQ ID NO.:25 and a heavy chain variable region as set forth in SEQ ID NO.:7.

6. The method of claim 5, wherein the antibody or antigen binding fragment thereof comprises a light chain variable region as set forth in SEQ ID NO.:8 and a heavy chain variable region as set forth in SEQ ID NO.:7.

7. The method of claim 5, wherein the antibody or antigen binding fragment thereof comprises a light chain as set forth in SEQ ID NO.:10 and a heavy chain as set forth in SEQ ID NO.:9.

8. The method of claim 5 wherein the mammal in need receives chemotherapy.

* * * * *

SEQUENCE LISTING

<160> NUMBER OF SEQ ID NOS: 58

<210> SEQ ID NO 1
<211> LENGTH: 11
<212> TYPE: PRT

-continued

```
<213> ORGANISM: Artificial Sequence
<220> FEATURE:
<223> OTHER INFORMATION: 16B5 CDRH1

<400> SEQUENCE: 1

Thr Gly Phe Asn Ile Lys Asp Ile Tyr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: 16B5 CDRH2

<400> SEQUENCE: 2

Arg Ile Asp Pro Ala Tyr Gly Asn Thr Lys Tyr Asp Pro Lys Phe Gln
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: 16B5 CDRH3

<400> SEQUENCE: 3

Arg Tyr Asp Thr Ala Met Asp Tyr
1               5

<210> SEQ ID NO 4
<211> LENGTH: 17
<212> TYPE: PRT
<213> ORGANISM: Artificial Sequence
<220> FEATURE:
<223> OTHER INFORMATION: 16B5 CDRL1

<400> SEQUENCE: 4

Lys Ser Ser Gln Ser Leu Leu Asn Ser Arg Thr Arg Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: 16B5 CDRL2

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: 16B5 CDRL3

<400> SEQUENCE: 6

Lys Gln Ser Tyr Asn Leu Trp Thr
1               5
```

```
<210> SEQ ID NO 7
<211> LENGTH: 117
<212> TYPE: PRT
<213> ORGANISM: Artificial Sequence
<220> FEATURE:
<223> OTHER INFORMATION: 16B5 Humanized heavy chain variable region

<400> SEQUENCE: 7

Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met His Trp Val Gln Gln Ala Pro Gly Lys Gly Leu Glu Trp Met
        35                  40                  45

Gly Arg Ile Asp Pro Ala Tyr Gly Asn Thr Lys Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Asp Thr Ala Met Asp Tyr Trp Gly Gln Gly Thr Leu
            100                 105                 110

Val Thr Val Ser Ser
        115

<210> SEQ ID NO 8
<211> LENGTH: 112
<212> TYPE: PRT
<213> ORGANISM: Artificial Sequence
<220> FEATURE:
<223> OTHER INFORMATION: 16B5 Humanized light chain variable region

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gln Gly Thr Lys Leu Glu Ile Lys
            100                 105                 110

<210> SEQ ID NO 9
<211> LENGTH: 443
<212> TYPE: PRT
<213> ORGANISM: Artificial Sequence
<220> FEATURE:
<223> OTHER INFORMATION: Complete heavy chain immunoglobulin sequence
      for h16B5

<400> SEQUENCE: 9

Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
```

```
                    20                  25                  30
Tyr Met His Trp Val Gln Gln Ala Pro Gly Lys Gly Leu Glu Trp Met
            35                  40                  45
Gly Arg Ile Asp Pro Ala Tyr Gly Asn Thr Lys Tyr Asp Pro Lys Phe
 50                  55                  60
Gln Gly Arg Val Thr Ile Thr Ala Asp Thr Ser Thr Asp Thr Ala Tyr
 65                  70                  75                  80
Met Glu Leu Ser Ser Leu Arg Ser Glu Asp Thr Ala Val Tyr Tyr Cys
                85                  90                  95
Ala Arg Arg Tyr Asp Thr Ala Met Asp Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
            195                 200                 205
Thr Lys Val Asp Lys Thr Val Glu Arg Lys Cys Cys Val Glu Cys Pro
            210                 215                 220
Pro Cys Pro Ala Pro Pro Val Ala Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Gln Phe Asn
            260                 265                 270
Trp Tyr Val Asp Gly Val Glu Val His Asn Ala Lys Thr Lys Pro Arg
            275                 280                 285
Glu Glu Gln Phe Asn Ser Thr Phe Arg Val Val Ser Val Leu Thr Val
            290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
            435                 440
```

<210> SEQ ID NO 10
<211> LENGTH: 217
<212> TYPE: PRT
<213> ORGANISM: Artificial Sequence
<220> FEATURE:
<223> OTHER INFORMATION: Complete light chain immunoglobulin sequence
      for h16B5

<400> SEQUENCE: 10

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gln Gly Thr Lys Leu Glu Ile Lys
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 11
<211> LENGTH: 10
<212> TYPE: PRT
<213> ORGANISM: Artificial Sequence
<220> FEATURE:
<223> OTHER INFORMATION: 21B12 CDRH1

<400> SEQUENCE: 11

```
Gly Tyr Thr Phe Thr Asn Tyr Gly Met His
1               5                   10
```

<210> SEQ ID NO 12
<211> LENGTH: 17
<212> TYPE: PRT
<213> ORGANISM: Artificial Sequence
<220> FEATURE:
<223> OTHER INFORMATION: 21B12 CDRH2

<400> SEQUENCE: 12

```
Trp Ile Asn Thr Tyr Thr Gly Glu Pro Thr Tyr Ala Asp Asp Phe Lys
1               5                   10                  15
```

Gly

<210> SEQ ID NO 13
<211> LENGTH: 9
<212> TYPE: PRT
<213> ORGANISM: Artificial Sequence
<220> FEATURE:
<223> OTHER INFORMATION: 21B12 CDRH3

<400> SEQUENCE: 13

Asp Gly Phe Leu Tyr Phe Phe Asp Tyr
1               5

<210> SEQ ID NO 14
<211> LENGTH: 17
<212> TYPE: PRT
<213> ORGANISM: Artificial Sequence
<220> FEATURE:
<223> OTHER INFORMATION: 21B12 CDRL1

<400> SEQUENCE: 14

Lys Ser Ser Gln Ser Leu Leu Tyr Ser Ser Asn Gln Lys Asn Tyr Leu
1               5                   10                  15

Ala

<210> SEQ ID NO 15
<211> LENGTH: 7
<212> TYPE: PRT
<213> ORGANISM: Artificial Sequence
<220> FEATURE:
<223> OTHER INFORMATION: 21B12 CDRL2

<400> SEQUENCE: 15

Trp Ala Ser Thr Arg Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: 21B12 CDRL3

<400> SEQUENCE: 16

Gln Gln Tyr Tyr Ile Tyr Pro Arg Thr
1               5

<210> SEQ ID NO 17
<211> LENGTH: 118
<212> TYPE: PRT
<213> ORGANISM: Artificial Sequence
<220> FEATURE:
<223> OTHER INFORMATION: 21B12 humanized heavy chain variable region

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met His Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

-continued

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Gly Phe Leu Tyr Phe Phe Asp Tyr Trp Gly Gln Gly Thr
            100                 105                 110

Leu Val Thr Val Ser Ser
        115

<210> SEQ ID NO 18
<211> LENGTH: 113
<212> TYPE: PRT
<213> ORGANISM: Artificial Sequence
<220> FEATURE:
<223> OTHER INFORMATION: 21B12 humanized light chain variable region

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ile Tyr Pro Arg Thr Phe Gly Gln Gly Thr Lys Leu Glu Ile
            100                 105                 110

Lys

<210> SEQ ID NO 19
<211> LENGTH: 444
<212> TYPE: PRT
<213> ORGANISM: Artificial Sequence
<220> FEATURE:
<223> OTHER INFORMATION: Complete heavy chain immunoglobulin sequence
      for h21B12

<400> SEQUENCE: 19

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Gly Phe Leu Tyr Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

```
Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Asn Phe Gly Thr Gln Thr Tyr Thr Cys Asn Val Asp His Lys Pro Ser
                195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 20
<211> LENGTH: 220
<212> TYPE: PRT
<213> ORGANISM: Artificial Sequence
<220> FEATURE:
<223> OTHER INFORMATION: Complete light chain immunoglobulin sequence
      for h21B12

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
```

```
              35                  40                  45
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ile Tyr Pro Arg Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 21
<211> LENGTH: 1389
<212> TYPE: DNA
<213> ORGANISM: Artificial Sequence
<220> FEATURE:
<223> OTHER INFORMATION: Complete nucleotide sequence of the heavy chain
      of h16B5

<400> SEQUENCE: 21
atggactgga cctggcggat cctgttcctg gtggccgctg ctaccggcac ccacgcccag      60
gtgcagctgg tgcagtctgg cgccgaggtg aagaagcctg gcgccaccgt caagatcagc    120
tgcaaggtgt ccggcttcaa catcaaggac atctacatgc actgggtgca gcaggctcca    180
ggcaagggac tggagtggat gggccggatc gaccctgcct acggcaacac caagtacgac    240
cctaagttcc agggccgggt gaccatcacc gccgacacct ccaccgacac cgcctacatg    300
gaactgtcct ccctgcggtc cgaggacacc gccgtgtact actgcgcccg agatacgac     360 accgccatgg attactgggg ccagggcacc ctggtgaccg tgtcctccgc ttccaccaag    420
ggcccatcgg tcttcccccct ggcgccctgc tccaggagca cctccgagag cacagcggcc   480
ctgggctgcc tggtcaagga ctacttcccc gaaccggtga cggtgtcgtg gaactcaggc    540
gctctgacca gcggcgtgca caccttccca gctgtcctac agtcctcagg actctactcc    600
ctcagcagcg tggtgaccgt gccctccagc aacttcggca cccagaccta cacctgcaac    660
gtagatcaca agcccagcaa caccaaggtg gacaagacag ttgagcgcaa atgttgtgtc    720
gagtgcccac cgtgcccagc accacctgtg gcaggaccgt cagtcttcct cttccccca    780 aaacccaagg acaccctcat gatctcccgg acccctgagg tcacgtgcgt ggtggtggac    840
gtgagccacg aagaccccga ggtccagttc aactggtacg tggacggcgt ggaggtgcat    900
aatgccaaga caaagccacg ggaggagcag ttcaacagca cgttccgtgt ggtcagcgtc    960
ctcaccgttg tgcaccagga ctggctgaac ggcaaggagt acaagtgcaa ggtctccaac   1020
```

```
aaaggcctcc cagcccccat cgagaaaacc atctccaaaa ccaaagggca gccccgagaa    1080
ccacaggtgt acaccctgcc cccatcccgg gaggagatga ccaagaacca ggtcagcctg    1140
acctgcctgg tcaaaggctt ctaccccagc gacatcgccg tggagtggga gagcaatggg    1200
cagccggaga caactacaa gaccacacct cccatgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga gagcctctc cctgtctccg    1380 ggtaaatga                                                           1389
```

<210> SEQ ID NO 22
<211> LENGTH: 1392
<212> TYPE: DNA
<213> ORGANISM: Artificial Sequence
<220> FEATURE:
<223> OTHER INFORMATION: Complete nucleotide sequence of the heavy chain of h21B12

<400> SEQUENCE: 22

```
atggactgga cctggcggat cctgtttctg gtggccgctg ctaccggcac acacgcccag    60
gtgcagctgg tgcagtccgg ctccgagctg aagaaacctg gcgcctccgt gaaggtgtcc    120
tgcaaggcct ccggctacac cttcaccaac tacggcatgc actgggtgcg ccaggcacct    180
ggacagggac tggaatggat gggctggatc aacacctaca ccggcgagcc tacctacgcc    240
gacgacttca agggcagatt cgtgttctcc ctggacacct ccgtgtccac cgcctacctg    300
cagatctcct ccctgaaggc cgaggacacc gccgtgtact actgcgccag ggacggcttc    360
ctgtacttct cgactactg gggccagggc accctggtga ccgtgtcctc tgcctccacc    420
aagggccctt ccgtgttccc tctggcccct gctcccggt ccacctctga gtctaccgcc    480
gctctgggct gcctggtgaa ggactacttc cctgagcctg tgacagtgtc ctggaactct    540
ggcgccctga cctctggcgt gcacaccttc cctgccgtgc tgcagtcctc cggcctgtac    600
tccctgtcct ccgtggtgac agtgccttcc tccaacttcg gcacccagac ctacacctgc    660
aacgtggacc acaagccttc caacaccaag gtggacaaga ccgtggagcg gaagtgctgc    720
gtggagtgcc ctccttgtcc tgctcctcct gtggctggcc ctagcgtgtt cctgttccct    780
cctaagccta aggacaccct gatgatctcc cggacccctg aagtgacctg cgtggtggtg    840
gacgtgtccc acgaggaccc tgaggtgcag ttcaattggt acgtggacgg cgtggaggtg    900
cacaacgcca agaccaagcc tcgggaggaa cagttcaact ccaccttccg ggtggtgtcc    960
gtgctgaccg tggtgcacca ggactggctg aacggcaaag aatacaagtg caaggtgtcc    1020
aacaagggcc tgcctgcccc tatcgaaaag accatctcta gaccaaggg ccagcctcgc    1080 gagcctcagg tgtacaccct gcctccctcc cgcgaggaaa tgaccaagaa ccaggtgtcc    1140
ctgacctgtc tggtgaaggg cttctaccct tccgatatcg ccgtggagtg ggagtctaac    1200
ggccagcctg agaacaacta caagaccacc cctcctatgc tggactccga cggctccttc    1260
ttcctgtaca gcaagctgac agtggacaag tcccggtggc agcagggcaa cgtgttctcc    1320
tgctccgtga tgcacgaggc cctgcacaac cactacaccc agaagtccct gtccctgtct    1380
cctggcaagt ga                                                       1392
```

<210> SEQ ID NO 23
<211> LENGTH: 720
<212> TYPE: DNA
<213> ORGANISM: Artificial Sequence
<220> FEATURE:
<223> OTHER INFORMATION: Complete nucleotide sequence of the light chain of h16B5

<400> SEQUENCE: 23

```
atggtgctgc agacccaggt gttcatctcc ctgctgctgt ggatctccgg cgcctacggc      60
gacatcgtga tgacccagtc ccccgactcc ctggccgtgt ccctgggcga gagagccacc     120
atcaactgca gtcctccca gtccctgctg aactcccgga cccggaagaa ctacctggcc     180
tggtatcagc agaagcctgg ccagcctcct aagctgctga tctactgggc ctccacccgg     240
gagtccggcg tgcctgaccg gttctccggc tccggcagcg gcaccgactt caccctgacc     300
atcagctccc tgcaggccga ggacgtggcc gtgtactact gcaagcagtc ctacaacctg     360
tggacctccg ccagggcac caagctggag atcaagcgga ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720
```

<210> SEQ ID NO 24
<211> LENGTH: 723
<212> TYPE: DNA
<213> ORGANISM: Artificial Sequence
<220> FEATURE:
<223> OTHER INFORMATION: Complete nucleotide sequence of the light chain of h21B12

<400> SEQUENCE: 24

```
atggtgctgc agacccaggt gttcatctcc ctgctgctgt ggatctctgg cgcctacggc      60
gacatcgtga tgacccagtc ccccgactct ctggctgtgt ccctgggcga gcggccacc     120
atcaactgca gtcctccca gtccctgctg tactcctcca accagaagaa ctacctggcc     180
tggtatcagc agaagcctgg ccagcctcct aagctgctga tctactgggc ctccacccgg     240
gaatctggcg tgcctgaccg gttctccggc tctggctccg gcaccgactt caccctgacc     300
atcagctccc tgcaggccga ggacgtggcc gtgtactact gccagcagta ctacatctac     360
cctcggacct tcggcagggg caccaagctg gaaatcaagc ggaccgtggc cgctccttcc     420
gtgttcatct tccccccttc cgacgagcag ctgaagtccg gcaccgcctc tgtggtgtgc     480
ctgctgaaca acttctaccc ccgggaggcc aaggtgcagt ggaaggtgga caacgccctg     540
cagtccggca actcccagga atccgtcacc gagcaggact ccaaggactc tacctactcc     600
ctgtcctcca ccctgaccct gtccaaggcc gactacgaga gcacaaggt gtacgcctgc     660
gaagtgaccc accagggcct gtcctctccc gtgaccaagt ccttcaaccg gggcgagtgc     720
tga                                                                    723
```

<210> SEQ ID NO 25
<211> LENGTH: 112
<212> TYPE: PRT
<213> ORGANISM: Artificial Sequence
<220> FEATURE:
<223> OTHER INFORMATION: murine 16B5 VL

<400> SEQUENCE: 25

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Cys Lys Gln
                85                  90                  95

Ser Tyr Asn Leu Trp Thr Phe Gly Gly Gly Thr Lys Leu Glu Phe Lys
            100                 105                 110

<210> SEQ ID NO 26
<211> LENGTH: 112
<212> TYPE: PRT
<213> ORGANISM: Artificial Sequence
<220> FEATURE:
<223> OTHER INFORMATION: humanized 16B5 VL consensus 1
<220> FEATURE:
<221> NAME/KEY: MISC_FEATURE
<222> LOCATION: (5)..(5)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (9)..(9)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (15)..(15)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (18)..(18)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (19)..(19)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (21)..(21)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (22)..(22)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (49)..(49)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (69)..(69)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (84)..(84)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (89)..(89)

<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (105)..(105)
<223> OTHER INFORMATION: Xaa is an amino acid substitution in comparison
      with a corresponding amino acid in SEQ ID NO.:25
<220> FEATURE:
<221> NAME/KEY: MISC_FEATURE
<222> LOCATION: (111)..(111)
<223> OTHER INFORMATION: Xaa is an amino acid substitution in comparison
      with a corresponding amino acid in SEQ ID NO.:25

<400> SEQUENCE: 26

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Val Tyr Tyr Cys Lys Gln
                85                  90                  95

Ser Tyr Asn Leu Trp Thr Phe Gly Xaa Gly Thr Lys Leu Glu Xaa Lys
                100                 105                 110

<210> SEQ ID NO 27
<211> LENGTH: 112
<212> TYPE: PRT
<213> ORGANISM: Artificial Sequence
<220> FEATURE:
<223> OTHER INFORMATION: humanized 16B5 VL consensus 2
<220> FEATURE:
<221> NAME/KEY: MISC_FEATURE
<222> LOCATION: (5)..(5)
<223> OTHER INFORMATION: Xaa is a neutral hydrophilic amino acid
<220> FEATURE:
<221> NAME/KEY: MISC_FEATURE
<222> LOCATION: (9)..(9)
<223> OTHER INFORMATION: Xaa is D or S
<220> FEATURE:
<221> NAME/KEY: MISC_FEATURE
<222> LOCATION: (15)..(15)
<223> OTHER INFORMATION: Xaa is an hydrophobic amino acid
<220> FEATURE:
<221> NAME/KEY: MISC_FEATURE
<222> LOCATION: (18)..(18)
<223> OTHER INFORMATION: Xaa is a basic amino acid
<220> FEATURE:
<221> NAME/KEY: MISC_FEATURE
<222> LOCATION: (19)..(19)
<223> OTHER INFORMATION: Xaa is an hydrophobic amino acid
<220> FEATURE:
<221> NAME/KEY: MISC_FEATURE
<222> LOCATION: (21)..(21)
<223> OTHER INFORMATION: Xaa is an hydrophobic amino acid
<220> FEATURE:
<221> NAME/KEY: MISC_FEATURE
<222> LOCATION: (22)..(22)
<223> OTHER INFORMATION: Xaa is N or S
<220> FEATURE:
<221> NAME/KEY: MISC_FEATURE
<222> LOCATION: (49)..(49)
<223> OTHER INFORMATION: Xaa is P or S
<220> FEATURE:
<221> NAME/KEY: MISC_FEATURE
<222> LOCATION: (69)..(69)
<223> OTHER INFORMATION: Xaa is a neutral hydrophilic amino acid

```
<220> FEATURE:
<221> NAME/KEY: MISC_FEATURE
<222> LOCATION: (84)..(84)
<223> OTHER INFORMATION: Xaa is an hydrophobic amino acid
<220> FEATURE:
<221> NAME/KEY: MISC_FEATURE
<222> LOCATION: (89)..(89)
<223> OTHER INFORMATION: Xaa is an hydrophobic amino acid
<220> FEATURE:
<221> NAME/KEY: MISC_FEATURE
<222> LOCATION: (105)..(105)
<223> OTHER INFORMATION: Xaa is Q or G
<220> FEATURE:
<221> NAME/KEY: MISC_FEATURE
<222> LOCATION: (111)..(111)
<223> OTHER INFORMATION: Xaa is I or F

<400> SEQUENCE: 27

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Val Tyr Tyr Cys Lys Gln
                85                  90                  95

Ser Tyr Asn Leu Trp Thr Phe Gly Xaa Gly Thr Lys Leu Glu Xaa Lys
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: humanized 16B5 VL consensus 3
<220> FEATURE:
<221> NAME/KEY: MISC_FEATURE
<222> LOCATION: (5)..(5)
<223> OTHER INFORMATION: Xaa is T or S
<220> FEATURE:
<221> NAME/KEY: MISC_FEATURE
<222> LOCATION: (9)..(9)
<223> OTHER INFORMATION: Xaa is D or S
<220> FEATURE:
<221> NAME/KEY: MISC_FEATURE
<222> LOCATION: (15)..(15)
<223> OTHER INFORMATION: Xaa is L or A
<220> FEATURE:
<221> NAME/KEY: MISC_FEATURE
<222> LOCATION: (18)..(18)
<223> OTHER INFORMATION: Xaa is R or K
<220> FEATURE:
<221> NAME/KEY: MISC_FEATURE
<222> LOCATION: (19)..(19)
<223> OTHER INFORMATION: Xaa is A or V
<220> FEATURE:
<221> NAME/KEY: MISC_FEATURE
<222> LOCATION: (21)..(21)
<223> OTHER INFORMATION: Xaa is I or M
<220> FEATURE:
<221> NAME/KEY: MISC_FEATURE
<222> LOCATION: (22)..(22)
<223> OTHER INFORMATION: Xaa is N or S
<220> FEATURE:
<221> NAME/KEY: MISC_FEATURE
<222> LOCATION: (49)..(49)
<223> OTHER INFORMATION: Xaa is P or S
```

```
<220> FEATURE:
<221> NAME/KEY: MISC_FEATURE
<222> LOCATION: (69)..(69)
<223> OTHER INFORMATION: Xaa is S or T
<220> FEATURE:
<221> NAME/KEY: MISC_FEATURE
<222> LOCATION: (84)..(84)
<223> OTHER INFORMATION: Xaa is L or V
<220> FEATURE:
<221> NAME/KEY: MISC_FEATURE
<222> LOCATION: (89)..(89)
<223> OTHER INFORMATION: Xaa is V or L
<220> FEATURE:
<221> NAME/KEY: MISC_FEATURE
<222> LOCATION: (105)..(105)
<223> OTHER INFORMATION: Xaa is Q or G
<220> FEATURE:
<221> NAME/KEY: MISC_FEATURE
<222> LOCATION: (111)..(111)
<223> OTHER INFORMATION: Xaa is I or F

<400> SEQUENCE: 28

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Val Tyr Tyr Cys Lys Gln
                85                  90                  95

Ser Tyr Asn Leu Trp Thr Phe Gly Xaa Gly Thr Lys Leu Glu Xaa Lys
                100                 105                 110

<210> SEQ ID NO 29
<211> LENGTH: 117
<212> TYPE: PRT
<213> ORGANISM: Artificial Sequence
<220> FEATURE:
<223> OTHER INFORMATION: murine 16B5 VH

<400> SEQUENCE: 29

Glu Val Gln Leu Gln Gln Ser Gly Ala Glu Leu Val Lys Pro Gly Ala
1               5                   10                  15

Ser Val Arg Leu Ser Cys Thr Thr Ser Gly Phe Asn Ile Lys Asp Ile
            20                  25                  30

Tyr Met His Trp Val Lys Gln Arg Pro Glu Gln Gly Leu Glu Trp Ile
        35                  40                  45

Gly Arg Ile Asp Pro Ala Tyr Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Tyr Asp Thr Ala Met Asp Tyr Trp Gly Gln Gly Thr Ser
                100                 105                 110

Val Thr Val Ser Ser
            115
```

```
<210> SEQ ID NO 30
<211> LENGTH: 117
<212> TYPE: PRT
<213> ORGANISM: Artificial Sequence
<220> FEATURE:
<223> OTHER INFORMATION: humanized 16B5 VH consensus 1
<220> FEATURE:
<221> NAME/KEY: MISC_FEATURE
<222> LOCATION: (1)..(1)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (5)..(5)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (11)..(11)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (12)..(12)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (17)..(17)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (19)..(19)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (20)..(20)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (23)..(23)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (24)..(24)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (38)..(38)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (40)..(40)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (42)..(42)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (43)..(43)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (48)..(48)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (67)..(67)
```

<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (68)..(68)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (76)..(76)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (77)..(77)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (81)..(81)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (82)..(82)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (87)..(87)
<223> OTHER INFORMATION: Xaa is an amino acid substitution in comparison
      with a corresponding amino acid in SEQ ID NO.:29
<220> FEATURE:
<221> NAME/KEY: MISC_FEATURE
<222> LOCATION: (112)..(112)
<223> OTHER INFORMATION: Xaa is an amino acid substitution in comparison
      with a corresponding amino acid in SEQ ID NO.:29

<400> SEQUENCE: 30

Xaa Val Gln Leu Xaa Gln Ser Gly Ala Glu Xaa Xaa Lys Pro Gly Ala
1               5                   10                  15

Xaa Val Xaa Xaa Ser Cys Xaa Xaa Ser Gly Phe Asn Ile Lys Asp Ile
            20                  25                  30

Tyr Met His Trp Val Xaa Gln Xaa Pro Xaa Xaa Gly Leu Glu Trp Xaa
                35                  40                  45

Gly Arg Ile Asp Pro Ala Tyr Gly Asn Thr Lys Tyr Asp Pro Lys Phe
    50                  55                  60

Gln Gly Xaa Xaa Thr Ile Thr Ala Asp Thr Ser Xaa Xaa Thr Ala Tyr
65                  70                  75                  80

Xaa Xaa Leu Ser Ser Leu Xaa Ser Glu Asp Thr Ala Val Tyr Tyr Cys
                85                  90                  95

Ala Arg Arg Tyr Asp Thr Ala Met Asp Tyr Trp Gly Gln Gly Thr Xaa
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: humanized 16B5 VH consensus 2
<220> FEATURE:
<221> NAME/KEY: MISC_FEATURE
<222> LOCATION: (1)..(1)
<223> OTHER INFORMATION: Xaa is Q or E
<220> FEATURE:
<221> NAME/KEY: MISC_FEATURE
<222> LOCATION: (5)..(5)
<223> OTHER INFORMATION: Xaa is V or Q

```
<220> FEATURE:
<221> NAME/KEY: MISC_FEATURE
<222> LOCATION: (11)..(11)
<223> OTHER INFORMATION: Xaa is an hydrophobic amino acid
<220> FEATURE:
<221> NAME/KEY: MISC_FEATURE
<222> LOCATION: (12)..(12)
<223> OTHER INFORMATION: Xaa is K or V
<220> FEATURE:
<221> NAME/KEY: MISC_FEATURE
<222> LOCATION: (17)..(17)
<223> OTHER INFORMATION: Xaa is a neutral hydrohilic amino acid
<220> FEATURE:
<221> NAME/KEY: MISC_FEATURE
<222> LOCATION: (19)..(19)
<223> OTHER INFORMATION: Xaa is a basic amino acid
<220> FEATURE:
<221> NAME/KEY: MISC_FEATURE
<222> LOCATION: (20)..(20)
<223> OTHER INFORMATION: Xaa is an hydrophobic amino acid
<220> FEATURE:
<221> NAME/KEY: MISC_FEATURE
<222> LOCATION: (23)..(23)
<223> OTHER INFORMATION: Xaa is K or T
<220> FEATURE:
<221> NAME/KEY: MISC_FEATURE
<222> LOCATION: (24)..(24)
<223> OTHER INFORMATION: Xaa is V or T
<220> FEATURE:
<221> NAME/KEY: MISC_FEATURE
<222> LOCATION: (38)..(38)
<223> OTHER INFORMATION: Xaa is basic amino acid
<220> FEATURE:
<221> NAME/KEY: MISC_FEATURE
<222> LOCATION: (40)..(40)
<223> OTHER INFORMATION: Xaa is A or R
<220> FEATURE:
<221> NAME/KEY: MISC_FEATURE
<222> LOCATION: (42)..(42)
<223> OTHER INFORMATION: Xaa is G or E
<220> FEATURE:
<221> NAME/KEY: MISC_FEATURE
<222> LOCATION: (43)..(43)
<223> OTHER INFORMATION: Xaa is a basic amino acid
<220> FEATURE:
<221> NAME/KEY: MISC_FEATURE
<222> LOCATION: (48)..(48)
<223> OTHER INFORMATION: Xaa is an hydrophobic amino acid
<220> FEATURE:
<221> NAME/KEY: MISC_FEATURE
<222> LOCATION: (67)..(67)
<223> OTHER INFORMATION: Xaa is a basic amino acid
<220> FEATURE:
<221> NAME/KEY: MISC_FEATURE
<222> LOCATION: (68)..(68)
<223> OTHER INFORMATION: Xaa is an hydrophobic amino acid
<220> FEATURE:
<221> NAME/KEY: MISC_FEATURE
<222> LOCATION: (76)..(76)
<223> OTHER INFORMATION: Xaa is neutral hydrophilic amino acid
<220> FEATURE:
<221> NAME/KEY: MISC_FEATURE
<222> LOCATION: (77)..(77)
<223> OTHER INFORMATION: Xaa is D or N
<220> FEATURE:
<221> NAME/KEY: MISC_FEATURE
<222> LOCATION: (81)..(81)
<223> OTHER INFORMATION: Xaa is an hydrophobic amino acid
<220> FEATURE:
<221> NAME/KEY: MISC_FEATURE
<222> LOCATION: (82)..(82)
<223> OTHER INFORMATION: Xaa is E or Q
<220> FEATURE:
<221> NAME/KEY: MISC_FEATURE
<222> LOCATION: (87)..(87)
<223> OTHER INFORMATION: Xaa is R or T
<220> FEATURE:
<221> NAME/KEY: MISC_FEATURE
<222> LOCATION: (112)..(112)
```

<223> OTHER INFORMATION: Xaa is L or S

<400> SEQUENCE: 31

Xaa Val Gln Leu Xaa Gln Ser Gly Ala Glu Xaa Xaa Lys Pro Gly Ala
1               5                   10                  15

Xaa Val Xaa Xaa Ser Cys Xaa Xaa Ser Gly Phe Asn Ile Lys Asp Ile
            20                  25                  30

Tyr Met His Trp Val Xaa Gln Xaa Pro Xaa Xaa Gly Leu Glu Trp Xaa
        35                  40                  45

Gly Arg Ile Asp Pro Ala Tyr Gly Asn Thr Lys Tyr Asp Pro Lys Phe
    50                  55                  60

Gln Gly Xaa Xaa Thr Ile Thr Ala Asp Thr Ser Xaa Xaa Thr Ala Tyr
65                  70                  75                  80

Xaa Xaa Leu Ser Ser Leu Xaa Ser Glu Asp Thr Ala Val Tyr Tyr Cys
            85                  90                  95

Ala Arg Arg Tyr Asp Thr Ala Met Asp Tyr Trp Gly Gln Gly Thr Xaa
            100                 105                 110

Val Thr Val Ser Ser
        115

```
<210> SEQ ID NO 32
<211> LENGTH: 117
<212> TYPE: PRT
<213> ORGANISM: Artificial Sequence
<220> FEATURE:
<223> OTHER INFORMATION: humanized 16B5 VH consensus 3
<220> FEATURE:
<221> NAME/KEY: MISC_FEATURE
<222> LOCATION: (1)..(1)
<223> OTHER INFORMATION: Xaa is Q or E
<220> FEATURE:
<221> NAME/KEY: MISC_FEATURE
<222> LOCATION: (5)..(5)
<223> OTHER INFORMATION: Xaa is V or Q
<220> FEATURE:
<221> NAME/KEY: MISC_FEATURE
<222> LOCATION: (11)..(11)
<223> OTHER INFORMATION: Xaa is V or L
<220> FEATURE:
<221> NAME/KEY: MISC_FEATURE
<222> LOCATION: (12)..(12)
<223> OTHER INFORMATION: Xaa is K or V
<220> FEATURE:
<221> NAME/KEY: MISC_FEATURE
<222> LOCATION: (17)..(17)
<223> OTHER INFORMATION: Xaa is T or S
<220> FEATURE:
<221> NAME/KEY: MISC_FEATURE
<222> LOCATION: (19)..(19)
<223> OTHER INFORMATION: Xaa is K or R
<220> FEATURE:
<221> NAME/KEY: MISC_FEATURE
<222> LOCATION: (20)..(20)
<223> OTHER INFORMATION: Xaa is I or L
<220> FEATURE:
<221> NAME/KEY: MISC_FEATURE
<222> LOCATION: (23)..(23)
<223> OTHER INFORMATION: Xaa is K or T
<220> FEATURE:
<221> NAME/KEY: MISC_FEATURE
<222> LOCATION: (24)..(24)
<223> OTHER INFORMATION: Xaa is V or T
<220> FEATURE:
<221> NAME/KEY: MISC_FEATURE
<222> LOCATION: (38)..(38)
<223> OTHER INFORMATION: Xaa is Q or K
<220> FEATURE:
<221> NAME/KEY: MISC_FEATURE
<222> LOCATION: (40)..(40)
<223> OTHER INFORMATION: Xaa is A or R
```

```
<220> FEATURE:
<221> NAME/KEY: MISC_FEATURE
<222> LOCATION: (42)..(42)
<223> OTHER INFORMATION: Xaa is G or E
<220> FEATURE:
<221> NAME/KEY: MISC_FEATURE
<222> LOCATION: (43)..(43)
<223> OTHER INFORMATION: Xaa is K or Q
<220> FEATURE:
<221> NAME/KEY: MISC_FEATURE
<222> LOCATION: (48)..(48)
<223> OTHER INFORMATION: Xaa is M or I
<220> FEATURE:
<221> NAME/KEY: MISC_FEATURE
<222> LOCATION: (67)..(67)
<223> OTHER INFORMATION: Xaa is R or K
<220> FEATURE:
<221> NAME/KEY: MISC_FEATURE
<222> LOCATION: (68)..(68)
<223> OTHER INFORMATION: Xaa is V or A
<220> FEATURE:
<221> NAME/KEY: MISC_FEATURE
<222> LOCATION: (76)..(76)
<223> OTHER INFORMATION: Xaa is T or S
<220> FEATURE:
<221> NAME/KEY: MISC_FEATURE
<222> LOCATION: (77)..(77)
<223> OTHER INFORMATION: Xaa is D or N
<220> FEATURE:
<221> NAME/KEY: MISC_FEATURE
<222> LOCATION: (81)..(81)
<223> OTHER INFORMATION: Xaa is M or L
<220> FEATURE:
<221> NAME/KEY: MISC_FEATURE
<222> LOCATION: (82)..(82)
<223> OTHER INFORMATION: Xaa is E or Q
<220> FEATURE:
<221> NAME/KEY: MISC_FEATURE
<222> LOCATION: (87)..(87)
<223> OTHER INFORMATION: Xaa is R or T
<220> FEATURE:
<221> NAME/KEY: MISC_FEATURE
<222> LOCATION: (112)..(112)
<223> OTHER INFORMATION: Xaa is L or S

<400> SEQUENCE: 32

Xaa Val Gln Leu Xaa Gln Ser Gly Ala Glu Xaa Xaa Lys Pro Gly Ala
1               5                   10                  15

Xaa Val Xaa Xaa Ser Cys Xaa Xaa Ser Gly Phe Asn Ile Lys Asp Ile
            20                  25                  30

Tyr Met His Trp Val Xaa Gln Xaa Pro Xaa Xaa Gly Leu Glu Trp Xaa
            35                  40                  45

Gly Arg Ile Asp Pro Ala Tyr Gly Asn Thr Lys Tyr Asp Pro Lys Phe
50                  55                  60

Gln Gly Xaa Xaa Thr Ile Thr Ala Asp Thr Ser Xaa Xaa Thr Ala Tyr
65                  70                  75                  80

Xaa Xaa Leu Ser Ser Leu Xaa Ser Glu Asp Thr Ala Val Tyr Tyr Cys
                85                  90                  95

Ala Arg Arg Tyr Asp Thr Ala Met Asp Tyr Trp Gly Gln Gly Thr Xaa
            100                 105                 110

Val Thr Val Ser Ser
        115

<210> SEQ ID NO 33
<211> LENGTH: 113
<212> TYPE: PRT
<213> ORGANISM: Artificial Sequence
<220> FEATURE:
<223> OTHER INFORMATION: murine 21B12 VL
```

<400> SEQUENCE: 33

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Arg Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ile Tyr Pro Arg Thr Phe Gly Gly Gly Thr Lys Leu Glu Ile
            100                 105                 110

Lys

<210> SEQ ID NO 34
<211> LENGTH: 113
<212> TYPE: PRT
<213> ORGANISM: Artificial Sequence
<220> FEATURE:
<223> OTHER INFORMATION: humanized 21B12 VL consensus 1
<220> FEATURE:
<221> NAME/KEY: MISC_FEATURE
<222> LOCATION: (5)..(5)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (9)..(9)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (15)..(15)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (18)..(18)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (19)..(19)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (21)..(21)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (22)..(22)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (45)..(45)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (49)..(49)
<223> OTHER INFORMATION: Xaa is an amino acid substitution in comparison
      with a corresponding amino acid in SEQ ID NO.:33
<220> FEATURE:
<221> NAME/KEY: MISC_FEATURE
<222> LOCATION: (69)..(69)
<223> OTHER INFORMATION: Xaa is an amino acid substitution in comparison
     with a corresponding amino acid in SEQ ID NO.:33
<220> FEATURE:
<221> NAME/KEY: MISC_FEATURE
<222> LOCATION: (84)..(84)
<223> OTHER INFORMATION: Xaa is an amino acid substitution in comparison
     with a corresponding amino acid in SEQ ID NO.:33
<220> FEATURE:
<221> NAME/KEY: MISC_FEATURE
<222> LOCATION: (85)..(85)
<223> OTHER INFORMATION: Xaa is an amino acid substitution in comparison
     with a corresponding amino acid in SEQ ID NO.:33
<220> FEATURE:
<221> NAME/KEY: MISC_FEATURE
<222> LOCATION: (89)..(89)
<223> OTHER INFORMATION: Xaa is an amino acid substitution in comparison
     with a corresponding amino acid in SEQ ID NO.:33
<220> FEATURE:
<221> NAME/KEY: MISC_FEATURE
<222> LOCATION: (106)..(106)
<223> OTHER INFORMATION: Xaa is an amino acid substitution in comparison
     with a corresponding amino acid in SEQ ID NO.:33

<400> SEQUENCE: 34

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Tyr Ser
                20                  25                  30

Ser Asn Gln Lys Asn Tyr Leu Ala Trp Tyr Gln Gln Xaa Pro Gly Gln
            35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Gln Gln
                85                  90                  95

Tyr Tyr Ile Tyr Pro Arg Thr Phe Gly Xaa Gly Thr Lys Leu Glu Ile
            100                 105                 110

Lys

<210> SEQ ID NO 35
<211> LENGTH: 113
<212> TYPE: PRT
<213> ORGANISM: Artificial Sequence
<220> FEATURE:
<223> OTHER INFORMATION: humanized 21B12 VL consensus 2
<220> FEATURE:
<221> NAME/KEY: MISC_FEATURE
<222> LOCATION: (5)..(5)
<223> OTHER INFORMATION: Xaa is a neutral hyrophilic amino acid
<220> FEATURE:
<221> NAME/KEY: MISC_FEATURE
<222> LOCATION: (9)..(9)
<223> OTHER INFORMATION: Xaa is D or S
<220> FEATURE:
<221> NAME/KEY: MISC_FEATURE
<222> LOCATION: (15)..(15)
<223> OTHER INFORMATION: Xaa is an hydrophobic amino acid
<220> FEATURE:
<221> NAME/KEY: MISC_FEATURE
<222> LOCATION: (18)..(18)
<223> OTHER INFORMATION: Xaa is a basic amino acid
<220> FEATURE:
<221> NAME/KEY: MISC_FEATURE
<222> LOCATION: (19)..(19)
<223> OTHER INFORMATION: Xaa is an hydrophobic amino acid
<220> FEATURE:
<221> NAME/KEY: MISC_FEATURE
<222> LOCATION: (21)..(21)

<223> OTHER INFORMATION: Xaa is an hydrophobic amino acid
<220> FEATURE:
<221> NAME/KEY: MISC_FEATURE
<222> LOCATION: (22)..(22)
<223> OTHER INFORMATION: Xaa is N or S
<220> FEATURE:
<221> NAME/KEY: MISC_FEATURE
<222> LOCATION: (45)..(45)
<223> OTHER INFORMATION: Xaa is a basic amino acid
<220> FEATURE:
<221> NAME/KEY: MISC_FEATURE
<222> LOCATION: (49)..(49)
<223> OTHER INFORMATION: Xaa is P or S
<220> FEATURE:
<221> NAME/KEY: MISC_FEATURE
<222> LOCATION: (69)..(69)
<223> OTHER INFORMATION: Xaa is a neutral hydrophilic amino acid
<220> FEATURE:
<221> NAME/KEY: MISC_FEATURE
<222> LOCATION: (84)..(84)
<223> OTHER INFORMATION: Xaa is an hydrophobic amino acid
<220> FEATURE:
<221> NAME/KEY: MISC_FEATURE
<222> LOCATION: (85)..(85)
<223> OTHER INFORMATION: Xaa is a basic amino acid
<220> FEATURE:
<221> NAME/KEY: MISC_FEATURE
<222> LOCATION: (89)..(89)
<223> OTHER INFORMATION: Xaa is an hydrophobic amino acid
<220> FEATURE:
<221> NAME/KEY: MISC_FEATURE
<222> LOCATION: (106)..(106)
<223> OTHER INFORMATION: Xaa is Q or G

<400> SEQUENCE: 35

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Tyr Ser
                20                  25                  30

Ser Asn Gln Lys Asn Tyr Leu Ala Trp Tyr Gln Gln Xaa Pro Gly Gln
            35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Gln Gln
                85                  90                  95

Tyr Tyr Ile Tyr Pro Arg Thr Phe Gly Xaa Gly Thr Lys Leu Glu Ile
            100                 105                 110

Lys

<210> SEQ ID NO 36
<211> LENGTH: 113
<212> TYPE: PRT
<213> ORGANISM: Artificial Sequence
<220> FEATURE:
<223> OTHER INFORMATION: humanized 21B12 VL consensus 3
<220> FEATURE:
<221> NAME/KEY: MISC_FEATURE
<222> LOCATION: (5)..(5)
<223> OTHER INFORMATION: Xaa is T or S
<220> FEATURE:
<221> NAME/KEY: MISC_FEATURE
<222> LOCATION: (9)..(9)
<223> OTHER INFORMATION: Xaa is D or S
<220> FEATURE:
<221> NAME/KEY: MISC_FEATURE
<222> LOCATION: (15)..(15)
<223> OTHER INFORMATION: Xaa is L or V
<220> FEATURE:

```
<221> NAME/KEY: MISC_FEATURE
<222> LOCATION: (18)..(18)
<223> OTHER INFORMATION: Xaa is R or K
<220> FEATURE:
<221> NAME/KEY: MISC_FEATURE
<222> LOCATION: (19)..(19)
<223> OTHER INFORMATION: Xaa is A or V
<220> FEATURE:
<221> NAME/KEY: MISC_FEATURE
<222> LOCATION: (21)..(21)
<223> OTHER INFORMATION: Xaa is I or M
<220> FEATURE:
<221> NAME/KEY: MISC_FEATURE
<222> LOCATION: (22)..(22)
<223> OTHER INFORMATION: Xaa is N or S
<220> FEATURE:
<221> NAME/KEY: MISC_FEATURE
<222> LOCATION: (45)..(45)
<223> OTHER INFORMATION: Xaa is K or R
<220> FEATURE:
<221> NAME/KEY: MISC_FEATURE
<222> LOCATION: (49)..(49)
<223> OTHER INFORMATION: Xaa is P or S
<220> FEATURE:
<221> NAME/KEY: MISC_FEATURE
<222> LOCATION: (69)..(69)
<223> OTHER INFORMATION: Xaa is S or T
<220> FEATURE:
<221> NAME/KEY: MISC_FEATURE
<222> LOCATION: (84)..(84)
<223> OTHER INFORMATION: Xaa is L or V
<220> FEATURE:
<221> NAME/KEY: MISC_FEATURE
<222> LOCATION: (85)..(85)
<223> OTHER INFORMATION: Xaa is Q or K
<220> FEATURE:
<221> NAME/KEY: MISC_FEATURE
<222> LOCATION: (89)..(89)
<223> OTHER INFORMATION: Xaa is V or L
<220> FEATURE:
<221> NAME/KEY: MISC_FEATURE
<222> LOCATION: (106)..(106)
<223> OTHER INFORMATION: Xaa is Q or G

<400> SEQUENCE: 36

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Tyr Ser
                20                  25                  30

Ser Asn Gln Lys Asn Tyr Leu Ala Trp Tyr Gln Gln Xaa Pro Gly Gln
            35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Gln Gln
                85                  90                  95

Tyr Tyr Ile Tyr Pro Arg Thr Phe Gly Xaa Gly Thr Lys Leu Glu Ile
            100                 105                 110

Lys

<210> SEQ ID NO 37
<211> LENGTH: 118
<212> TYPE: PRT
<213> ORGANISM: Artificial Sequence
<220> FEATURE:
<223> OTHER INFORMATION: murine 21B12 VH

<400> SEQUENCE: 37
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met His Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
            85                  90                  95

Ala Arg Asp Gly Phe Leu Tyr Phe Phe Asp Tyr Trp Gly Gln Gly Thr
                100                 105                 110

Thr Leu Thr Val Ser Ser
            115

<210> SEQ ID NO 38
<211> LENGTH: 118
<212> TYPE: PRT
<213> ORGANISM: Artificial Sequence
<220> FEATURE:
<223> OTHER INFORMATION: humanized 21B12 VH consensus 1
<220> FEATURE:
<221> NAME/KEY: MISC_FEATURE
<222> LOCATION: (2)..(2)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (9)..(9)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (16)..(16)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (17)..(17)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (20)..(20)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (38)..(38)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (43)..(43)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (46)..(46)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (69)..(69)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (73)..(73)

<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (76)..(76)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (84)..(84)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (85)..(85)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (88)..(88)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (93)..(93)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (95)..(95)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (113)..(113)
<223> OTHER INFORMATION: Xaa is an amino acid substitution in comparison
      with a corresponding amino acid in SEQ ID NO.:37
<220> FEATURE:
<221> NAME/KEY: MISC_FEATURE
<222> LOCATION: (114)..(114)
<223> OTHER INFORMATION: Xaa is an amino acid substitution in comparison
      with a corresponding amino acid in SEQ ID NO.:37

<400> SEQUENCE: 38

Gln Xaa Gln Leu Val Gln Ser Gly Xaa Glu Leu Lys Lys Pro Gly Xaa
1               5                   10                  15

Xaa Val Lys Xaa Ser Cys Lys Ala Ser Gly Tyr Thr Phe Thr Asn Tyr
            20                  25                  30

Gly Met His Trp Val Xaa Gln Ala Pro Gly Xaa Gly Leu Xaa Trp Met
        35                  40                  45

Gly Trp Ile Asn Thr Tyr Thr Gly Glu Pro Thr Tyr Ala Asp Asp Phe
    50                  55                  60

Lys Gly Arg Phe Xaa Phe Ser Leu Xaa Thr Ser Xaa Ser Thr Ala Tyr
65                  70                  75                  80

Leu Gln Ile Xaa Xaa Leu Lys Xaa Glu Asp Thr Ala Xaa Tyr Xaa Cys
                85                  90                  95

Ala Arg Asp Gly Phe Leu Tyr Phe Phe Asp Tyr Trp Gly Gln Gly Thr
            100                 105                 110

Xaa Xaa Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: humanized 21B12 VH consensus 2
<220> FEATURE:
<221> NAME/KEY: MISC_FEATURE
<222> LOCATION: (2)..(2)

```
<223> OTHER INFORMATION: Xaa is an hydrophobic amino acid
<220> FEATURE:
<221> NAME/KEY: MISC_FEATURE
<222> LOCATION: (9)..(9)
<223> OTHER INFORMATION: Xaa is S or P
<220> FEATURE:
<221> NAME/KEY: MISC_FEATURE
<222> LOCATION: (16)..(16)
<223> OTHER INFORMATION: Xaa is A or E
<220> FEATURE:
<221> NAME/KEY: MISC_FEATURE
<222> LOCATION: (17)..(17)
<223> OTHER INFORMATION: Xaa is a neutral hydrophilic amino acid
<220> FEATURE:
<221> NAME/KEY: MISC_FEATURE
<222> LOCATION: (20)..(20)
<223> OTHER INFORMATION: Xaa is an hydrophobic amino acid
<220> FEATURE:
<221> NAME/KEY: MISC_FEATURE
<222> LOCATION: (38)..(38)
<223> OTHER INFORMATION: Xaa is a basic amino acid
<220> FEATURE:
<221> NAME/KEY: MISC_FEATURE
<222> LOCATION: (43)..(43)
<223> OTHER INFORMATION: Xaa is a basic amino acid
<220> FEATURE:
<221> NAME/KEY: MISC_FEATURE
<222> LOCATION: (46)..(46)
<223> OTHER INFORMATION: Xaa is E or K
<220> FEATURE:
<221> NAME/KEY: MISC_FEATURE
<222> LOCATION: (69)..(69)
<223> OTHER INFORMATION: Xaa is an hydrophobic amino acid
<220> FEATURE:
<221> NAME/KEY: MISC_FEATURE
<222> LOCATION: (73)..(73)
<223> OTHER INFORMATION: Xaa is an acidic amino acid
<220> FEATURE:
<221> NAME/KEY: MISC_FEATURE
<222> LOCATION: (76)..(76)
<223> OTHER INFORMATION: Xaa is an hydrophobic amino acid
<220> FEATURE:
<221> NAME/KEY: MISC_FEATURE
<222> LOCATION: (84)..(84)
<223> OTHER INFORMATION: Xaa is S or N
<220> FEATURE:
<221> NAME/KEY: MISC_FEATURE
<222> LOCATION: (85)..(85)
<223> OTHER INFORMATION: Xaa is S or N
<220> FEATURE:
<221> NAME/KEY: MISC_FEATURE
<222> LOCATION: (88)..(88)
<223> OTHER INFORMATION: Xaa is A or N
<220> FEATURE:
<221> NAME/KEY: MISC_FEATURE
<222> LOCATION: (93)..(93)
<223> OTHER INFORMATION: Xaa is V or T
<220> FEATURE:
<221> NAME/KEY: MISC_FEATURE
<222> LOCATION: (95)..(95)
<223> OTHER INFORMATION: Xaa is an aromatic amino acid
<220> FEATURE:
<221> NAME/KEY: MISC_FEATURE
<222> LOCATION: (113)..(113)
<223> OTHER INFORMATION: Xaa is L or T
<220> FEATURE:
<221> NAME/KEY: MISC_FEATURE
<222> LOCATION: (114)..(114)
<223> OTHER INFORMATION: Xaa is an hydrophobic amino acid

<400> SEQUENCE: 39

Gln Xaa Gln Leu Val Gln Ser Gly Xaa Glu Leu Lys Lys Pro Gly Xaa
1               5                   10                  15

Xaa Val Lys Xaa Ser Cys Lys Ala Ser Gly Tyr Thr Phe Thr Asn Tyr
            20                  25                  30

Gly Met His Trp Val Xaa Gln Ala Pro Gly Xaa Gly Leu Xaa Trp Met
```

```
                35                  40                  45
Gly Trp Ile Asn Thr Tyr Thr Gly Glu Pro Tyr Ala Asp Asp Phe
            50                  55                  60

Lys Gly Arg Phe Xaa Phe Ser Leu Xaa Thr Ser Xaa Ser Thr Ala Tyr
 65              70                  75                  80

Leu Gln Ile Xaa Xaa Leu Lys Xaa Glu Asp Thr Ala Xaa Tyr Xaa Cys
                85                  90                  95

Ala Arg Asp Gly Phe Leu Tyr Phe Phe Asp Tyr Trp Gly Gln Gly Thr
            100                 105                 110

Xaa Xaa Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: humanized 21B12 VH consensus 3
<220> FEATURE:
<221> NAME/KEY: MISC_FEATURE
<222> LOCATION: (2)..(2)
<223> OTHER INFORMATION: Xaa is V or I
<220> FEATURE:
<221> NAME/KEY: MISC_FEATURE
<222> LOCATION: (9)..(9)
<223> OTHER INFORMATION: Xaa is S or P
<220> FEATURE:
<221> NAME/KEY: MISC_FEATURE
<222> LOCATION: (16)..(16)
<223> OTHER INFORMATION: Xaa is A or E
<220> FEATURE:
<221> NAME/KEY: MISC_FEATURE
<222> LOCATION: (17)..(17)
<223> OTHER INFORMATION: Xaa is S or T
<220> FEATURE:
<221> NAME/KEY: MISC_FEATURE
<222> LOCATION: (20)..(20)
<223> OTHER INFORMATION: Xaa is V or I
<220> FEATURE:
<221> NAME/KEY: MISC_FEATURE
<222> LOCATION: (38)..(38)
<223> OTHER INFORMATION: Xaa is R or K
<220> FEATURE:
<221> NAME/KEY: MISC_FEATURE
<222> LOCATION: (43)..(43)
<223> OTHER INFORMATION: Xaa is Q or K
<220> FEATURE:
<221> NAME/KEY: MISC_FEATURE
<222> LOCATION: (46)..(46)
<223> OTHER INFORMATION: Xaa is E or K
<220> FEATURE:
<221> NAME/KEY: MISC_FEATURE
<222> LOCATION: (69)..(69)
<223> OTHER INFORMATION: Xaa is V or A
<220> FEATURE:
<221> NAME/KEY: MISC_FEATURE
<222> LOCATION: (73)..(73)
<223> OTHER INFORMATION: Xaa is D or E
<220> FEATURE:
<221> NAME/KEY: MISC_FEATURE
<222> LOCATION: (76)..(76)
<223> OTHER INFORMATION: Xaa is V or A
<220> FEATURE:
<221> NAME/KEY: MISC_FEATURE
<222> LOCATION: (84)..(84)
<223> OTHER INFORMATION: Xaa is S or N
<220> FEATURE:
<221> NAME/KEY: MISC_FEATURE
<222> LOCATION: (85)..(85)
<223> OTHER INFORMATION: Xaa is S or N
<220> FEATURE:
<221> NAME/KEY: MISC_FEATURE
<222> LOCATION: (88)..(88)
```

```
<223> OTHER INFORMATION: Xaa is A or N
<220> FEATURE:
<221> NAME/KEY: MISC_FEATURE
<222> LOCATION: (93)..(93)
<223> OTHER INFORMATION: Xaa is V or T
<220> FEATURE:
<221> NAME/KEY: MISC_FEATURE
<222> LOCATION: (95)..(95)
<223> OTHER INFORMATION: Xaa is Y or F
<220> FEATURE:
<221> NAME/KEY: MISC_FEATURE
<222> LOCATION: (113)..(113)
<223> OTHER INFORMATION: Xaa is L or T
<220> FEATURE:
<221> NAME/KEY: MISC_FEATURE
<222> LOCATION: (114)..(114)
<223> OTHER INFORMATION: Xaa is V or L

<400> SEQUENCE: 40

Gln Xaa Gln Leu Val Gln Ser Gly Xaa Glu Leu Lys Lys Pro Gly Xaa
1               5                   10                  15

Xaa Val Lys Xaa Ser Cys Lys Ala Ser Gly Tyr Thr Phe Thr Asn Tyr
            20                  25                  30

Gly Met His Trp Val Xaa Gln Ala Pro Gly Xaa Gly Leu Xaa Trp Met
        35                  40                  45

Gly Trp Ile Asn Thr Tyr Thr Gly Glu Pro Thr Tyr Ala Asp Asp Phe
    50                  55                  60

Lys Gly Arg Phe Xaa Phe Ser Leu Xaa Thr Ser Xaa Ser Thr Ala Tyr
65                  70                  75                  80

Leu Gln Ile Xaa Xaa Leu Lys Xaa Glu Asp Thr Ala Xaa Tyr Xaa Cys
                85                  90                  95

Ala Arg Asp Gly Phe Leu Tyr Phe Phe Asp Tyr Trp Gly Gln Gly Thr
                100                 105                 110

Xaa Xaa Thr Val Ser Ser
        115

<210> SEQ ID NO 41
<211> LENGTH: 113
<212> TYPE: PRT
<213> ORGANISM: Artificial Sequence
<220> FEATURE:
<223> OTHER INFORMATION: human model of 16B5 VL

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
                100                 105                 110

Lys

<210> SEQ ID NO 42
```

```
<211> LENGTH: 117
<212> TYPE: PRT
<213> ORGANISM: Artificial Sequence
<220> FEATURE:
<223> OTHER INFORMATION: human model of 16B5 VH

<400> SEQUENCE: 42

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Pro Leu Phe Gly Arg Asp His Trp Gly Gln Gly Thr Leu
            100                 105                 110

Val Thr Val Ser Arg
        115

<210> SEQ ID NO 43
<211> LENGTH: 113
<212> TYPE: PRT
<213> ORGANISM: Artificial Sequence
<220> FEATURE:
<223> OTHER INFORMATION: human model of 21B12 VL

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
            100                 105                 110

Lys

<210> SEQ ID NO 44
<211> LENGTH: 8
<212> TYPE: PRT
<213> ORGANISM: Artificial Sequence
<220> FEATURE:
<223> OTHER INFORMATION: 16B5 CDRH1

<400> SEQUENCE: 44

Gly Phe Asn Ile Lys Asp Ile Tyr
1               5
```

<210> SEQ ID NO 45
<211> LENGTH: 8
<212> TYPE: PRT
<213> ORGANISM: Artificial Sequence
<220> FEATURE:
<223> OTHER INFORMATION: 16B5 CDRH2

<400> SEQUENCE: 45

Ile Asp Pro Ala Tyr Gly Asn Thr
1               5

<210> SEQ ID NO 46
<211> LENGTH: 10
<212> TYPE: PRT
<213> ORGANISM: Artificial Sequence
<220> FEATURE:
<223> OTHER INFORMATION: 16B5 CDRH3
<220> FEATURE:
<221> NAME/KEY: MISC_FEATURE
<222> LOCATION: (1)..(1)
<223> OTHER INFORMATION: Xaa is A
<220> FEATURE:
<221> NAME/KEY: MISC_FEATURE
<222> LOCATION: (2)..(2)
<223> OTHER INFORMATION: Xaa is R

<400> SEQUENCE: 46

Xaa Xaa Arg Tyr Asp Thr Ala Met Asp Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: 16B5 CDRL1

<400> SEQUENCE: 47

Gln Ser Leu Leu Asn Ser Arg Thr Arg Lys Asn Tyr
1               5                   10

<210> SEQ ID NO 48
<211> LENGTH: 435
<212> TYPE: PRT
<213> ORGANISM: Homo sapiens
<300> PUBLICATION INFORMATION:
<308> DATABASE ACCESSION NUMBER: NP_001822
<309> DATABASE ENTRY DATE: 1991-05-01
<313> RELEVANT RESIDUES IN SEQ ID NO: (1)..(435)

<400> SEQUENCE: 48

Trp Glu Ser Gly Gln Val Leu Gly Asp Gln Thr Val Ser Asp Asn Glu
1               5                   10                  15

Leu Gln Glu Met Ser Asn Gln Gly Ser Lys Tyr Val Asn Lys Glu Ile
            20                  25                  30

Gln Asn Ala Val Asn Gly Val Lys Gln Ile Lys Thr Leu Ile Glu Lys
        35                  40                  45

Thr Asn Glu Glu Arg Lys Thr Leu Leu Ser Asn Leu Glu Glu Ala Lys
    50                  55                  60

Lys Lys Lys Glu Asp Ala Leu Asn Glu Thr Arg Glu Ser Glu Thr Lys
65                  70                  75                  80

Leu Lys Glu Leu Pro Gly Val Cys Asn Glu Thr Met Met Ala Leu Trp
                85                  90                  95

Glu Glu Cys Lys Pro Cys Leu Lys Gln Thr Cys Met Lys Phe Tyr Ala
            100                 105                 110

Arg Val Cys Arg Ser Gly Ser Gly Leu Val Gly Arg Gln Leu Glu Glu
            115                 120                 125

Phe Leu Asn Gln Ser Ser Pro Phe Tyr Phe Trp Met Asn Gly Asp Arg
        130                 135                 140

Ile Asp Ser Leu Leu Glu Asn Asp Arg Gln Gln Thr His Met Leu Asp
145                 150                 155                 160

Val Met Gln Asp His Phe Ser Arg Ala Ser Ser Ile Ile Asp Glu Leu
                165                 170                 175

Phe Gln Asp Arg Phe Phe Thr Arg Glu Pro Gln Asp Thr Tyr His Tyr
            180                 185                 190

Leu Pro Phe Ser Leu Pro His Arg Arg Pro His Phe Phe Pro Lys
        195                 200                 205

Ser Arg Ile Val Arg Ser Leu Met Pro Phe Ser Pro Tyr Glu Pro Leu
210                 215                 220

Asn Phe His Ala Met Phe Gln Pro Phe Leu Glu Met Ile His Glu Ala
225                 230                 235                 240

Gln Gln Ala Met Asp Ile His Phe His Ser Pro Ala Phe Gln His Pro
                245                 250                 255

Pro Thr Glu Phe Ile Arg Glu Gly Asp Asp Asp Arg Thr Val Cys Arg
            260                 265                 270

Glu Ile Arg His Asn Ser Thr Gly Cys Leu Arg Met Lys Asp Gln Cys
275                 280                 285

Asp Lys Cys Arg Glu Ile Leu Ser Val Asp Cys Ser Thr Asn Asn Pro
        290                 295                 300

Ser Gln Ala Lys Leu Arg Arg Glu Leu Asp Glu Ser Leu Gln Val Ala
305                 310                 315                 320

Glu Arg Leu Thr Arg Lys Tyr Asn Glu Leu Leu Lys Ser Tyr Gln Trp
                325                 330                 335

Lys Met Leu Asn Thr Ser Ser Leu Leu Glu Gln Leu Asn Glu Gln Phe
            340                 345                 350

Asn Trp Val Ser Arg Leu Ala Asn Leu Thr Gln Gly Glu Asp Gln Tyr
        355                 360                 365

Tyr Leu Arg Val Thr Thr Val Ala Ser His Thr Ser Asp Ser Asp Val
370                 375                 380

Pro Ser Gly Val Thr Glu Val Val Lys Leu Phe Asp Ser Asp Pro
385                 390                 395                 400

Ile Thr Val Thr Val Pro Val Glu Val Ser Arg Lys Asn Pro Lys Phe
                405                 410                 415

Met Glu Thr Val Ala Gly Lys Ala Leu Gln Gly Tyr Arg Lys Lys His
            420                 425                 430

Arg Glu Glu
        435

<210> SEQ ID NO 49
<211> LENGTH: 8
<212> TYPE: PRT
<213> ORGANISM: Artificial Sequence
<220> FEATURE:
<223> OTHER INFORMATION: 16B5 CDRL3

<400> SEQUENCE: 49

Lys Gln Ser Tyr Asn Leu Trp Thr
1               5

<210> SEQ ID NO 50
<211> LENGTH: 8

```
<212> TYPE: PRT
<213> ORGANISM: Artificial Sequence
<220> FEATURE:
<223> OTHER INFORMATION: 21B12 CDRH1

<400> SEQUENCE: 50

Gly Tyr Thr Phe Thr Asn Tyr Gly
1               5

<210> SEQ ID NO 51
<211> LENGTH: 8
<212> TYPE: PRT
<213> ORGANISM: Artificial Sequence
<220> FEATURE:
<223> OTHER INFORMATION: 21B12 CDRH2

<400> SEQUENCE: 51

Ile Asn Thr Tyr Thr Gly Glu Pro
1               5

<210> SEQ ID NO 52
<211> LENGTH: 11
<212> TYPE: PRT
<213> ORGANISM: Artificial Sequence
<220> FEATURE:
<223> OTHER INFORMATION: 21B12 CDRH3
<220> FEATURE:
<221> NAME/KEY: MISC_FEATURE
<222> LOCATION: (1)..(1)
<223> OTHER INFORMATION: Xaa is A
<220> FEATURE:
<221> NAME/KEY: MISC_FEATURE
<222> LOCATION: (2)..(2)
<223> OTHER INFORMATION: Xaa is R

<400> SEQUENCE: 52

Xaa Xaa Asp Gly Phe Leu Tyr Phe Phe Asp Tyr
1               5                   10

<210> SEQ ID NO 53
<211> LENGTH: 12
<212> TYPE: PRT
<213> ORGANISM: Artificial Sequence
<220> FEATURE:
<223> OTHER INFORMATION: 21B12 CDRL1

<400> SEQUENCE: 53

Gln Ser Leu Leu Tyr Ser Ser Asn Gln Lys Asn Tyr
1               5                   10

<210> SEQ ID NO 54
<211> LENGTH: 435
<212> TYPE: PRT
<213> ORGANISM: Mus musculus
<300> PUBLICATION INFORMATION:
<308> DATABASE ACCESSION NUMBER: NP_038520
<309> DATABASE ENTRY DATE: 1989-09-01
<313> RELEVANT RESIDUES IN SEQ ID NO: (1)..(435)

<400> SEQUENCE: 54

Trp Asp Asn Gly Met Val Leu Gly Glu Gln Glu Val Ser Asp Asn Glu
1               5                   10                  15

Leu Gln Glu Leu Ser Thr Gln Gly Ser Arg Tyr Ile Asn Lys Glu Ile
            20                  25                  30

Gln Asn Ala Val Gln Gly Val Lys His Ile Lys Thr Leu Ile Glu Lys
        35                  40                  45

Thr Asn Ala Glu Arg Lys Ser Leu Leu Asn Ser Leu Glu Glu Ala Lys
```

```
                50                  55                  60
Lys Lys Lys Glu Asp Ala Leu Glu Asp Thr Arg Asp Ser Glu Met Lys
 65                  70                  75                  80

Leu Lys Ala Phe Pro Glu Val Cys Asn Glu Thr Met Met Ala Leu Trp
                 85                  90                  95

Glu Glu Cys Lys Pro Cys Leu Lys His Thr Cys Met Lys Phe Tyr Ala
                100                 105                 110

Arg Val Cys Arg Ser Gly Ser Gly Leu Val Gly Gln Gln Leu Glu Glu
            115                 120                 125

Phe Leu Asn Gln Ser Ser Pro Phe Tyr Phe Trp Met Asn Gly Asp Arg
        130                 135                 140

Ile Asp Ser Leu Leu Glu Ser Asp Arg Gln Gln Ser Gln Val Leu Asp
145                 150                 155                 160

Ala Met Gln Asp Ser Phe Ala Arg Ala Ser Gly Ile Ile Asp Thr Leu
                165                 170                 175

Phe Gln Asp Arg Phe Phe Ala Arg Glu Leu His Asp Pro His Tyr Phe
            180                 185                 190

Ser Pro Ile Gly Phe Pro His Lys Arg Pro His Phe Leu Tyr Pro Lys
        195                 200                 205

Ser Arg Leu Val Arg Ser Leu Met Ser Pro Ser His Tyr Gly Pro Pro
    210                 215                 220

Ser Phe His Asn Met Phe Gln Pro Phe Glu Met Ile His Gln Ala
225                 230                 235                 240

Gln Gln Ala Met Asp Val Gln Leu His Ser Pro Ala Phe Gln Phe Pro
                245                 250                 255

Asp Val Asp Phe Leu Arg Glu Gly Glu Asp Asp Arg Thr Val Cys Lys
            260                 265                 270

Glu Ile Arg Arg Asn Ser Thr Gly Cys Leu Lys Met Lys Gly Gln Cys
        275                 280                 285

Glu Lys Cys Gln Glu Ile Leu Ser Val Asp Cys Ser Thr Asn Asn Pro
    290                 295                 300

Ala Gln Ala Asn Leu Arg Gln Glu Leu Asn Asp Ser Leu Gln Val Ala
305                 310                 315                 320

Glu Arg Leu Thr Glu Gln Tyr Lys Glu Leu Leu Gln Ser Phe Gln Ser
                325                 330                 335

Lys Met Leu Asn Thr Ser Ser Leu Leu Glu Gln Leu Asn Asp Gln Phe
            340                 345                 350

Asn Trp Val Ser Gln Leu Ala Asn Leu Thr Gln Gly Glu Asp Lys Tyr
        355                 360                 365

Tyr Leu Arg Val Ser Thr Val Thr Thr His Ser Ser Asp Ser Glu Val
    370                 375                 380

Pro Ser Arg Val Thr Glu Val Val Lys Leu Phe Asp Ser Asp Pro
385                 390                 395                 400

Ile Thr Val Val Leu Pro Glu Glu Val Ser Lys Asp Asn Pro Lys Phe
                405                 410                 415

Met Asp Thr Val Ala Glu Lys Ala Leu Gln Glu Tyr Arg Arg Lys Ser
            420                 425                 430

Arg Ala Glu
        435

<210> SEQ ID NO 55
<211> LENGTH: 9
<212> TYPE: PRT
<213> ORGANISM: Artificial Sequence
```

```
<220> FEATURE:
<223> OTHER INFORMATION: 21B12 CDRL3

<400> SEQUENCE: 55

Gln Gln Tyr Tyr Ile Tyr Pro Arg Thr
1               5

<210> SEQ ID NO 56
<211> LENGTH: 435
<212> TYPE: PRT
<213> ORGANISM: Artificial Sequence
<220> FEATURE:
<223> OTHER INFORMATION: clusterin variant
<220> FEATURE:
<221> NAME/KEY: MISC_FEATURE
<222> LOCATION: (2)..(2)
<223> OTHER INFORMATION: Xaa is a conservative amino acid substitution
<220> FEATURE:
<221> NAME/KEY: MISC_FEATURE
<222> LOCATION: (3)..(3)
<223> OTHER INFORMATION: Xaa is a conservative amino acid substitution
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is a conservative amino acid substitution
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is a conservative amino acid substitution
<220> FEATURE:
<221> NAME/KEY: MISC_FEATURE
<222> LOCATION: (22)..(22)
<223> OTHER INFORMATION: Xaa is any amino acid
<220> FEATURE:
<221> NAME/KEY: MISC_FEATURE
<222> LOCATION: (26)..(26)
<223> OTHER INFORMATION: Xaa is a conservative amino acid substitution
<220> FEATURE:
<221> NAME/KEY: MISC_FEATURE
<222> LOCATION: (28)..(28)
<223> OTHER INFORMATION: Xaa is a conservative amino acid substitution
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is any amino acid
<220> FEATURE:
<221> NAME/KEY: MISC_FEATURE
<222> LOCATION: (55)..(55)
<223> OTHER INFORMATION: Xaa is a conservative amino acid substitution
<220> FEATURE:
<221> NAME/KEY: MISC_FEATURE
<222> LOCATION: (58)..(58)
<223> OTHER INFORMATION: Xaa is a conservative amino acid substitution
<220> FEATURE:
<221> NAME/KEY: MISC_FEATURE
<222> LOCATION: (59)..(59)
<223> OTHER INFORMATION: Xaa is a conservative amino acid substitution
<220> FEATURE:
<221> NAME/KEY: MISC_FEATURE
<222> LOCATION: (72)..(72)
<223> OTHER INFORMATION: Xaa is any amino acid
```

-continued

```
<220> FEATURE:
<221> NAME/KEY: MISC_FEATURE
<222> LOCATION: (73)..(73)
<223> OTHER INFORMATION: Xaa is a conservative amino acid substitution
<220> FEATURE:
<221> NAME/KEY: MISC_FEATURE
<222> LOCATION: (76)..(76)
<223> OTHER INFORMATION: Xaa is a conservative amino acid substitution
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (83)..(83)
<223> OTHER INFORMATION: Xaa is any amino acid
<220> FEATURE:
<221> NAME/KEY: MISC_FEATURE
<222> LOCATION: (84)..(84)
<223> OTHER INFORMATION: Xaa is any amino acid
<220> FEATURE:
<221> NAME/KEY: MISC_FEATURE
<222> LOCATION: (86)..(86)
<223> OTHER INFORMATION: Xaa is any amino acid
<220> FEATURE:
<221> NAME/KEY: MISC_FEATURE
<222> LOCATION: (105)..(105)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is a conservative amino acid substitution
<220> FEATURE:
<221> NAME/KEY: MISC_FEATURE
<222> LOCATION: (151)..(151)
<223> OTHER INFORMATION: Xaa is a conservative amino acid substitution
<220> FEATURE:
<221> NAME/KEY: MISC_FEATURE
<222> LOCATION: (156)..(156)
<223> OTHER INFORMATION: Xaa is a conservative amino acid substitution
<220> FEATURE:
<221> NAME/KEY: MISC_FEATURE
<222> LOCATION: (157)..(157)
<223> OTHER INFORMATION: Xaa is any amino acid
<220> FEATURE:
<221> NAME/KEY: MISC_FEATURE
<222> LOCATION: (158)..(158)
<223> OTHER INFORMATION: Xaa is a conservative amino acid substitution
<220> FEATURE:
<221> NAME/KEY: MISC_FEATURE
<222> LOCATION: (161)..(161)
<223> OTHER INFORMATION: Xaa is any amino acid
<220> FEATURE:
<221> NAME/KEY: MISC_FEATURE
<222> LOCATION: (165)..(165)
<223> OTHER INFORMATION: Xaa is any amino acid
<220> FEATURE:
<221> NAME/KEY: MISC_FEATURE
<222> LOCATION: (167)..(167)
<223> OTHER INFORMATION: Xaa is a conservative amino acid substitution
<220> FEATURE:
<221> NAME/KEY: MISC_FEATURE
<222> LOCATION: (171)..(171)
<223> OTHER INFORMATION: Xaa is any amino acid
<220> FEATURE:
<221> NAME/KEY: MISC_FEATURE
<222> LOCATION: (175)..(175)
<223> OTHER INFORMATION: Xaa is any amino acid
<220> FEATURE:
<221> NAME/KEY: MISC_FEATURE
<222> LOCATION: (183)..(183)
<223> OTHER INFORMATION: Xaa is any amino acid
<220> FEATURE:
<221> NAME/KEY: MISC_FEATURE
<222> LOCATION: (186)..(186)
<223> OTHER INFORMATION: Xaa is any amino acid
<220> FEATURE:
<221> NAME/KEY: MISC_FEATURE
<222> LOCATION: (187)..(187)
```

```
<223> OTHER INFORMATION: Xaa is any amino acid
<220> FEATURE:
<221> NAME/KEY: MISC_FEATURE
<222> LOCATION: (189)..(189)
<223> OTHER INFORMATION: Xaa is any amino acid
<220> FEATURE:
<221> NAME/KEY: MISC_FEATURE
<222> LOCATION: (190)..(190)
<223> OTHER INFORMATION: Xaa is a conservative amino acid substitution
<220> FEATURE:
<221> NAME/KEY: MISC_FEATURE
<222> LOCATION: (191)..(191)
<223> OTHER INFORMATION: Xaa is a conservative amino acid substitution
<220> FEATURE:
<221> NAME/KEY: MISC_FEATURE
<222> LOCATION: (192)..(192)
<223> OTHER INFORMATION: Xaa is a conservative amino acid substitution
<220> FEATURE:
<221> NAME/KEY: MISC_FEATURE
<222> LOCATION: (193)..(193)
<223> OTHER INFORMATION: Xaa is any amino acid
<220> FEATURE:
<221> NAME/KEY: MISC_FEATURE
<222> LOCATION: (195)..(195)
<223> OTHER INFORMATION: Xaa is any amino acid
<220> FEATURE:
<221> NAME/KEY: MISC_FEATURE
<222> LOCATION: (196)..(196)
<223> OTHER INFORMATION: Xaa is any amino acid
<220> FEATURE:
<221> NAME/KEY: MISC_FEATURE
<222> LOCATION: (197)..(197)
<223> OTHER INFORMATION: Xaa is any amino acid
<220> FEATURE:
<221> NAME/KEY: MISC_FEATURE
<222> LOCATION: (200)..(200)
<223> OTHER INFORMATION: Xaa is a conservative amino acid substitution
<220> FEATURE:
<221> NAME/KEY: MISC_FEATURE
<222> LOCATION: (205)..(205)
<223> OTHER INFORMATION: Xaa is any amino acid
<220> FEATURE:
<221> NAME/KEY: MISC_FEATURE
<222> LOCATION: (206)..(206)
<223> OTHER INFORMATION: Xaa is a conservative amino acid substitution
<220> FEATURE:
<221> NAME/KEY: MISC_FEATURE
<222> LOCATION: (211)..(211)
<223> OTHER INFORMATION: Xaa is a conservative amino acid substitution
<220> FEATURE:
<221> NAME/KEY: MISC_FEATURE
<222> LOCATION: (217)..(217)
<223> OTHER INFORMATION: Xaa is any amino acid
<220> FEATURE:
<221> NAME/KEY: MISC_FEATURE
<222> LOCATION: (218)..(218)
<223> OTHER INFORMATION: Xaa is any amino acid
<220> FEATURE:
<221> NAME/KEY: MISC_FEATURE
<222> LOCATION: (220)..(220)
<223> OTHER INFORMATION: Xaa is any amino acid
<220> FEATURE:
<221> NAME/KEY: MISC_FEATURE
<222> LOCATION: (222)..(222)
<223> OTHER INFORMATION: Xaa is any amino acid
<220> FEATURE:
<221> NAME/KEY: MISC_FEATURE
<222> LOCATION: (224)..(224)
<223> OTHER INFORMATION: Xaa is any amino acid
<220> FEATURE:
<221> NAME/KEY: MISC_FEATURE
<222> LOCATION: (225)..(225)
<223> OTHER INFORMATION: Xaa is a conservative amino acid substitution
<220> FEATURE:
<221> NAME/KEY: MISC_FEATURE
<222> LOCATION: (228)..(228)
<223> OTHER INFORMATION: Xaa is any amino acid
<220> FEATURE:
<221> NAME/KEY: MISC_FEATURE
```

```
<222> LOCATION: (234)..(234)
<223> OTHER INFORMATION: Xaa is any amino acid
<220> FEATURE:
<221> NAME/KEY: MISC_FEATURE
<222> LOCATION: (239)..(239)
<223> OTHER INFORMATION: Xaa is a conservative amino acid substitution
<220> FEATURE:
<221> NAME/KEY: MISC_FEATURE
<222> LOCATION: (246)..(246)
<223> OTHER INFORMATION: Xaa is a conservative amino acid substitution
<220> FEATURE:
<221> NAME/KEY: MISC_FEATURE
<222> LOCATION: (247)..(247)
<223> OTHER INFORMATION: Xaa is any amino acid
<220> FEATURE:
<221> NAME/KEY: MISC_FEATURE
<222> LOCATION: (248)..(248)
<223> OTHER INFORMATION: Xaa is any amino acid
<220> FEATURE:
<221> NAME/KEY: MISC_FEATURE
<222> LOCATION: (255)..(255)
<223> OTHER INFORMATION: Xaa is any amino acid
<220> FEATURE:
<221> NAME/KEY: MISC_FEATURE
<222> LOCATION: (257)..(257)
<223> OTHER INFORMATION: Xaa is any amino acid
<220> FEATURE:
<221> NAME/KEY: MISC_FEATURE
<222> LOCATION: (258)..(258)
<223> OTHER INFORMATION: Xaa is any amino acid
<220> FEATURE:
<221> NAME/KEY: MISC_FEATURE
<222> LOCATION: (259)..(259)
<223> OTHER INFORMATION: Xaa is a conservative amino acid substitution
<220> FEATURE:
<221> NAME/KEY: MISC_FEATURE
<222> LOCATION: (261)..(261)
<223> OTHER INFORMATION: Xaa is a conservative amino acid substitution
<220> FEATURE:
<221> NAME/KEY: MISC_FEATURE
<222> LOCATION: (265)..(265)
<223> OTHER INFORMATION: Xaa is a conservative amino acid substitution
<220> FEATURE:
<221> NAME/KEY: MISC_FEATURE
<222> LOCATION: (272)..(272)
<223> OTHER INFORMATION: Xaa is a conservative amino acid substitution
<220> FEATURE:
<221> NAME/KEY: MISC_FEATURE
<222> LOCATION: (276)..(276)
<223> OTHER INFORMATION: Xaa is any amino acid
<220> FEATURE:
<221> NAME/KEY: MISC_FEATURE
<222> LOCATION: (283)..(283)
<223> OTHER INFORMATION: Xaa is a conservative amino acid substitution
<220> FEATURE:
<221> NAME/KEY: MISC_FEATURE
<222> LOCATION: (286)..(286)
<223> OTHER INFORMATION: Xaa is any amino acid
<220> FEATURE:
<221> NAME/KEY: MISC_FEATURE
<222> LOCATION: (289)..(289)
<223> OTHER INFORMATION: Xaa is a conservative amino acid substitution
<220> FEATURE:
<221> NAME/KEY: MISC_FEATURE
<222> LOCATION: (292)..(292)
<223> OTHER INFORMATION: Xaa is a conservative amino acid substitution
<220> FEATURE:
<221> NAME/KEY: MISC_FEATURE
<222> LOCATION: (305)..(305)
<223> OTHER INFORMATION: Xaa is a conservative amino acid substitution
<220> FEATURE:
<221> NAME/KEY: MISC_FEATURE
<222> LOCATION: (308)..(308)
<223> OTHER INFORMATION: Xaa is any amino acid
<220> FEATURE:
<221> NAME/KEY: MISC_FEATURE
<222> LOCATION: (311)..(311)
<223> OTHER INFORMATION: Xaa is a conservative amino acid substitution
<220> FEATURE:
```

```
<221> NAME/KEY: MISC_FEATURE
<222> LOCATION: (314)..(314)
<223> OTHER INFORMATION: Xaa is a conservative amino acid substitution
<220> FEATURE:
<221> NAME/KEY: MISC_FEATURE
<222> LOCATION: (315)..(315)
<223> OTHER INFORMATION: Xaa is a conservative amino acid substitution
<220> FEATURE:
<221> NAME/KEY: MISC_FEATURE
<222> LOCATION: (325)..(325)
<223> OTHER INFORMATION: Xaa is any amino acid
<220> FEATURE:
<221> NAME/KEY: MISC_FEATURE
<222> LOCATION: (326)..(326)
<223> OTHER INFORMATION: Xaa is a conservative amino acid substitution
<220> FEATURE:
<221> NAME/KEY: MISC_FEATURE
<222> LOCATION: (328)..(328)
<223> OTHER INFORMATION: Xaa is any amino acid
<220> FEATURE:
<221> NAME/KEY: MISC_FEATURE
<222> LOCATION: (332)..(332)
<223> OTHER INFORMATION: Xaa is a conservative amino acid substitution
<220> FEATURE:
<221> NAME/KEY: MISC_FEATURE
<222> LOCATION: (334)..(334)
<223> OTHER INFORMATION: Xaa is a conservative amino acid substitution
<220> FEATURE:
<221> NAME/KEY: MISC_FEATURE
<222> LOCATION: (336)..(336)
<223> OTHER INFORMATION: Xaa is any amino acid
<220> FEATURE:
<221> NAME/KEY: MISC_FEATURE
<222> LOCATION: (350)..(350)
<223> OTHER INFORMATION: Xaa is a conservative amino acid substitution
<220> FEATURE:
<221> NAME/KEY: MISC_FEATURE
<222> LOCATION: (357)..(357)
<223> OTHER INFORMATION: Xaa is a conservative amino acid substitution
<220> FEATURE:
<221> NAME/KEY: MISC_FEATURE
<222> LOCATION: (367)..(367)
<223> OTHER INFORMATION: Xaa is a conservative amino acid substitution
<220> FEATURE:
<221> NAME/KEY: MISC_FEATURE
<222> LOCATION: (373)..(373)
<223> OTHER INFORMATION: Xaa is a conservative amino acid substitution
<220> FEATURE:
<221> NAME/KEY: MISC_FEATURE
<222> LOCATION: (376)..(376)
<223> OTHER INFORMATION: Xaa is any amino acid
<220> FEATURE:
<221> NAME/KEY: MISC_FEATURE
<222> LOCATION: (377)..(377)
<223> OTHER INFORMATION: Xaa is a conservative amino acid substitution
<220> FEATURE:
<221> NAME/KEY: MISC_FEATURE
<222> LOCATION: (379)..(379)
<223> OTHER INFORMATION: Xaa is a conservative amino acid substitution
<220> FEATURE:
<221> NAME/KEY: MISC_FEATURE
<222> LOCATION: (383)..(383)
<223> OTHER INFORMATION: Xaa is a conservative amino acid substitution
<220> FEATURE:
<221> NAME/KEY: MISC_FEATURE
<222> LOCATION: (387)..(387)
<223> OTHER INFORMATION: Xaa is any amino acid
<220> FEATURE:
<221> NAME/KEY: MISC_FEATURE
<222> LOCATION: (404)..(404)
<223> OTHER INFORMATION: Xaa is any amino acid
<220> FEATURE:
<221> NAME/KEY: MISC_FEATURE
<222> LOCATION: (405)..(405)
<223> OTHER INFORMATION: Xaa is a conservative amino acid substitution
<220> FEATURE:
<221> NAME/KEY: MISC_FEATURE
<222> LOCATION: (407)..(407)
<223> OTHER INFORMATION: Xaa is any amino acid
```

```
<220> FEATURE:
<221> NAME/KEY: MISC_FEATURE
<222> LOCATION: (411)..(411)
<223> OTHER INFORMATION: Xaa is a conservative amino acid substitution
<220> FEATURE:
<221> NAME/KEY: MISC_FEATURE
<222> LOCATION: (412)..(412)
<223> OTHER INFORMATION: Xaa is any amino acid
<220> FEATURE:
<221> NAME/KEY: MISC_FEATURE
<222> LOCATION: (418)..(418)
<223> OTHER INFORMATION: Xaa is a conservative amino acid substitution
<220> FEATURE:
<221> NAME/KEY: MISC_FEATURE
<222> LOCATION: (430)..(430)
<223> OTHER INFORMATION: Xaa is a conservative amino acid substitution
<220> FEATURE:
<221> NAME/KEY: MISC_FEATURE
<222> LOCATION: (432)..(432)
<223> OTHER INFORMATION: Xaa is any amino acid
<220> FEATURE:
<221> NAME/KEY: MISC_FEATURE
<222> LOCATION: (434)..(434)
<223> OTHER INFORMATION: Xaa is any amino acid

<400> SEQUENCE: 56

Trp Xaa Xaa Gly Xaa Val Leu Gly Xaa Gln Xaa Val Ser Asp Asn Glu
1               5                   10                  15

Leu Gln Glu Xaa Ser Xaa Gln Gly Ser Xaa Tyr Xaa Asn Lys Glu Ile
            20                  25                  30

Gln Asn Ala Val Xaa Gly Val Lys Xaa Ile Lys Thr Leu Ile Glu Lys
        35                  40                  45

Thr Asn Xaa Glu Arg Lys Xaa Leu Leu Xaa Xaa Leu Glu Glu Ala Lys
50                  55                  60

Lys Lys Lys Glu Asp Ala Leu Xaa Xaa Thr Arg Xaa Ser Glu Xaa Lys
65                  70                  75                  80

Leu Lys Xaa Xaa Pro Xaa Val Cys Asn Glu Thr Met Met Ala Leu Trp
                85                  90                  95

Glu Glu Cys Lys Pro Cys Leu Lys Xaa Thr Cys Met Lys Phe Tyr Ala
                100                 105                 110

Arg Val Cys Arg Ser Gly Ser Gly Leu Val Gly Xaa Gln Leu Glu Glu
            115                 120                 125

Phe Leu Asn Gln Ser Ser Pro Phe Tyr Phe Trp Met Asn Gly Asp Arg
130                 135                 140

Ile Asp Ser Leu Leu Glu Xaa Asp Arg Gln Gln Xaa Xaa Xaa Leu Asp
145                 150                 155                 160

Xaa Met Gln Asp Xaa Phe Xaa Arg Ala Ser Xaa Ile Ile Asp Xaa Leu
                165                 170                 175

Phe Gln Asp Arg Phe Phe Xaa Arg Glu Xaa Xaa Asp Xaa Xaa Xaa Xaa
            180                 185                 190

Xaa Pro Xaa Xaa Xaa Pro His Xaa Arg Pro His Phe Xaa Xaa Pro Lys
        195                 200                 205

Ser Arg Xaa Val Arg Ser Leu Met Xaa Xaa Ser Xaa Tyr Xaa Pro Xaa
        210                 215                 220

Xaa Phe His Xaa Met Phe Gln Pro Phe Xaa Glu Met Ile His Xaa Ala
225                 230                 235                 240

Gln Gln Ala Met Asp Xaa Xaa His Ser Pro Ala Phe Gln Xaa Pro
                245                 250                 255

Xaa Xaa Xaa Phe Xaa Arg Glu Gly Xaa Asp Asp Arg Thr Val Cys Xaa
            260                 265                 270

Glu Ile Arg Xaa Asn Ser Thr Gly Cys Leu Xaa Met Lys Xaa Gln Cys
```

```
                    275                 280                 285
Xaa Lys Cys Xaa Glu Ile Leu Ser Val Asp Cys Ser Thr Asn Asn Pro
        290                 295                 300

Xaa Gln Ala Xaa Leu Arg Xaa Glu Leu Xaa Xaa Ser Leu Gln Val Ala
305                 310                 315                 320

Glu Arg Leu Thr Xaa Xaa Tyr Xaa Glu Leu Leu Xaa Ser Xaa Gln Xaa
                325                 330                 335

Lys Met Leu Asn Thr Ser Ser Leu Leu Glu Gln Leu Asn Xaa Gln Phe
        340                 345                 350

Asn Trp Val Ser Xaa Leu Ala Asn Leu Thr Gln Gly Glu Asp Xaa Tyr
                355                 360                 365

Tyr Leu Arg Val Xaa Thr Val Xaa Xaa His Xaa Ser Asp Ser Xaa Val
        370                 375                 380

Pro Ser Xaa Val Thr Glu Val Val Val Lys Leu Phe Asp Ser Asp Pro
385                 390                 395                 400

Ile Thr Val Xaa Xaa Pro Xaa Glu Val Ser Xaa Xaa Asn Pro Lys Phe
                405                 410                 415

Met Xaa Thr Val Ala Glu Lys Ala Leu Gln Glu Tyr Arg Xaa Lys Xaa
        420                 425                 430

Arg Xaa Glu
    435

<210> SEQ ID NO 57
<211> LENGTH: 435
<212> TYPE: PRT
<213> ORGANISM: Artificial Sequence
<220> FEATURE:
<223> OTHER INFORMATION: clusterin variant
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is any amino acid
<220> FEATURE:
<221> NAME/KEY: MISC_FEATURE
<222> LOCATION: (26)..(26)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is any amino acid
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is any amino acid
```

```
<220> FEATURE:
<221> NAME/KEY: MISC_FEATURE
<222> LOCATION: (51)..(51)
<223> OTHER INFORMATION: Xaa is any amino acid
<220> FEATURE:
<221> NAME/KEY: MISC_FEATURE
<222> LOCATION: (55)..(55)
<223> OTHER INFORMATION: Xaa is any amino acid
<220> FEATURE:
<221> NAME/KEY: MISC_FEATURE
<222> LOCATION: (58)..(59)
<223> OTHER INFORMATION: Xaa is any amino acid
<220> FEATURE:
<221> NAME/KEY: MISC_FEATURE
<222> LOCATION: (72)..(73)
<223> OTHER INFORMATION: Xaa is any amino acid
<220> FEATURE:
<221> NAME/KEY: MISC_FEATURE
<222> LOCATION: (76)..(76)
<223> OTHER INFORMATION: Xaa is any amino acid
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (83)..(84)
<223> OTHER INFORMATION: Xaa is any amino acid
<220> FEATURE:
<221> NAME/KEY: MISC_FEATURE
<222> LOCATION: (86)..(86)
<223> OTHER INFORMATION: Xaa is any amino acid
<220> FEATURE:
<221> NAME/KEY: MISC_FEATURE
<222> LOCATION: (105)..(105)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is any amino acid
<220> FEATURE:
<221> NAME/KEY: MISC_FEATURE
<222> LOCATION: (151)..(151)
<223> OTHER INFORMATION: Xaa is any amino acid
<220> FEATURE:
<221> NAME/KEY: MISC_FEATURE
<222> LOCATION: (156)..(158)
<223> OTHER INFORMATION: Xaa is any amino acid
<220> FEATURE:
<221> NAME/KEY: MISC_FEATURE
<222> LOCATION: (161)..(161)
<223> OTHER INFORMATION: Xaa is any amino acid
<220> FEATURE:
<221> NAME/KEY: MISC_FEATURE
<222> LOCATION: (165)..(165)
<223> OTHER INFORMATION: Xaa is any amino acid
<220> FEATURE:
<221> NAME/KEY: MISC_FEATURE
<222> LOCATION: (167)..(167)
<223> OTHER INFORMATION: Xaa is any amino acid
<220> FEATURE:
<221> NAME/KEY: MISC_FEATURE
<222> LOCATION: (171)..(171)
<223> OTHER INFORMATION: Xaa is any amino acid
<220> FEATURE:
<221> NAME/KEY: MISC_FEATURE
<222> LOCATION: (175)..(175)
<223> OTHER INFORMATION: Xaa is any amino acid
<220> FEATURE:
<221> NAME/KEY: MISC_FEATURE
<222> LOCATION: (183)..(183)
<223> OTHER INFORMATION: Xaa is any amino acid
<220> FEATURE:
<221> NAME/KEY: MISC_FEATURE
<222> LOCATION: (186)..(187)
<223> OTHER INFORMATION: Xaa is any amino acid
<220> FEATURE:
<221> NAME/KEY: MISC_FEATURE
<222> LOCATION: (189)..(193)
```

```
<223> OTHER INFORMATION: Xaa is any amino acid
<220> FEATURE:
<221> NAME/KEY: MISC_FEATURE
<222> LOCATION: (195)..(197)
<223> OTHER INFORMATION: Xaa is any amino acid
<220> FEATURE:
<221> NAME/KEY: MISC_FEATURE
<222> LOCATION: (200)..(200)
<223> OTHER INFORMATION: Xaa is any amino acid
<220> FEATURE:
<221> NAME/KEY: MISC_FEATURE
<222> LOCATION: (205)..(206)
<223> OTHER INFORMATION: Xaa is any amino acid
<220> FEATURE:
<221> NAME/KEY: MISC_FEATURE
<222> LOCATION: (211)..(211)
<223> OTHER INFORMATION: Xaa is any amino acid
<220> FEATURE:
<221> NAME/KEY: MISC_FEATURE
<222> LOCATION: (217)..(218)
<223> OTHER INFORMATION: Xaa is any amino acid
<220> FEATURE:
<221> NAME/KEY: MISC_FEATURE
<222> LOCATION: (220)..(220)
<223> OTHER INFORMATION: Xaa is any amino acid
<220> FEATURE:
<221> NAME/KEY: MISC_FEATURE
<222> LOCATION: (222)..(222)
<223> OTHER INFORMATION: Xaa is any amino acid
<220> FEATURE:
<221> NAME/KEY: MISC_FEATURE
<222> LOCATION: (224)..(225)
<223> OTHER INFORMATION: Xaa is any amino acid
<220> FEATURE:
<221> NAME/KEY: MISC_FEATURE
<222> LOCATION: (228)..(228)
<223> OTHER INFORMATION: Xaa is any amino acid
<220> FEATURE:
<221> NAME/KEY: MISC_FEATURE
<222> LOCATION: (234)..(234)
<223> OTHER INFORMATION: Xaa is any amino acid
<220> FEATURE:
<221> NAME/KEY: MISC_FEATURE
<222> LOCATION: (239)..(239)
<223> OTHER INFORMATION: Xaa is any amino acid
<220> FEATURE:
<221> NAME/KEY: MISC_FEATURE
<222> LOCATION: (246)..(248)
<223> OTHER INFORMATION: Xaa is any amino acid
<220> FEATURE:
<221> NAME/KEY: MISC_FEATURE
<222> LOCATION: (255)..(255)
<223> OTHER INFORMATION: Xaa is any amino acid
<220> FEATURE:
<221> NAME/KEY: MISC_FEATURE
<222> LOCATION: (257)..(259)
<223> OTHER INFORMATION: Xaa is any amino acid
<220> FEATURE:
<221> NAME/KEY: MISC_FEATURE
<222> LOCATION: (261)..(261)
<223> OTHER INFORMATION: Xaa is any amino acid
<220> FEATURE:
<221> NAME/KEY: MISC_FEATURE
<222> LOCATION: (265)..(265)
<223> OTHER INFORMATION: Xaa is any amino acid
<220> FEATURE:
<221> NAME/KEY: MISC_FEATURE
<222> LOCATION: (272)..(272)
<223> OTHER INFORMATION: Xaa is any amino acid
<220> FEATURE:
<221> NAME/KEY: MISC_FEATURE
<222> LOCATION: (276)..(276)
<223> OTHER INFORMATION: Xaa is any amino acid
<220> FEATURE:
<221> NAME/KEY: MISC_FEATURE
<222> LOCATION: (283)..(283)
<223> OTHER INFORMATION: Xaa is any amino acid
<220> FEATURE:
<221> NAME/KEY: MISC_FEATURE
```

```
<222> LOCATION: (286)..(286)
<223> OTHER INFORMATION: Xaa is any amino acid
<220> FEATURE:
<221> NAME/KEY: MISC_FEATURE
<222> LOCATION: (289)..(289)
<223> OTHER INFORMATION: Xaa is any amino acid
<220> FEATURE:
<221> NAME/KEY: MISC_FEATURE
<222> LOCATION: (292)..(292)
<223> OTHER INFORMATION: Xaa is any amino acid
<220> FEATURE:
<221> NAME/KEY: MISC_FEATURE
<222> LOCATION: (305)..(305)
<223> OTHER INFORMATION: Xaa is any amino acid
<220> FEATURE:
<221> NAME/KEY: MISC_FEATURE
<222> LOCATION: (308)..(308)
<223> OTHER INFORMATION: Xaa is any amino acid
<220> FEATURE:
<221> NAME/KEY: MISC_FEATURE
<222> LOCATION: (311)..(311)
<223> OTHER INFORMATION: Xaa is any amino acid
<220> FEATURE:
<221> NAME/KEY: MISC_FEATURE
<222> LOCATION: (314)..(315)
<223> OTHER INFORMATION: Xaa is any amino acid
<220> FEATURE:
<221> NAME/KEY: MISC_FEATURE
<222> LOCATION: (325)..(326)
<223> OTHER INFORMATION: Xaa is any amino acid
<220> FEATURE:
<221> NAME/KEY: MISC_FEATURE
<222> LOCATION: (328)..(328)
<223> OTHER INFORMATION: Xaa is any amino acid
<220> FEATURE:
<221> NAME/KEY: MISC_FEATURE
<222> LOCATION: (332)..(332)
<223> OTHER INFORMATION: Xaa is any amino acid
<220> FEATURE:
<221> NAME/KEY: MISC_FEATURE
<222> LOCATION: (334)..(334)
<223> OTHER INFORMATION: Xaa is any amino acid
<220> FEATURE:
<221> NAME/KEY: MISC_FEATURE
<222> LOCATION: (336)..(336)
<223> OTHER INFORMATION: Xaa is any amino acid
<220> FEATURE:
<221> NAME/KEY: MISC_FEATURE
<222> LOCATION: (350)..(350)
<223> OTHER INFORMATION: Xaa is any amino acid
<220> FEATURE:
<221> NAME/KEY: MISC_FEATURE
<222> LOCATION: (357)..(357)
<223> OTHER INFORMATION: Xaa is any amino acid
<220> FEATURE:
<221> NAME/KEY: MISC_FEATURE
<222> LOCATION: (367)..(367)
<223> OTHER INFORMATION: Xaa is any amino acid
<220> FEATURE:
<221> NAME/KEY: MISC_FEATURE
<222> LOCATION: (373)..(373)
<223> OTHER INFORMATION: Xaa is any amino acid
<220> FEATURE:
<221> NAME/KEY: MISC_FEATURE
<222> LOCATION: (376)..(377)
<223> OTHER INFORMATION: Xaa is any amino acid
<220> FEATURE:
<221> NAME/KEY: MISC_FEATURE
<222> LOCATION: (379)..(379)
<223> OTHER INFORMATION: Xaa is any amino acid
<220> FEATURE:
<221> NAME/KEY: MISC_FEATURE
<222> LOCATION: (383)..(383)
<223> OTHER INFORMATION: Xaa is any amino acid
<220> FEATURE:
<221> NAME/KEY: MISC_FEATURE
<222> LOCATION: (387)..(387)
<223> OTHER INFORMATION: Xaa is any amino acid
<220> FEATURE:
```

<220> FEATURE:
<221> NAME/KEY: MISC_FEATURE
<222> LOCATION: (404)..(405)
<223> OTHER INFORMATION: Xaa is any amino acid
<220> FEATURE:
<221> NAME/KEY: MISC_FEATURE
<222> LOCATION: (407)..(407)
<223> OTHER INFORMATION: Xaa is any amino acid
<220> FEATURE:
<221> NAME/KEY: MISC_FEATURE
<222> LOCATION: (411)..(412)
<223> OTHER INFORMATION: Xaa is any amino acid
<220> FEATURE:
<221> NAME/KEY: MISC_FEATURE
<222> LOCATION: (418)..(418)
<223> OTHER INFORMATION: Xaa is any amino acid
<220> FEATURE:
<221> NAME/KEY: MISC_FEATURE
<222> LOCATION: (430)..(430)
<223> OTHER INFORMATION: Xaa is any amino acid
<220> FEATURE:
<221> NAME/KEY: MISC_FEATURE
<222> LOCATION: (432)..(432)
<223> OTHER INFORMATION: Xaa is any amino acid
<220> FEATURE:
<221> NAME/KEY: MISC_FEATURE
<222> LOCATION: (434)..(434)
<223> OTHER INFORMATION: Xaa is any amino acid

<400> SEQUENCE: 57

Trp Xaa Xaa Gly Xaa Val Leu Gly Xaa Gln Xaa Val Ser Asp Asn Glu
1               5                   10                  15

Leu Gln Glu Xaa Ser Xaa Gln Gly Ser Xaa Tyr Xaa Asn Lys Glu Ile
                20                  25                  30

Gln Asn Ala Val Xaa Gly Val Lys Xaa Ile Lys Thr Leu Ile Glu Lys
            35                  40                  45

Thr Asn Xaa Glu Arg Lys Xaa Leu Leu Xaa Xaa Leu Glu Glu Ala Lys
    50                  55                  60

Lys Lys Lys Glu Asp Ala Leu Xaa Xaa Thr Arg Xaa Ser Glu Xaa Lys
65                  70                  75                  80

Leu Lys Xaa Xaa Pro Xaa Val Cys Asn Glu Thr Met Met Ala Leu Trp
                85                  90                  95

Glu Glu Cys Lys Pro Cys Leu Lys Xaa Thr Cys Met Lys Phe Tyr Ala
                100                 105                 110

Arg Val Cys Arg Ser Gly Ser Gly Leu Val Gly Xaa Gln Leu Glu Glu
            115                 120                 125

Phe Leu Asn Gln Ser Ser Pro Phe Tyr Phe Trp Met Asn Gly Asp Arg
130                 135                 140

Ile Asp Ser Leu Leu Glu Xaa Asp Arg Gln Gln Xaa Xaa Xaa Leu Asp
145                 150                 155                 160

Xaa Met Gln Asp Xaa Phe Xaa Arg Ala Ser Xaa Ile Ile Asp Xaa Leu
                165                 170                 175

Phe Gln Asp Arg Phe Phe Xaa Arg Glu Xaa Xaa Asp Xaa Xaa Xaa Xaa
                180                 185                 190

Xaa Pro Xaa Xaa Xaa Pro His Xaa Arg Pro His Phe Xaa Xaa Pro Lys
                195                 200                 205

Ser Arg Xaa Val Arg Ser Leu Met Xaa Xaa Ser Xaa Tyr Xaa Pro Xaa
            210                 215                 220

Xaa Phe His Xaa Met Phe Gln Pro Phe Xaa Glu Met Ile His Xaa Ala
225                 230                 235                 240

Gln Gln Ala Met Asp Xaa Xaa Xaa His Ser Pro Ala Phe Gln Xaa Pro
                245                 250                 255

Xaa Xaa Xaa Phe Xaa Arg Glu Gly Xaa Asp Asp Arg Thr Val Cys Xaa

```
                  260                 265                 270
Glu Ile Arg Xaa Asn Ser Thr Gly Cys Leu Xaa Met Lys Xaa Gln Cys
            275                 280                 285
Xaa Lys Cys Xaa Glu Ile Leu Ser Val Asp Cys Ser Thr Asn Asn Pro
        290                 295                 300
Xaa Gln Ala Xaa Leu Arg Xaa Glu Leu Xaa Xaa Ser Leu Gln Val Ala
305                 310                 315                 320
Glu Arg Leu Thr Xaa Xaa Tyr Xaa Glu Leu Leu Xaa Ser Xaa Gln Xaa
                325                 330                 335
Lys Met Leu Asn Thr Ser Ser Leu Leu Glu Gln Leu Asn Xaa Gln Phe
            340                 345                 350
Asn Trp Val Ser Xaa Leu Ala Asn Leu Thr Gln Gly Glu Asp Xaa Tyr
            355                 360                 365
Tyr Leu Arg Val Xaa Thr Val Xaa Xaa His Xaa Ser Asp Ser Xaa Val
        370                 375                 380
Pro Ser Xaa Val Thr Glu Val Val Lys Leu Phe Asp Ser Asp Pro
385                 390                 395                 400
Ile Thr Val Xaa Xaa Pro Xaa Glu Val Ser Xaa Xaa Asn Pro Lys Phe
                405                 410                 415
Met Xaa Thr Val Ala Glu Lys Ala Leu Gln Glu Tyr Arg Xaa Lys Xaa
            420                 425                 430
Arg Xaa Glu
    435

<210> SEQ ID NO 58
<211> LENGTH: 121
<212> TYPE: PRT
<213> ORGANISM: Artificial Sequence
<220> FEATURE:
<223> OTHER INFORMATION: human model of 21B12 VH

<400> SEQUENCE: 58

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Ser Tyr
            20                  25                  30
Ala Met Asn Trp Val Arg Gln Ala Pro Gly Gln Gly Leu Glu Trp Met
        35                  40                  45
Gly Trp Ile Asn Thr Asn Thr Gly Asn Pro Thr Tyr Ala Gln Gly Phe
    50                  55                  60
Thr Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Asp Trp Gly Gln Gly Thr Leu Val Thr Val Ser Ser Val Ala
            100                 105                 110
Thr Ile Asp Glu Asn Trp Phe Asp Pro
            115                 120
```